US010118920B2

(12) United States Patent
Pegg et al.

(10) Patent No.: US 10,118,920 B2
(45) Date of Patent: Nov. 6, 2018

(54) ISOXAZOLYL SUBSTITUTED BENZIMIDAZOLES

(71) Applicant: CELLCENTRIC LTD, Cambridge, Cambridgeshire (GB)

(72) Inventors: Neil Anthony Pegg, Cambridge (GB); David Michel Adrien Taddei, Nottingham (GB); Stuart Thomas Onions, Nottingham (GB); Eric Sing Yuen Tse, Nottingham (GB); Richard James Brown, Nottingham (GB); David Kenneth Mycock, Nottingham (GB); David Cousin, Nottingham (GB); Anil Patel, Nottingham (GB)

(73) Assignee: CELLCENTRIC LTD, Cambridge, Cambrigeshire (GB)

( * ) Notice: Subject to any disclaimer, the term of this patent is extended or adjusted under 35 U.S.C. 154(b) by 0 days.

(21) Appl. No.: 15/567,768

(22) PCT Filed: Apr. 20, 2016

(86) PCT No.: PCT/GB2016/051088
§ 371 (c)(1),
(2) Date: Oct. 19, 2017

(87) PCT Pub. No.: WO2016/170324
PCT Pub. Date: Oct. 27, 2016

(65) Prior Publication Data
US 2018/0127402 A1 May 10, 2018

(30) Foreign Application Priority Data
Apr. 20, 2015 (GB) .................................... 1506658.2

(51) Int. Cl.
*C07D 413/14* (2006.01)
*A61P 35/00* (2006.01)
(Continued)

(52) U.S. Cl.
CPC ............ *C07D 413/14* (2013.01); *A61P 35/00* (2018.01); *C07D 403/14* (2013.01); *C07D 413/04* (2013.01); *C07D 471/04* (2013.01)

(58) Field of Classification Search
None
See application file for complete search history.

(56) References Cited

U.S. PATENT DOCUMENTS 3,538,097 A   11/1970  Loewe et al.
5,667,975 A    9/1997  Dykstra et al.
(Continued)

FOREIGN PATENT DOCUMENTS

CN    103728294 A    4/2014
CN    103880823 A    6/2014
(Continued)

OTHER PUBLICATIONS

International Search Report and Written Opinion dated Jun. 7, 2016 from International Application No. PCT/GB2016/051088, 10 pages.
UK Intellectual Property Office Search Report dated Jan. 15, 2016 for GB1506658.2, 6 pages.
Bedford et al., "Ubiquitin-like protein conjugation and the ubiquitin-proteasome system as drug targets", Nature Reviews Drug Discovery, Jan. 2011, vol. 10, No. 1, pp. 29-46.
Paul Brennan, "Isoxazole Inhibitors of Bromodomains", SGC Oxford, Nuffield Dept. of Clinical Medicine, University of Oxford, presented at RSC Advances in Synthesis and Medicinal Chemistry, May 1, 2012, 46 pages.
Cai et al., "Intratumoral De Novo Steroid Synthesis Activates Androgen Receptor in Castration-Resistant Prostate Cancer and Is Upregulated by Treatment with CYP17A1 Inhibitors", Cancer Research, Oct. 15, 2011, vol. 71, No. 20, pp. 6503-6513.
(Continued)

*Primary Examiner* — Kamal A Saeed
(74) *Attorney, Agent, or Firm* — MH2 Technology Law Group, LLP

(57) ABSTRACT

A compound which is a benzimidazolyl isoxazole of formula (I): wherein: $R^0$ and R, which are the same or different, are each H or $C_{1-6}$ alkyl; $R^9$, $R^9$ and $R^9$, which are the same or different, are each H or F; X is -(alk$_n$-, -alk-C(=O)—NR—, -alk-NR—C(=O)— or -alk-C(=O)—; $R^1$ is selected from —S(=O)$_2$R'; a 4- to 6-membered, C-linked heterocyclic group which is unsubstituted or substituted; and an N-linked spiro group of the following formula: $R^2$ and $R^{2'}$, which are the same or different, are each H or $C_{1-6}$ alkyl, or $R^2$ and $R^{2'}$ form, together with the C atom to which they are attached, a $C_{3-6}$ cycloalkyl group; $R^3$ and $R^3$, which are the same or different, are each H, $C_{1-6}$ alkyl, OH or F; $R^4$ is phenyl or a 5- to 12-membered, N-containing heteroaryl group and is unsubstituted or substituted; alk is $C_{1-6}$ alkylene; R' is $C_{1-6}$ alkyl; and n is 0 or 1; or a pharmaceutically acceptable salt thereof. The compound has activity in modulating the activity of p300 and/or CBP and is used to treat cancer, particularly prostate cancer.

(I)

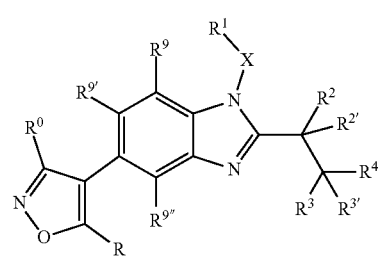

16 Claims, No Drawings

(51) Int. Cl.
*C07D 413/04* (2006.01)
*C07D 403/14* (2006.01)
*C07D 471/04* (2006.01)

(56) References Cited

U.S. PATENT DOCUMENTS

| | | | |
|---|---|---|---|
| 5,770,617 | A | 6/1998 | LaVoie et al. |
| 6,313,312 | B1 | 11/2001 | Banks et al. |
| 6,548,505 | B1 | 4/2003 | Martin et al. |
| 9,662,311 | B2 * | 5/2017 | Liu .................. A61K 31/4184 |
| 2003/0010971 | A1 | 1/2003 | Zhang et al. |
| 2005/0101647 | A1 | 5/2005 | Oda et al. |
| 2005/0256157 | A1 | 11/2005 | Gesner et al. |
| 2005/0261307 | A1 | 11/2005 | Cai et al. |
| 2007/0112048 | A1 | 5/2007 | Bavari et al. |
| 2008/0274418 | A1 | 11/2008 | Lin et al. |
| 2010/0316607 | A1 | 12/2010 | Or et al. |
| 2011/0046982 | A1 | 2/2011 | Arya et al. |
| 2011/0092415 | A1 | 4/2011 | DeGoey et al. |
| 2012/0230951 | A1 | 9/2012 | Alam et al. |
| 2014/0142798 | A1 | 5/2014 | Guamizo Martinez et al. |
| 2014/0364429 | A1 | 12/2014 | Zhan-Yun |

FOREIGN PATENT DOCUMENTS

| | | |
|---|---|---|
| CN | 103952009 A | 7/2014 |
| CN | 104030988 A | 9/2014 |
| CN | 104193738 A | 12/2014 |
| CN | 104710410 A | 6/2015 |
| CN | 104803989 A | 7/2015 |
| FR | 1519964 A | 4/1968 |
| JP | 2000292930 A | 10/2000 |
| JP | 2004024114 A | 1/2004 |
| JP | 2009005594 A | 1/2009 |
| JP | 2015088313 A | 5/2015 |
| KR | 10-2010-0099459 | 9/2010 |
| WO | 90/12321 | 10/1990 |
| WO | 96/06831 | 3/1996 |
| WO | 96/40114 | 12/1996 |
| WO | 96/40145 | 12/1996 |
| WO | 97/04776 | 2/1997 |
| WO | 98/33503 | 8/1998 |
| WO | 98/38170 | 9/1998 |
| WO | 99/41241 | 8/1999 |
| WO | 00/66528 | 11/2000 |
| WO | 01/32630 A1 | 5/2001 |
| WO | 01/46175 A1 | 6/2001 |
| WO | 01/53268 A2 | 7/2001 |
| WO | 01/85724 A1 | 11/2001 |
| WO | 03/017994 A1 | 3/2003 |
| WO | 03/048140 A1 | 6/2003 |
| WO | 2004/014881 A2 | 2/2004 |
| WO | 2004/018419 A2 | 3/2004 |
| WO | 2005/012288 A1 | 2/2005 |
| WO | 2005/033065 A1 | 4/2005 |
| WO | 2005/047244 A2 | 5/2005 |
| WO | 2005/080348 A1 | 9/2005 |
| WO | 2005/082894 A1 | 9/2005 |
| WO | 2005/086754 A2 | 9/2005 |
| WO | 2006/028269 A2 | 3/2006 |
| WO | 2006/033943 A2 | 3/2006 |
| WO | 2006/130673 A1 | 12/2006 |
| WO | 2007/027594 A1 | 3/2007 |
| WO | 2007/070173 A2 | 6/2007 |
| WO | 02/055025 A2 | 7/2007 |
| WO | 2008/074091 A1 | 6/2008 |
| WO | 2008/129007 A1 | 10/2008 |
| WO | 2008/140239 A1 | 11/2008 |
| WO | 2009/005551 A2 | 1/2009 |
| WO | 2009/087379 A2 | 7/2009 |
| WO | 2009/105140 A2 | 8/2009 |
| WO | 2010/065674 A9 | 6/2010 |
| WO | 2010/065681 A1 | 6/2010 |
| WO | 2010/075376 A2 | 7/2010 |
| WO | 2010/096777 A1 | 8/2010 |
| WO | 2010/132684 A9 | 11/2010 |
| WO | 2010/148006 A1 | 12/2010 |
| WO | 2011/007756 A1 | 1/2011 |
| WO | 2011/031904 A1 | 3/2011 |
| WO | 2011/075607 A1 | 6/2011 |
| WO | 2011/099832 A2 | 8/2011 |
| WO | 2011/119853 A1 | 8/2011 |
| WO | 2011/119858 A1 | 9/2011 |
| WO | 2011/119870 A1 | 9/2011 |
| WO | 2011/151618 A2 | 12/2011 |
| WO | 2012/044043 A2 | 4/2012 |
| WO | 2012/044567 A2 | 4/2012 |
| WO | 2012/051361 A1 | 4/2012 |
| WO | 2012/083170 A1 | 6/2012 |
| WO | 2012/135799 A1 | 10/2012 |
| WO | 2012/156284 A1 | 11/2012 |
| WO | 2012/167053 A1 | 12/2012 |
| WO | 2013/010904 A1 | 1/2013 |
| WO | 2013/036749 A1 | 3/2013 |
| WO | 2013/049567 A1 | 4/2013 |
| WO | 2013/052362 A1 | 4/2013 |
| WO | 2013/055607 A1 | 4/2013 |
| WO | 2013/059278 A2 | 4/2013 |
| WO | 2013/074387 A1 | 5/2013 |
| WO | 2013/093484 A1 | 6/2013 |
| WO | 2013/0114332 A1 | 8/2013 |
| WO | 2013/149997 A1 | 10/2013 |
| WO | 2014/019344 A1 | 2/2014 |
| WO | 2014/048072 A1 | 4/2014 |
| WO | 2014/081280 A2 | 5/2014 |
| WO | 2014/082381 A1 | 6/2014 |
| WO | 2014/125651 A1 | 8/2014 |
| WO | 2014/134240 A1 | 9/2014 |
| WO | 2014/151936 A1 | 9/2014 |
| WO | 2014/182929 A1 | 11/2014 |
| WO | 2015/004533 A2 | 1/2015 |
| WO | 2015/009678 A2 | 1/2015 |
| WO | 2015/031819 A1 | 3/2015 |
| WO | 2015/042438 A1 | 3/2015 |
| WO | 2015/054642 A2 | 4/2015 |
| WO | 2015/067108 A1 | 5/2015 |
| WO | 2015/177688 A1 | 11/2015 |
| WO | 2016/044694 A1 | 3/2016 |
| WO | 2016/097863 A1 | 6/2016 |
| WO | 2016/097870 A1 | 6/2016 |
| WO | 2016/170323 A1 | 10/2016 |

OTHER PUBLICATIONS

Debes et al., "p300 in Prostate Cancer Proliferation and Progression", Cancer Research, Nov. 15, 2003, vol. 63, pp. 7638-7640.
Denissen et al., "The Orally Active Renin Inhibitor A-74273, In Vivo and In Vitro Morpholine Ring Metabolism in Rats, Dogs, and Humans", Drug Metabolism and Disposition, 1994, vol. 22, No. 6, pp. 880-888.
Hay et al., "The design and synthesis of 5- and 6-isoxazolylbenzimidazoles as selective inhibitors of the BET promodomains", Med. Chem. Commun., 2013, vol. 4, pp. 140-144.
Hay et al., "Discovery and optimization of small molecule ligands for the CBP/p300 bromodomians", Journal of the American Chemical Society, Jul. 2, 2014, vol. 136, No. 26, pp. 9308-9319.
Jones et al., "The Epigenomics of Cancer", Cell, Feb. 23, 2007, vol. 128, pp. 683-692.
Linja et al., "Expression of Androgen Receptor Coregulators in Prostate Cancer", Clinical Cancer Research, Feb. 1, 2004, vol. 10, pp. 1032-1040.
George S Mack, "To selectivity and beyond", Nature Biotechnology, Dec. 2010, vol. 28, No. 12, pp. 1259-1266.
Zhong et al., "p300 Acetyltransferase Regulates Androgen Receptor Degradation and PTEN-Deficient Prostate Tumorigenesis", Cancer Research, Mar. 15, 2014, vol. 74, No. 6, pp. 1870-1880.

(56) References Cited

OTHER PUBLICATIONS

Chekler et al., "Transcriptional Profiling of a selective CREB Binding Protein Bromodomain Inhibitor Highlights Therapeutic Opportunities", Chemistry & Biology, Dec. 17, 2015, vol. 22, pp. 1588-1596.

* cited by examiner

ISOXAZOLYL SUBSTITUTED BENZIMIDAZOLES

CROSS-REFERENCE TO RELATED APPLICATIONS

This application is a U.S. National Stage application of PCT/GB2016/051088 filed 20 Apr. 2016, which claims priority to Great Britain Application No. 1506658.2 filed 20 Apr. 2015, the entire disclosures of which are hereby incorporated by reference in their entireties.

FIELD OF THE INVENTION

The present invention relates to a series of novel benzimidazolyl isoxazoles and to their use as modulators of p300 and/or CBP activity.

BACKGROUND TO THE INVENTION

Genetic and epigenetic modifications are critical to all stages of cancer disease progression and epigenetic silencing has been shown to be important in the misregulation of genes involved in all of the hallmarks of cancer (Jones, P. A. and Baylin, S. B. (2007) "The epigenomics of cancer", *Cell*, Vol. 128, pp. 683-692). The underlying epigenetic modifications that mediate regulation include DNA methylation and post translational histone modification. The latter includes methylation, acetylation, and ubiquitination. DNA-demethylating agents and histone deacetylase inhibitors have shown anti-tumour activity and a number of agents have been approved for use in the treatment of haematological malignancies. The enzymes mediating histone modification, including histone acetyltransferases (HATs) which acetylate histone and non-histone proteins, represent a wave of second generation targets for small molecule drug intervention.

Prostate cancer is the most common malignancy, and the second leading cause of cancer mortality among men. The treatment for clinically localised disease is typically surgery or radiation therapy. For patients who recur systemically after definitive treatment, or who present with loco-regional or metastatic disease, long term disease control is the primary objective. Typically, this entails a series of hormonal therapies that suppress androgen receptor (AR) signalling, since prostate cancers are exquisitely dependent upon AR function for survival and progression. Although AR targeted therapies inhibit tumour growth, disease is rarely eliminated and resistance to therapy is acquired through restored AR function. Progression to this 'castration resistant' prostate cancer (CRPC) represents the lethal phenotype of the illness. It is estimated that between 50-60% of patients that develop metastatic disease have CRPC. Recently, several new therapeutic agents have been approved for the treatment of CRPC. These however, provide limited clinical efficacy and serve only to prolong progression. Novel and tolerable agents are therefore necessary to make further gains in the treatment of CRPC.

Multiple cellular mechanisms lead to the progression of CRPC. In all cases, acquisition of the CRPC phenotype is mediated via re-activation of the AR pathway. The acetyltransferase p300 directly regulates AR levels and AR signalling activity in prostate cancer cells (Zhong et al., 'p300 acetyltransferase regulates androgen-receptor degradation and PTEN-deficient prostate tumorigenesis,' *Cancer Res*., Vol. 74, pp. 1870-1880, 2014). Therapeutic modulation of p300 activity would therefore target all known adaptive mechanisms which lead to the development of CRPC. Approved therapies and those in clinical studies primarily target only one or other of theses cellular mechanisms. The modulation of p300 activity directly provides an opportunity to more broadly modulate AR activity in CRPC than current and other experimental therapeutic strategies. In addition, resistance mechanisms to recently approved agents have been shown to be AR-dependent (Cai, C. et al., (2011) 'Intratumoral de novo steroid synthesis activates androgen receptor in castration-resistant prostate cancer and is up-regulated by treatment with Cyp17A1 inhibitors,' *Cancer Res*., Vol. 71, pp. 6503-6513). Modulation of p300 should therefore inhibit resistance to current therapies and potentially provide improved and sustained efficacy and greater clinical utility.

In common with p300, the CREB (cyclic-AMP response element binding protein) binding protein (CBP) is an acetyltransferase that acts as a transcriptional co-activator in human cells. Both CBP and p300 possess a single bromodomain (BRD) and a lysine acetyltransferase (KAT) domain, which are involved in the post-translational modification and recruitment of histones and non-histone proteins. There is high sequence similarity between CBP and p300 in the conserved functional domains (see Duncan A. Hay et al, JACS 2014, 135, 9308-9319). Modulation of CBP activity therefore provides a promising route to the treatment of certain cancers. Accordingly, compounds that can modulate, e.g. inhibit, the activity of p300 and/or CBP are of interest in cancer therapy.

SUMMARY OF THE INVENTION

It has now been found that a series of novel compounds have activity in modulating p300 and/or CBP activity. The compounds therefore have potential utility in treating cancer, particularly prostate cancer.

Accordingly, the present invention provides a compound which is a benzimidazolyl isoxazole of formula (I):

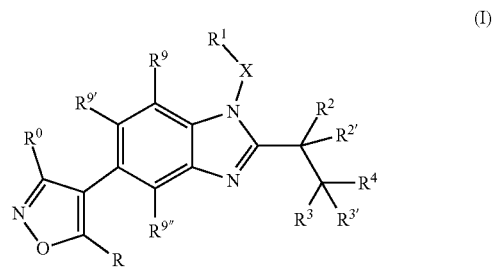

wherein:

$R^0$ and R, which are the same or different, are each H or $C_{1-6}$ alkyl;

$R^9$, $R^{9'}$ and $R^{9''}$, which are the same or different, are each H or F;

X is $-(alk)_n-$, $-alk-C(=O)-NR-$, $-alk-NR-C(=O)-$ or $-alk-C(=O)-$;

$R^1$ is selected from $-S(=O)_2R'$, a 4- to 6-membered, C-linked heterocyclic group which is unsubstituted or substituted and an N-linked spiro group of the following formula:

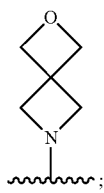 [SMILES: *N1CC2(COC2)C1]

R² and R²', which are the same or different, are each H or C₁₋₆ alkyl; or R² and R²' form, together with the C atom to which they are attached, a C₃₋₆ cycloalkyl group;

R³ and R³', which are the same or different, are each H, C₁₋₆ alkyl, OH or F;

R⁴ is phenyl or a 5- to 12-membered N-containing heteroaryl group and is unsubstituted or substituted;

alk is C₁₋₆ alkylene;

R' is C₁₋₆ alkyl; and n is 0 or 1;

or a pharmaceutically acceptable salt thereof.

In another aspect the invention provides a pharmaceutical composition comprising a benzimidazolyl isoxazole of formula (I) as defined above or a pharmaceutically acceptable salt thereof and a pharmaceutically acceptable carrier. The pharmaceutical composition may further comprise one or more additional chemotherapeutic agents, for instance as mentioned below.

In a further aspect the invention provides a benzimidazolyl isoxazole of formula (I) as defined above, or a pharmaceutically acceptable salt thereof, for use as a modulator of p300 activity.

DETAILED DESCRIPTION OF THE INVENTION

The term "substituted" includes the implicit provision that substitution be in accordance with the permitted valence of the substituted atom and the substituent and that the substitution results in a stable compound (i.e. one that does not spontaneously undergo transformation such as a rearrangement cyclisation, or elimination). In certain embodiments, a single atom may be substituted with more than one substituent as long as such substitution is in accordance with the permitted valence of the atom. In certain embodiments, a group that is substituted may be substituted by one substituent group or it may be multiply substituted on multiple carbon atoms. When any group defined herein is substituted, it is typically substituted by $R^{10}$ as defined below. The group may, for instance, be mono-, di- or tri-substituted by a group $R^{10}$ as defined below.

In certain of the benzimidazolyl isoxazoles of formula (I), dependant on the nature of the substituent, there may be chiral carbon atoms and therefore the compounds may exist as stereoisomers. The invention extends to all optical isomers such as stereoisomeric forms of the compounds of formula (I), including enantiomers, diastereomers and mixtures thereof, such as racemates. The different stereoisomeric forms may be separated or resolved one from the other by conventional methods or any given isomer may be obtained by conventional stereoselective or sterospecific syntheses.

The compounds of the invention can exist in various tautomeric forms and it is to be understood that the invention encompasses all such tautomeric forms.

It is understood that certain compounds of the invention contain both acidic and basic groups and may therefore exist as zwitterions at certain pH values.

As used herein, the terms "treat" and "treatment" refer to both therapeutic treatment and prophylactic or preventative measures, wherein the object is to prevent or slow down (lessen) an undesired physiological change or disorder, such as the development or spread of cancer. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "pharmaceutically acceptable" indicates that the substance or composition must be compatible chemically and/or toxicologically with the other ingredients comprising a formulation, and/or the patient being treated therewith.

A C₁₋₆ alkyl group or moiety is linear or branched. A C₁₋₆ alkyl group is typically a C₁₋₄ alkyl group, or a C₁₋₂ alkyl group. Examples of C₁₋₆ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). Typically a C₁₋₆ alkyl group is methyl (Me). For the avoidance of doubt, where two alkyl moieties are present in a group, the alkyl moieties may be the same or different. A C₁₋₆ alkyl group is unsubstituted or substituted, typically by one or more groups $R^{10}$ as defined below. For example, a C₁₋₆ alkyl group is unsubstituted or substituted by 1, 2 or 3 groups $R^{10}$ as defined below.

A C₁₋₆ alkylene group or moiety is an unsubstituted or substituted, linear or branched, saturated divalent aliphatic hydrocarbon group or moiety containing 1 to 6 carbon atoms. Typically it is a C₁₋₃ alkylene group or moiety. Examples include methylene, ethylene, n-propylene and i-propylene groups and moieties. More typically it is methylene or ethylene. When the alkylene group is substituted it is typically substituted by a group $R^{10}$ as defined below.

A C₃₋₆ cycloalkyl group or moiety is a saturated monovalent hydrocarbon ring having 3 to 6 carbon atoms. It is thus a 3-, 4-, 5- or 6-membered carbocyclic ring containing only saturated bonds. Examples of a cycloalkyl group include cyclopropyl, cyclobutyl, cyclopentyl and cyclohexyl. In one embodiment a cycloalkyl group is cyclopropyl.

A 5- to 12-membered N-containing heteroaryl group or moiety is a monovalent 5- to 12-membered aromatic heterocyclic group which contains 1, 2, 3, or 4 nitrogen atoms, typically 1 or 2 N atoms. It is linked via one of its ring N atoms or C atoms and is monocyclic or bicyclic. In one embodiment it is N-linked. In another embodiment it is C-linked. It may be, for example, a 5- to 7-membered N-containing monocyclic heteroaryl group, for instance a 5- or 6-membered N-containing heteroaryl group. Examples of a 5- to 12-membered, N-containing heteroaryl group include pyrrolyl, imidazolyl, pyridyl, pyrazinyl, pyrimidinyl, quinolyl, isoquinolyl, quinazolinyl, quinoxalinyl, indolyl, isoindolyl, indazolyl, pyrrolopyridinyl and pyrrolopyrimidinyl groups. When substituted, a 5- to 12-membered, N-containing heteroaryl group is typically substituted by one or more, e.g. 1, 2 or 3, groups selected from unsubstituted C₁₋₄ alkyl and a group $R^{11}$ as defined below In one embodiment a 5- to 12-membered, N-containing heteroaryl group is unsubstituted.

A 4- to 6-membered C-linked heterocyclic group is a saturated monovalent 4-, 5- or 6-membered heterocyclic ring containing at least one heteroatom selected from O, N and S. It is linked via one of its ring C atoms. Examples include oxetane, thietane, azetidine, pyrrolidine, piperidine, tetrahydropyran, tetrahydrothiopyran and tetrahydrofuran. A 4- to 6-membered C-linked, heterocyclic group is unsubstituted or substituted, typically by a group $R^{10}$ as defined below. It may be substituted on a ring carbon atom or on a ring N or S atom, as permitted by the valency of the atom.

A halogen or halo group is F, Cl, Br or I. Typically it is F, Cl or Br, more typically F.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups $R^{10}$ as defined below.

When in formula (I) n=0, moiety -(alk)$_n$- is absent and X is thus a direct bond. X is typically selected from a direct bond, —CH$_2$—, —CH$_2$CH$_2$—, —CH$_2$CH$_2$CH$_2$—, —CH$_2$—C(=O)—NMe-, —CH$_2$—C(=O)—NH— and —CH$_2$—C(=O)—.

When $R^1$ is a 4- to 6-membered C-linked heterocyclic group it is typically a piperidinyl, pyrrolidinyl, tetrahydropyranyl, tetrahydrothiopyranyl or tetrahydrofuranyl group. It is unsubstituted or substituted, for instance by a group $R^{10}$ as defined below.

When $R^4$ is a 5- to 12-membered N-containing heteroaryl group it is typically selected from pyrrolyl, imidazolyl, pyridyl, pyrazinyl, pyrimidinyl, quinolyl, isoquinolyl, quinazolinyl, quinoxalinyl, indolyl, isoindolyl, indazolyl, pyrrolopyridinyl and pyrrolopyrimidinyl. More typically it is selected from pyridyl, pyrimidinyl, quinolyl, isoquinolyl, quinoxalinyl, and pyrrolopyridinyl.

$R^4$ is unsubstituted or substituted. When substituted it may be mono-, di- or tri-substituted, for instance by a group $R^1$ as defined below.

$R^{10}$ is selected from unsubstituted $C_{1-6}$ alkyl, $C_{3-6}$ cycloalkyl, halo, OH, $C_{1-6}$ alkoxy, —C(O)R", —C(O)$_2$R", —C(O)NR"$_2$, oxo (=O), dioxo, —CH$_2$OR", —S(O)$_m$R", —NR"C(O)R", —S(O)$_m$NR"$_2$, and CF$_3$, wherein m is 1 or 2 and each R" is independently selected from H and unsubstituted $C_{1-6}$ alkyl. Typically $R^{10}$ is selected from unsubstituted $C_{1-6}$ alkyl, halo, OH, $C_{1-6}$ alkoxy, —C(O)R", —C(O)NR"$_2$, oxo (=O) and dioxo.

$R^{11}$ is selected from unsubstituted $C_{1-6}$ alkyl, halo, —OH, $C_{1-6}$ alkoxy, —CN, —OCHF$_2$, —OCF$_3$, —C(O)R", —C(O)$_2$R", —C(O)NR"$_2$, —CH$_2$OR", —S(O)$_m$R" and —S(O)$_m$NR"$_2$ wherein m and R" are as defined above.

In one preferred embodiment, the benzimidazolyl isoxazole of the invention has the following formula (Ia):

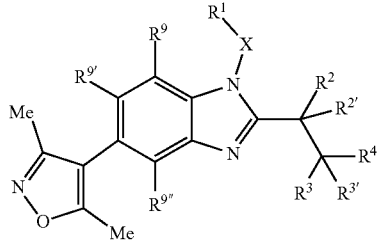

(Ia)

wherein each of $R^9$, $R^{9'}$, $R^{9''}$, X, $R^1$, $R^2$, $R^{2'}$, $R^3$, $R^{3'}$ and $R^4$ is as defined above for formula (I).

In another preferred embodiment of the invention, the benzimidazolyl isoxazole has the following formula (Ib):

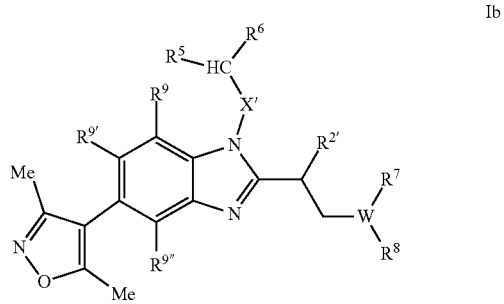

Ib wherein:

$R^9$, $R^{9'}$ and $R^{9''}$ are as defined above for formula (I);

X' is $C_{1-3}$ alkylene or —(CH$_2$)—C(=O)—NH—;

$R^{2'}$ is H, Me or Et;

$R^5$ is H and $R^6$ is —S(=O)$_2$Me, or $R^5$ and $R^6$ form, together with the carbon atom to which they are attached, a heterocyclic group selected from pyrrolidinyl, thiopyranyl, pyranyl and piperidinyl, which group is unsubstituted or substituted;

W is C or N; and $R^7$ and $R^8$ form, together with the C or N atom to which they are attached, a group selected from phenyl, pyridinyl, pyrimidinyl, quinolinyl, isoquinolinyl, pyrrolopyridinyl and quinoxalinyl, which group is unsubstituted or substituted.

In one aspect of the invention, the moiety represented in formulae (I) and (Ia) as —X—$R^1$ and in formula (Ib) as

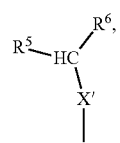

is selected from the following structures:

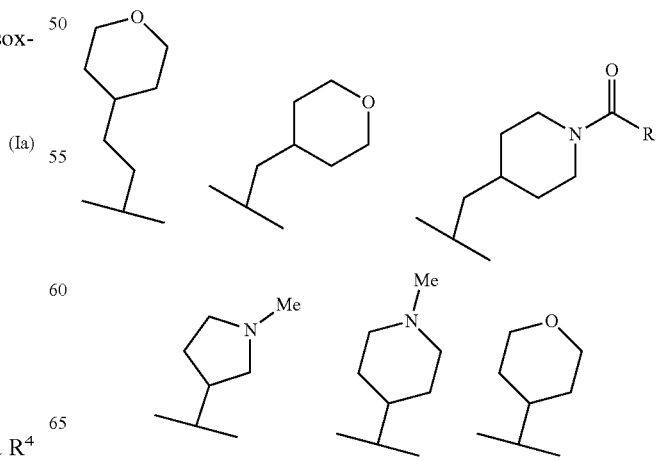

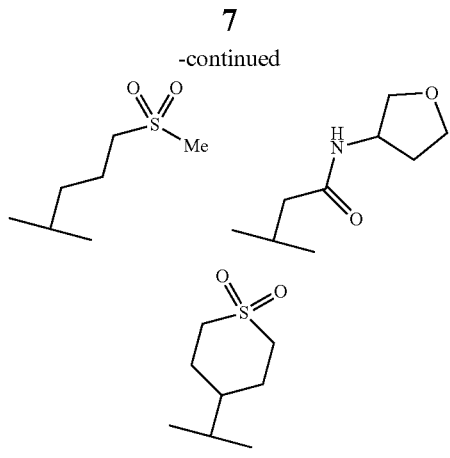

In another aspect of the invention, the moiety represented in formula (I) and (Ia) as

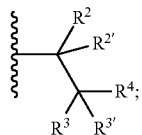

and in formula (Ib) as

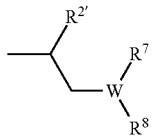

is represented by one of the following structures:

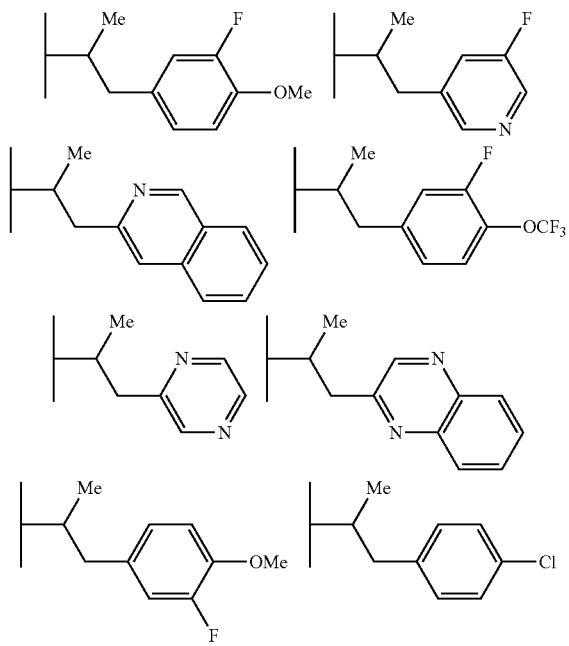

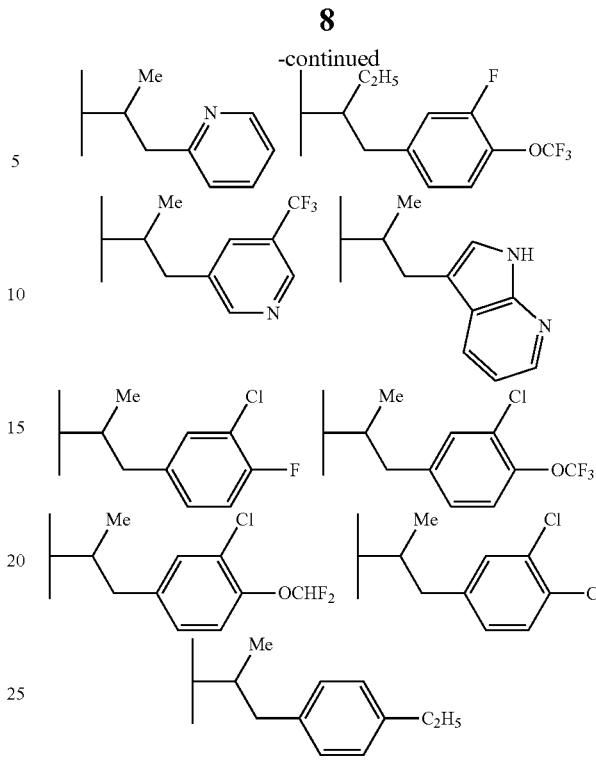

In formula (I) as defined above, each of $R^0$ and R is independently H or $C_{1-6}$ alkyl. Thus, for instance, $R^0$ is H and R is $C_{1-6}$ alkyl; R is H and $R^0$ is $C_{1-6}$ alkyl; each of $R^0$ and R is H; or each of $R^0$ and R is $C_{1-6}$ alkyl. In each of these variants $C_{1-6}$ alkyl is typically methyl or ethyl, preferably methyl.

In formulae (I) and (Ia) as defined above, each of $R^2$ and $R^{2'}$ is independently H or $C_{1-6}$ alkyl. For instance, $R^2$ is H and $R^{2'}$ is $C_{1-6}$ alkyl; $R^{2'}$ is H and $R^2$ is $C_{1-6}$ alkyl; $R^2$ and $R^{2'}$ are both H; or $R^2$ and $R^{2'}$ are both $C_{1-6}$ alkyl. In each of these variants $C_{1-6}$ alkyl is typically methyl or ethyl, preferably methyl. Alternatively $R^2$ and $R^{2'}$ form, together with the C atom to which they are attached, a $C_{3-6}$ cycloalkyl group such as cyclopropyl.

In one variant of formulae (I), (Ia) and (Ib) as defined above, each of $R^9$, $R^{9'}$ and $R^{9''}$ is H. In another variant, one of $R^9$, $R^{9'}$ and $R^{9''}$ is F and the other two are H. In a third variant, two of $R^9$, $R^{9'}$ and $R^{9''}$ are F and the other is H.

Compounds of the invention may contain asymmetric or chiral centres and thus exist in different stereoisomeric forms. The structural formulae (I), (Ia) and (Ib) above encompass all stereoisomeric forms of the compounds of the invention including disastereomers, enantiomers and racemic mixtures. Diastereomers and enantiomers may be obtained by stereoselective synthetic strategies, for instance via enantiomeric synthesis as illustrated in the Examples below.

In one stereoisomeric variant of formula (I) as defined above, $R^2$ is H, $R^{2'}$ is $C_{1-6}$ alkyl, and the C—$R^{2'}$ bond is either C◄R$^{2'}$ (the S enantiomer) or C⋯R$^{2'}$ (the R enantiomer). Typically the C—$R^{2'}$ bond is C⋯R$^{2'}$ and the compound is the R enantiomer. Accordingly, in one embodiment of formulae (I), (Ia) and (Ib) as defined above, $R^2$ (in the case of formulae (I) and (Ia)) is H, $R^{2'}$ is $C_{1-6}$ alkyl, the C—$R^{2'}$ bond is C⋯R$^{2'}$ and the compound is the R enantiomer. The R enantiomer is preferred.

In another stereoisomeric variant of formula (I) X is -(alk)$_n$- in which n is 0, such that $R^1$ is directly bonded to N. In this variant the N—$R^1$ bond is either N◄$R^1$ (the R enantiomer) or N⋯$R^1$ (the S enantiomer). The S enantiomer is preferred.

Specific examples of compounds of the invention include those listed in the following table:

| No | Structure | Name |
|---|---|---|
| 1 | 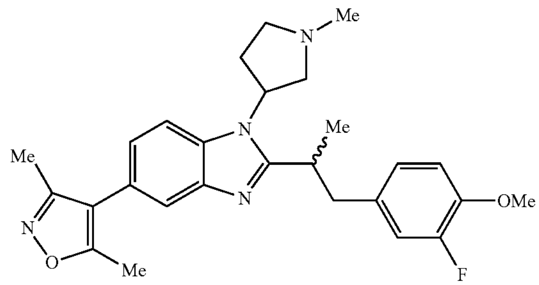 [SMILES: COc1ccc(CC(C)c2nc3cc(-c4c(C)noc4C)ccc3n2C2CCN(C)C2)cc1F] | 4-(2-(1-(3-fluoro-4-methoxyphenyl)propan-2-yl)-1-(1-methylpyrrolidin-3-yl)-1H-benzo[d]imidazol-5-yl)-3,5-dimethylisoxazole |
| 2 | 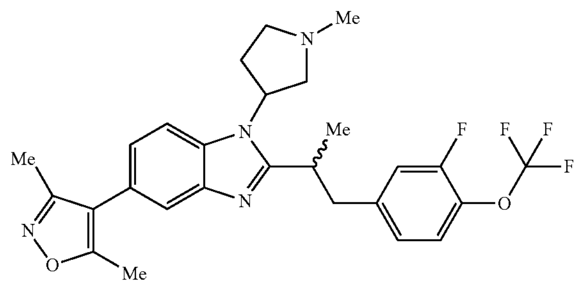 [SMILES: Cc1noc(C)c1-c1ccc2c(c1)nc(C(C)Cc1ccc(OC(F)(F)F)c(F)c1)n2C1CCN(C)C1] | 4-(2-(1-(3-fluoro-4-(trifluoromethoxy)phenyl)propan-2-yl)-1-(1-methylpyrrolidin-3-yl)-1H-benzo[d]imidazol-5-yl)-3,5-dimethylisoxazole |
| 3 | 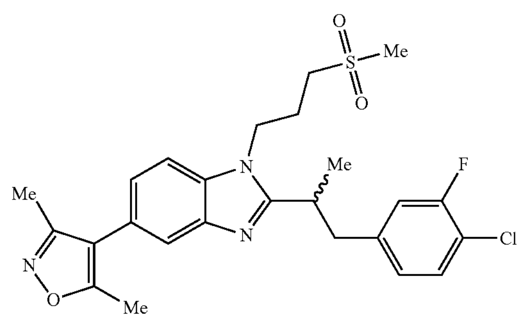 [SMILES: Cc1noc(C)c1-c1ccc2c(c1)nc(C(C)Cc1ccc(Cl)c(F)c1)n2CCCS(C)(=O)=O] | 4-(2-(1-(4-chloro-3-fluorophenyl)propan-2-yl)-1-(3-(methylsulfonyl)propyl)-1H-benzo[d]imidazol-5-yl)-3,5-dimethylisoxazole |
| 4 | 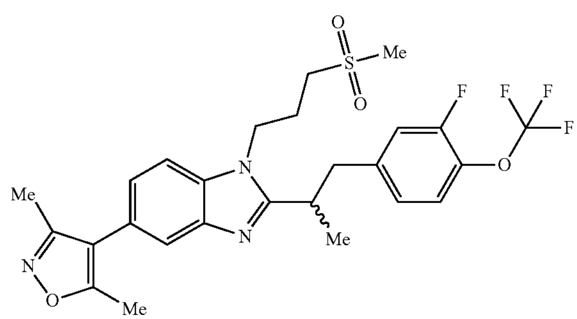 [SMILES: Cc1noc(C)c1-c1ccc2c(c1)nc(C(C)Cc1ccc(OC(F)(F)F)c(F)c1)n2CCCS(C)(=O)=O] | 4-(2-(1-(3-fluoro-4-(trifluoromethoxy)phenyl)propan-2-yl)-1-(3-(methylsulfonyl)propyl)-1H-benzo[d]imidazol-5-yl)-3,5-dimethylisoxazole |
| 5 | 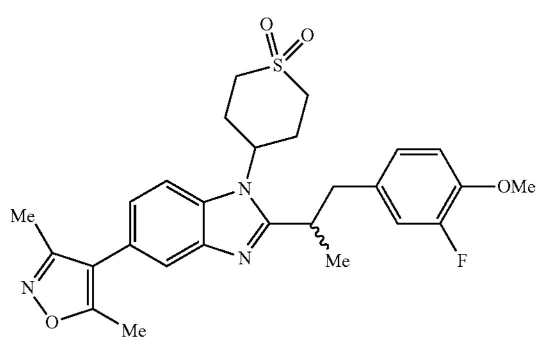 [SMILES: COc1ccc(CC(C)c2nc3cc(-c4c(C)noc4C)ccc3n2C2CCS(=O)(=O)CC2)cc1F] | 4-(5-(3,5-dimethylisoxazol-4-yl)-2-(1-(3-fluoro-4-methoxyphenyl)propan-2-yl)-1H-benzo[d]imidazol-1-yl)tetrahydro-2H-thiopyran 1,1-dioxide |

-continued

| No | Structure | Name |
|---|---|---|
| 6 | 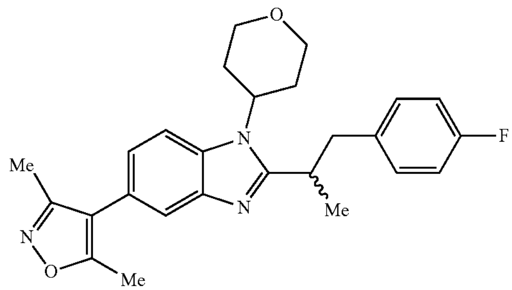 [SMILES: Cc1noc(C)c1-c1ccc2c(c1)nc(C(C)Cc1ccc(F)cc1)n2C1CCOCC1] | 4-(2-(1-(4-fluorophenyl)propan-2-yl)-1-(tetrahydro-2H-pyran-4-yl)-1H-benzo[d]imidazol-5-yl)-3,5-dimethylisoxazole |
| 7 | 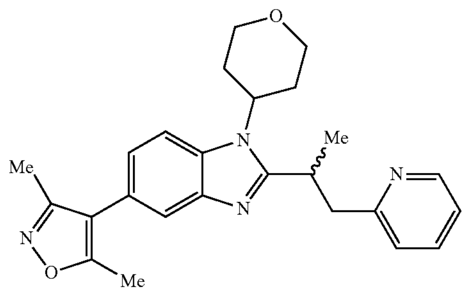 [SMILES: Cc1noc(C)c1-c1ccc2c(c1)nc(C(C)Cc1ccccn1)n2C1CCOCC1] | 3,5-dimethyl-4-(2-(1-(pyridin-2-yl)propan-2-yl)-1-(tetrahydro-2H-pyran-4-yl)-1H-benzo[d]imidazol-5-yl)isoxazole |
| 8 | 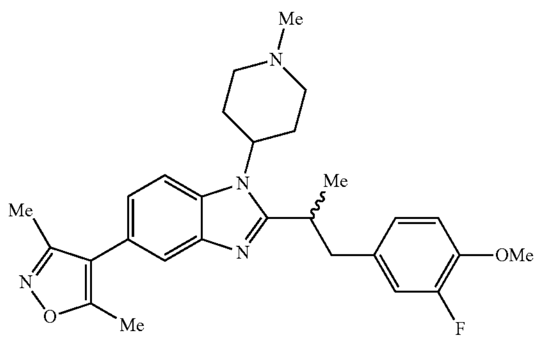 [SMILES: COc1ccc(CC(C)c2nc3cc(-c4c(C)noc4C)ccc3n2C2CCN(C)CC2)cc1F] | 4-(2-(1-(3-fluoro-4-methoxyphenyl)propan-2-yl)-1-(1-methylpiperidin-4-yl)-1H-benzo[d]imidazol-5-yl)-3,5-dimethylisoxazole |
| 9 | 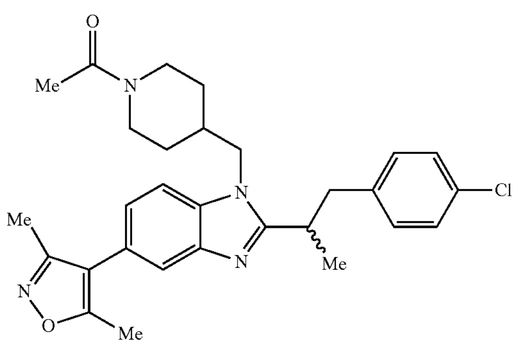 [SMILES: CC(=O)N1CCC(Cn2c(C(C)Cc3ccc(Cl)cc3)nc3cc(-c4c(C)noc4C)ccc32)CC1] | 1-(4-((2-(1-(4-chlorophenyl)propan-2-yl)-5-(3,5-dimethylisoxazol-4-yl)-1H-benzo[d]imidazol-1-yl)methyl)piperidin-1-yl)ethan-1-one |
| 10 | 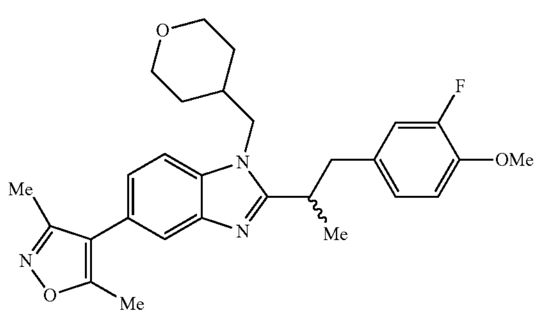 [SMILES: COc1ccc(CC(C)c2nc3cc(-c4c(C)noc4C)ccc3n2CC2CCOCC2)cc1F] | 4-(2-(1-(3-fluoro-4-methoxyphenyl)propan-2-yl)-1-((tetrahydro-2H-pyran-4-yl)methyl)-1H-benzo[d]imidazol-5-yl)-3,5-dimethylisoxazole |

-continued

| No | Structure | Name |
|----|-----------|------|
| 11 | 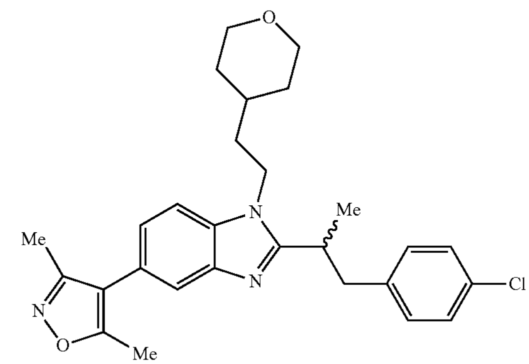 [SMILES: Cc1noc(C)c1-c1ccc2c(c1)nc(C(C)Cc1ccc(Cl)cc1)n2CCC1CCOCC1] | 4-(2-(1-(4-chlorophenyl)propan-2-yl)-1-(2-(tetrahydro-2H-pyran-4-yl)ethyl)-1H-benzo[d]imidazol-5-yl)-3,5-dimethylisoxazole |
| 12 | 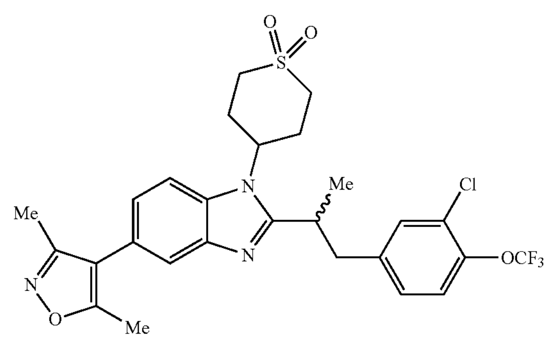 [SMILES: Cc1noc(C)c1-c1ccc2c(c1)nc(C(C)Cc1ccc(OC(F)(F)F)c(Cl)c1)n2C1CCS(=O)(=O)CC1] | 4-(2-(1-(3-chloro-4-(trifluoromethoxy)phenyl)propan-2-yl)-5-(3,5-dimethylisoxazol-4-yl)-1H-benzo[d]imidazol-1-yl)tetrahydro-2H-thiopyran 1,1-dioxide |
| 13 | 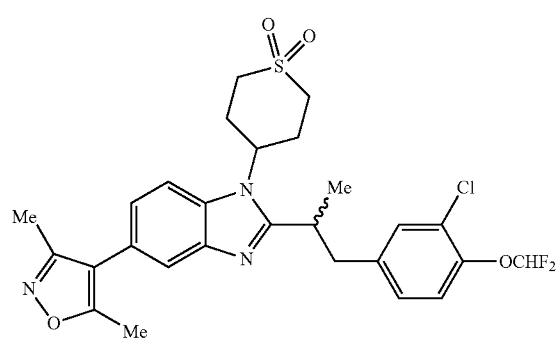 [SMILES: Cc1noc(C)c1-c1ccc2c(c1)nc(C(C)Cc1ccc(OC(F)F)c(Cl)c1)n2C1CCS(=O)(=O)CC1] | 4-(2-(1-(3-chloro-4-(difluoromethoxy)phenyl)propan-2-yl)-5-(3,5-dimethylisoxazol-4-yl)-1H-benzo[d]imidazol-1-yl)tetrahydro-2H-thiopyran 1,1-dioxide |
| 14 | 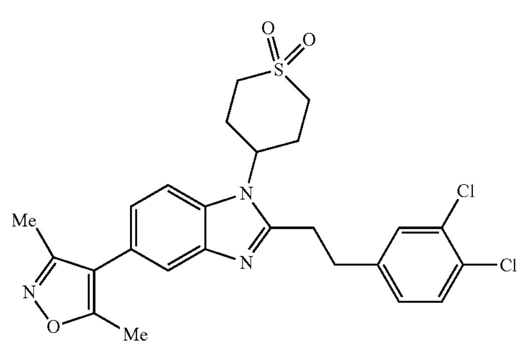 [SMILES: Cc1noc(C)c1-c1ccc2c(c1)nc(CCc1ccc(Cl)c(Cl)c1)n2C1CCS(=O)(=O)CC1] | 4-(2-(3,4-dichlorophenethyl)-5-(3,5-dimethylisoxazol-4-yl)-1H-benzo[d]imidazol-1-yl)tetrahydro-2H-thiopyran 1,1-dioxide |

| No | Structure | Name |
|---|---|---|
| 15 | 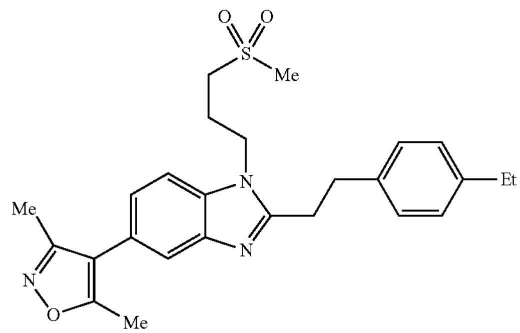 [SMILES: CCc1ccc(CCc2nc3cc(-c4c(C)noc4C)ccc3n2CCCS(C)(=O)=O)cc1] | 4-(2-(4-ethylphenethyl)-1-(3-(methylsulfonyl)propyl)-1H-benzo[d]imidazol-5-yl)-3,5-dimethylisoxazole |
| 16 | 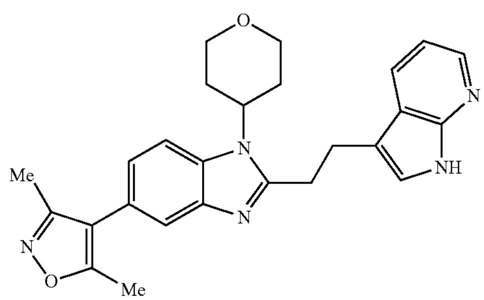 [SMILES: Cc1noc(C)c1-c1ccc2c(c1)nc(CCc1c[nH]c3ncccc13)n2C1CCOCC1] | 4-(2-(2-(1H-pyrrolo[2,3-b]pyridin-3-yl)ethyl)-1-(tetrahydro-2H-pyran-4-yl)-1H-benzo[d]imidazol-5-yl)-3,5-diemthylisoxazole |
| 17 | 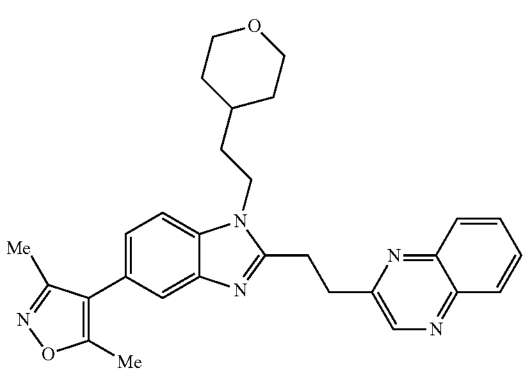 [SMILES: Cc1noc(C)c1-c1ccc2c(c1)nc(CCc1cnc3ccccc3n1)n2CCC1CCOCC1] | 3,5-dimethyl-4-(2-(2-(quinoxalin-2-yl)ethyl)-1-(2-(tetrahydro-2H-pyran-4-yl)ethyl)-1H-benzo[d]imidazol-5-yl)isoxazole |
| 18 | 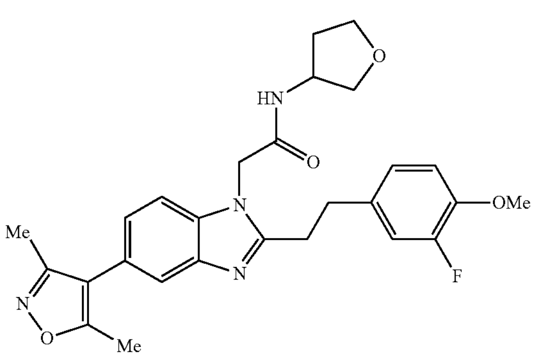 [SMILES: COc1ccc(CCc2nc3cc(-c4c(C)noc4C)ccc3n2CC(=O)NC2CCOC2)cc1F] | 2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide |

-continued

| No | Structure | Name |
|----|-----------|------|
| 19 | 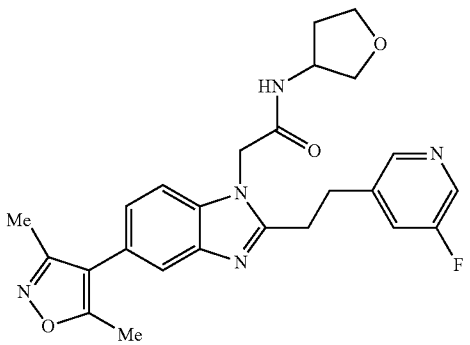 [SMILES: Cc1noc(C)c1-c1ccc2c(c1)nc(CCc1cncc(F)c1)n2CC(=O)NC1CCOC1] | 2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide |
| 20 | 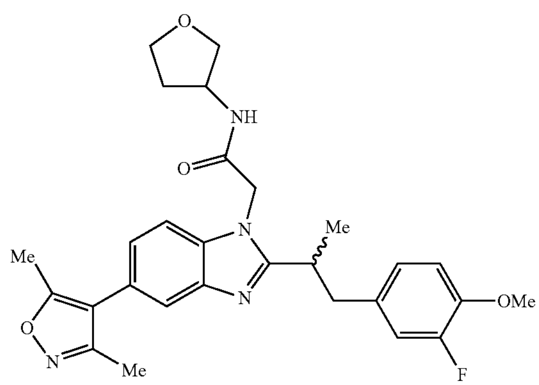 [SMILES: COc1ccc(CC(C)c2nc3cc(-c4c(C)noc4C)ccc3n2CC(=O)NC2CCOC2)cc1F] | 2-(5-(3,5-dimethylisoxazol-4-yl)-2-(1-(3-fluoro-4-methoxyphenyl)propan-2-yl)-1H-benzo[d]imidazol-1-yl)-N-(tetrahydrofuran-3-yl)acetamide |
| 22 | 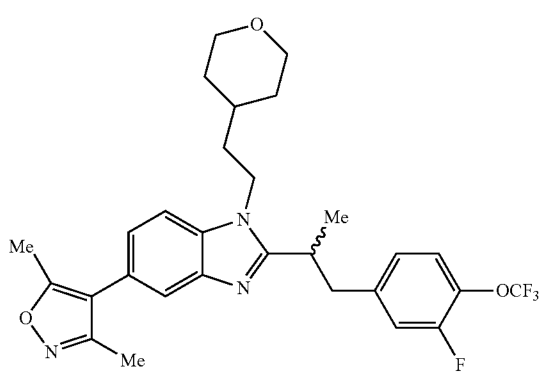 [SMILES: Cc1noc(C)c1-c1ccc2c(c1)nc(C(C)Cc1ccc(OC(F)(F)F)c(F)c1)n2CCC1CCOCC1] | 4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole |
| 23 | 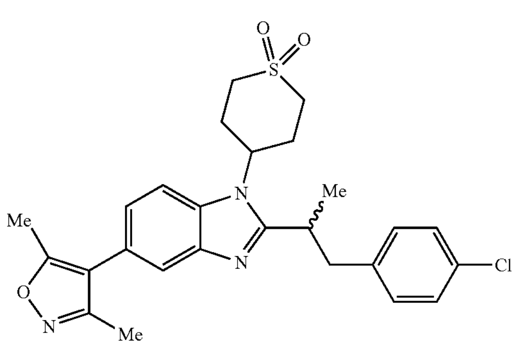 [SMILES: Cc1noc(C)c1-c1ccc2c(c1)nc(C(C)Cc1ccc(Cl)cc1)n2C1CCS(=O)(=O)CC1] | 4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide |

| No | Structure | Name |
|---|---|---|
| 24 | 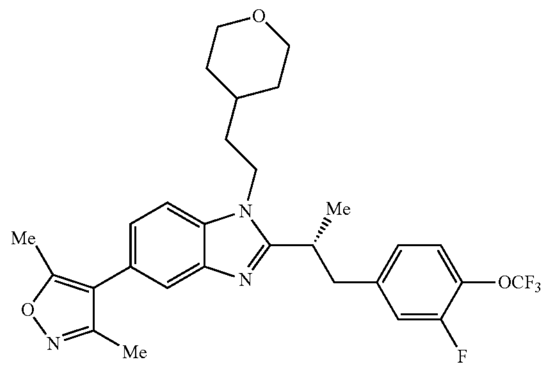 [SMILES: Cc1noc(C)c1-c1ccc2c(c1)nc([C@H](C)Cc1ccc(OC(F)(F)F)c(F)c1)n2CCC1CCOCC1] | (R)-4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole |
| 25 | 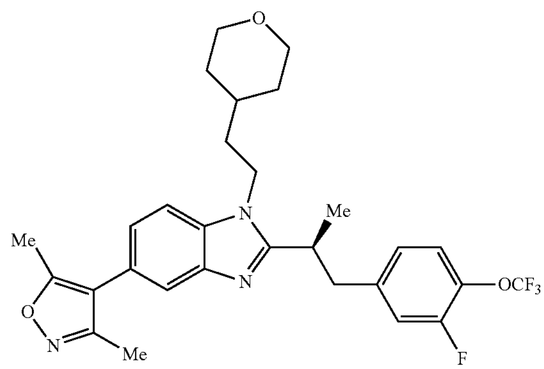 [SMILES: Cc1noc(C)c1-c1ccc2c(c1)nc([C@@H](C)Cc1ccc(OC(F)(F)F)c(F)c1)n2CCC1CCOCC1] | (S)-4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole |
| 26 | 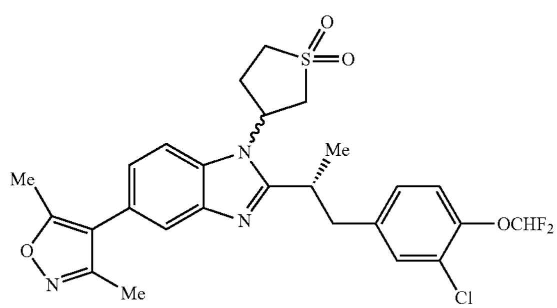 [SMILES: Cc1noc(C)c1-c1ccc2c(c1)nc([C@H](C)Cc1ccc(OC(F)F)c(Cl)c1)n2C1CCS(=O)(=O)C1] | 3-(2-((R)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide |
| 27 | 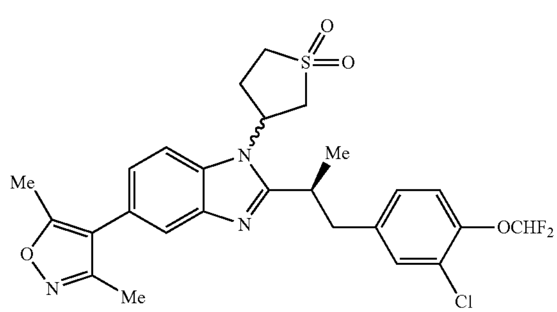 [SMILES: Cc1noc(C)c1-c1ccc2c(c1)nc([C@@H](C)Cc1ccc(OC(F)F)c(Cl)c1)n2C1CCS(=O)(=O)C1] | 3-(2-((S)-1-(3-chloro-4-(difluoromethxoy)phenyl)propan-2-yl)-5-(3,5-dimethylisoxazol-4-yl)-1H-benzo[d]imidazol-1-yl)tetrahydrothiophene 1,1-dioxide |

| No | Structure | Name |
|---|---|---|
| 28 | 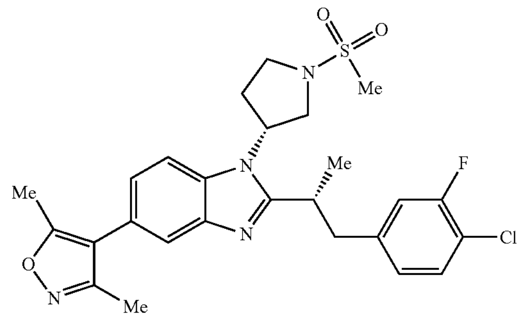 [SMILES: Cc1noc(C)c1-c1ccc2c(c1)nc([C@H](C)Cc1ccc(Cl)c(F)c1)n2[C@@H]1CCN(S(C)(=O)=O)C1] | 4-(2-((R)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole |
| 29 | 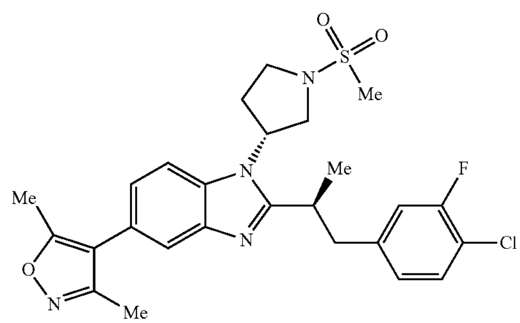 [SMILES: Cc1noc(C)c1-c1ccc2c(c1)nc([C@@H](C)Cc1ccc(Cl)c(F)c1)n2[C@@H]1CCN(S(C)(=O)=O)C1] | 4-(2-((S)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole |
| 30 | 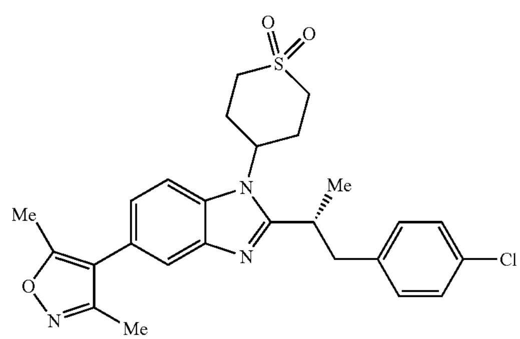 [SMILES: Cc1noc(C)c1-c1ccc2c(c1)nc([C@H](C)Cc1ccc(Cl)cc1)n2C1CCS(=O)(=O)CC1] | (R)-4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide |
| 31 | 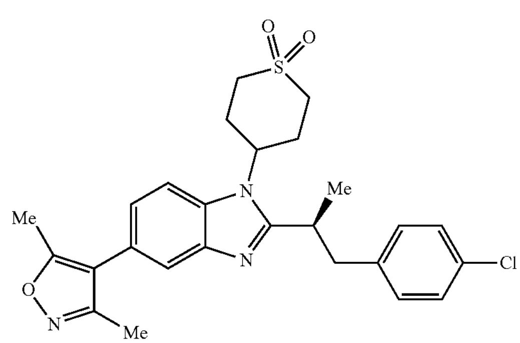 | (S)-4-(2-(1-(4-chlorophenyhl)propan-2-yl)-5-(3,5-dimethylisoxazol-4-yl)-1H-benzo[d]imidazol-1-yl)tetrahydro-2H-thiopyran 1,1-dioxide |

-continued

| No | Structure | Name |
|---|---|---|
| 32 | 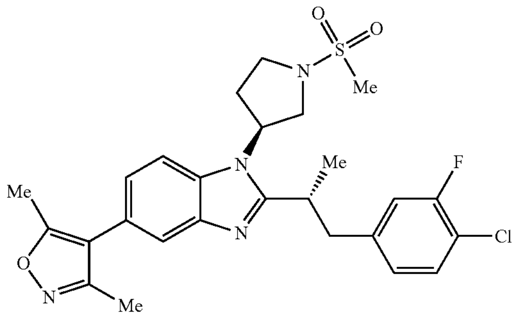 [SMILES: Cc1noc(C)c1-c1ccc2c(c1)nc([C@H](C)Cc1ccc(Cl)c(F)c1)n2[C@H]1CCN(S(C)(=O)=O)C1] | 4-(2-((R)-1-(4-chloro-3-fluorophenyl)propan-2-yl)-1-((S)-1-(methylsulfonyl)pyrrolidin-3-yl)-1H-benzo[d]imidazol-5-yl)-3,5-dimethylisoxazole |
| 33 | 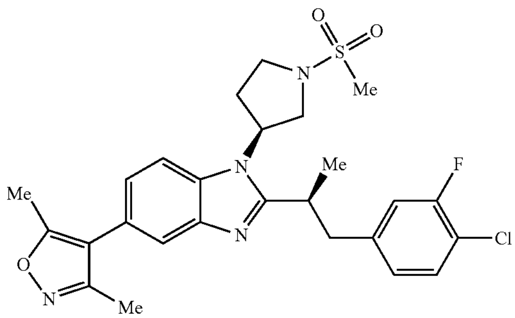 [SMILES: Cc1noc(C)c1-c1ccc2c(c1)nc([C@@H](C)Cc1ccc(Cl)c(F)c1)n2[C@H]1CCN(S(C)(=O)=O)C1] | 4-(2-((S)-1-(4-chloro-3-fluorophenyl)propan-2-yl)-1-((S)-1-(methylsulfonyl)pyrrolidin-3-yl)-1H-benzo[d]imidazol-5-yl)-3,5-dimethylisoxazole |
| 34 | 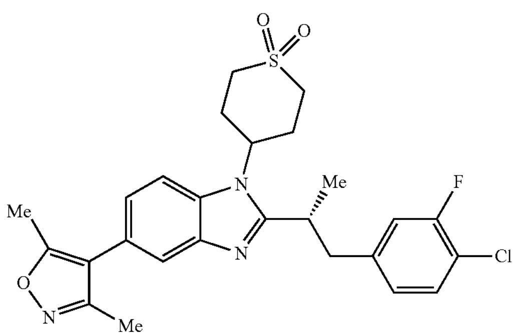 [SMILES: Cc1noc(C)c1-c1ccc2c(c1)nc([C@H](C)Cc1ccc(Cl)c(F)c1)n2C1CCS(=O)(=O)CC1] | (R)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide |
| 35 | 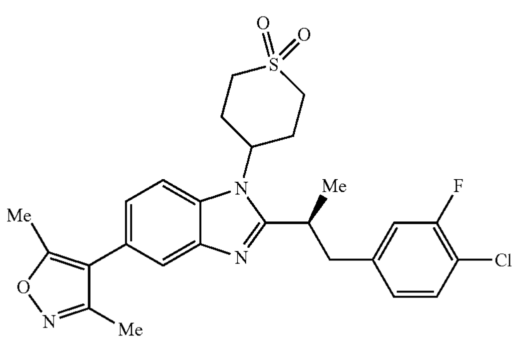 [SMILES: Cc1noc(C)c1-c1ccc2c(c1)nc([C@@H](C)Cc1ccc(Cl)c(F)c1)n2C1CCS(=O)(=O)CC1] | (S)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide |
| 36 | 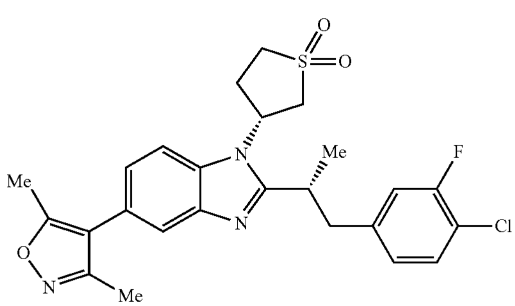 [SMILES: Cc1noc(C)c1-c1ccc2c(c1)nc([C@H](C)Cc1ccc(Cl)c(F)c1)n2[C@@H]1CCS(=O)(=O)C1] | ((R)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide |

| No | Structure | Name |
|---|---|---|
| 37 | 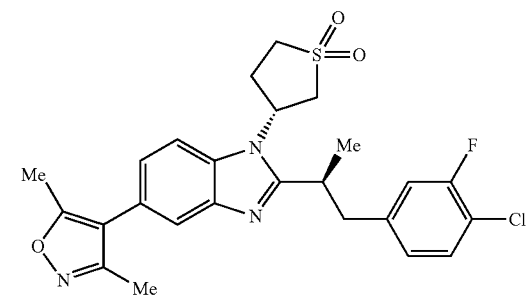 [SMILES: Cc1noc(C)c1-c1ccc2c(c1)nc([C@@H](C)Cc1ccc(Cl)c(F)c1)n2[C@@H]1CCS(=O)(=O)C1] | ((R)-3-(2-((S)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide |
| 38 | 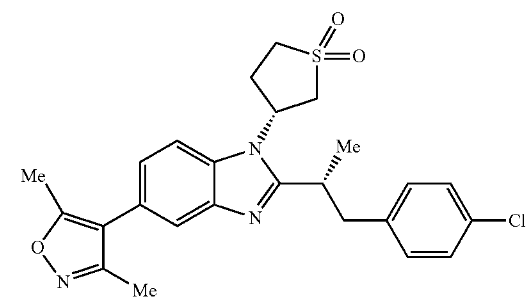 [SMILES: Cc1noc(C)c1-c1ccc2c(c1)nc([C@H](C)Cc1ccc(Cl)cc1)n2[C@@H]1CCS(=O)(=O)C1] | (R)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide |
| 39 | 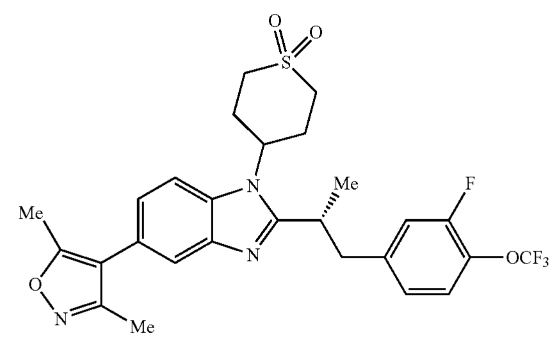 [SMILES: Cc1noc(C)c1-c1ccc2c(c1)nc([C@H](C)Cc1ccc(OC(F)(F)F)c(F)c1)n2C1CCS(=O)(=O)CC1] | (R)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide |
| 40 | 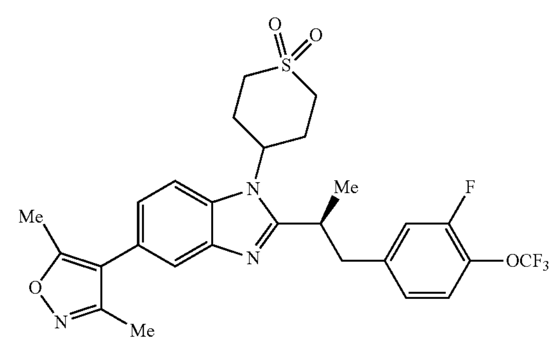 [SMILES: Cc1noc(C)c1-c1ccc2c(c1)nc([C@@H](C)Cc1ccc(OC(F)(F)F)c(F)c1)n2C1CCS(=O)(=O)CC1] | (S)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide |
| 41 | 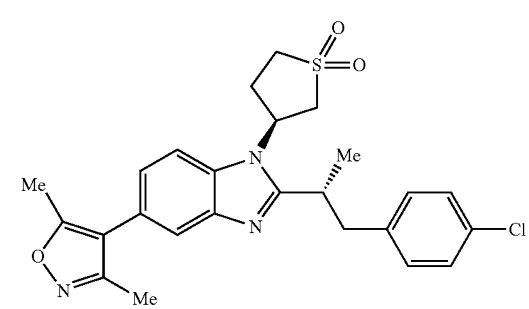 [SMILES: Cc1noc(C)c1-c1ccc2c(c1)nc([C@H](C)Cc1ccc(Cl)cc1)n2[C@H]1CCS(=O)(=O)C1] | (S)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide |

-continued

| No | Structure | Name |
|----|-----------|------|
| 42 | 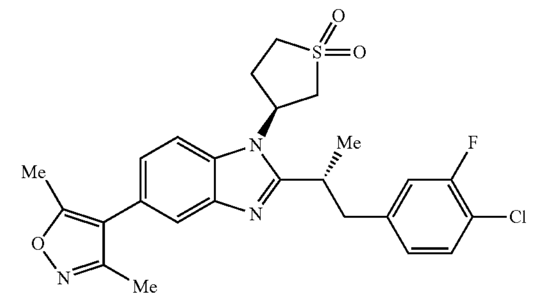 [SMILES: Cc1noc(C)c1-c1ccc2c(c1)nc([C@H](C)Cc1ccc(Cl)c(F)c1)n2[C@H]1CCS(=O)(=O)C1] | (S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide |
| 43 | 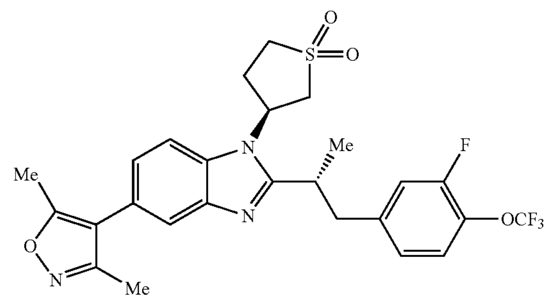 [SMILES: Cc1noc(C)c1-c1ccc2c(c1)nc([C@H](C)Cc1ccc(OC(F)(F)F)c(F)c1)n2[C@H]1CCS(=O)(=O)C1] | (S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide |
| 44 | 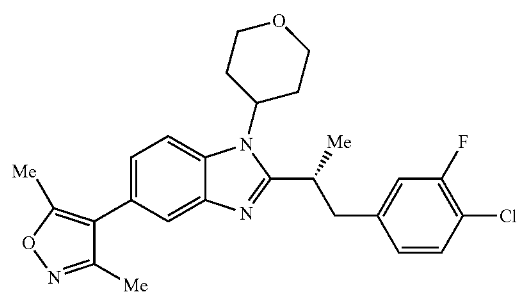 [SMILES: Cc1noc(C)c1-c1ccc2c(c1)nc([C@H](C)Cc1ccc(Cl)c(F)c1)n2C1CCOCC1] | (R)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole |
| 45 | | (S)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole | and the pharmaceutically acceptable salts thereof.

A compound of the invention may be prepared by a process which comprises treating a compound of formula (II):

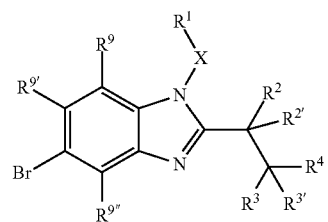

wherein each of $R^1$, $R^2$, $R^{2'}$, $R^3$, $R^{3'}$, $R^4$, $R^9$, $R^{9'}$ and $R^{9''}$ is as defined above for formula (I), with a boronic acid of formula (III):

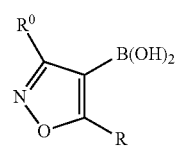

(III)

in which each of R⁰ and R is as defined above for formula (I), in the presence of Pd(PPh₃)₄ and Na₂CO₃ in aqueous ethanol. The aqueous ethanol is typically 30-70% EtOH/water.

The two schemes shown below illustrate specific synthetic strategies by which compounds of the invention may be produced.

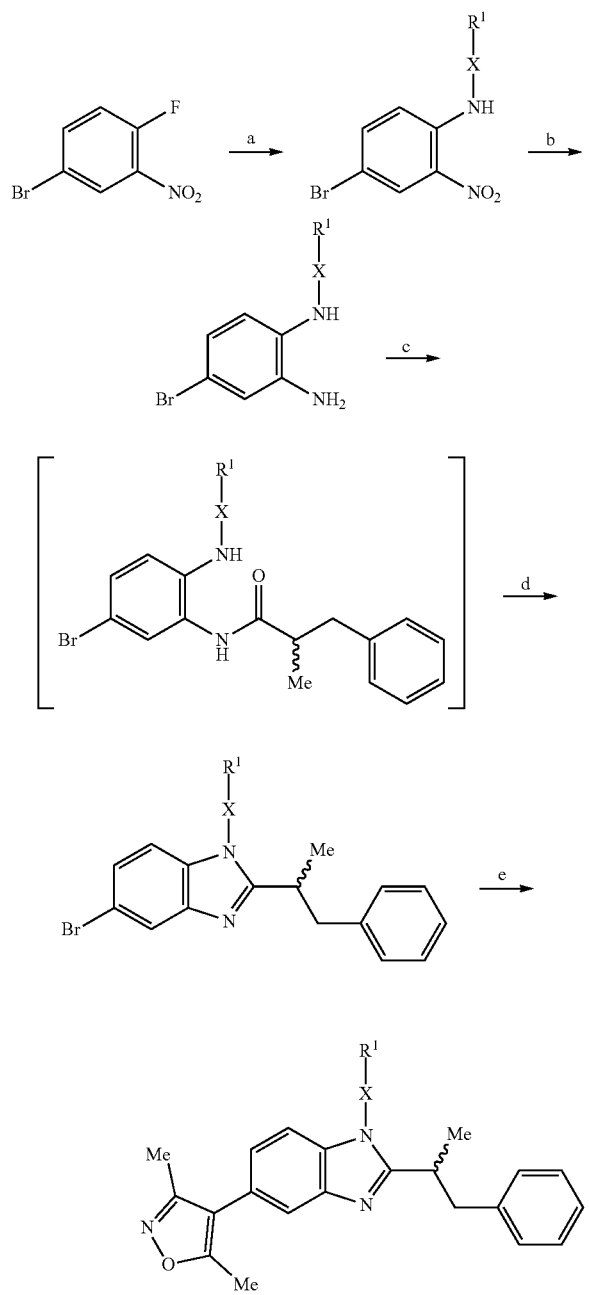

Route A a. R₁—X—NH₂, TEA, THF, rt or R₁—NH₂·HCl, TEA, DMF, 70-90° C.-60-90%
b. Na₂S₂O₄, THF/H₂O, NH₄OH or Fe, AcOH or Fe, NH₄Cl, EtOH/H₂O, 80° C.-30-80%
c. HATU, hydrocinnamic acid, TEA, DCM or DMF-50-90% (either purified or used crude)
d. AcOH, 60-100° C. or HCl/1,4-dioxane-20-90%
e. Dimethylisoxazoleboronic acid, Na₂CO₃, Pd(PPh₃)₄, EtOH/water-30-70%

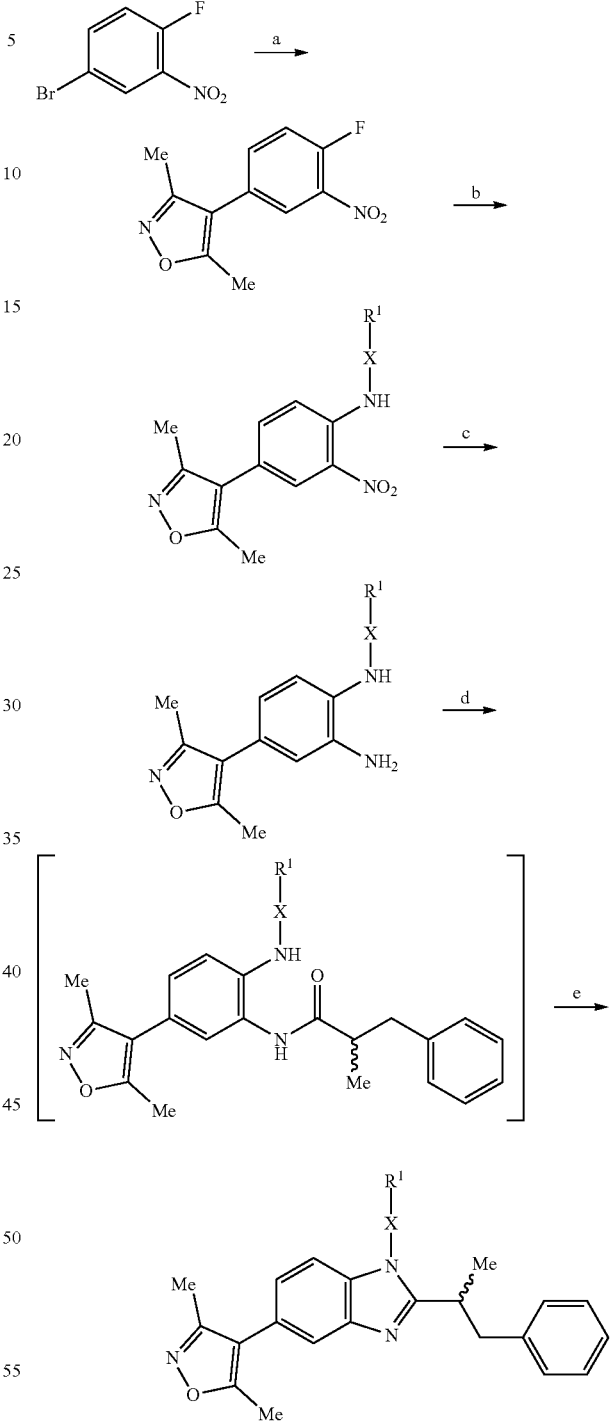

Route B a. Dimethylisoxazoleboronic acid, Na₂CO₃, Pd(PPh₃)₄, EtOH/water-50-70%
b. R₁—NH₂, TEA, THF, rt or R₁—NH₂·HCl, TEA, DMF, 70-90° C.-60-90%
c. Na₂S₂O₄, THF/H₂O, NH₄OH or Fe, AcOH or Fe, NH₄Cl, EtOH/H₂O, 80° C.-30-80%
d. HATU, hydrocinnamic acid, TEA, DCM or DMF-50-90% (either purified or used crude)
e. AcOH, 60-100° C. or HCl/1,4-dioxane-20-90%

The following schemes illustrate strategies for synthesising intermediates and chiral intermediates that can be used in the synthesis of chiral compounds of the invention:

Route C: Synthesis of 3-arylpropanoic acid

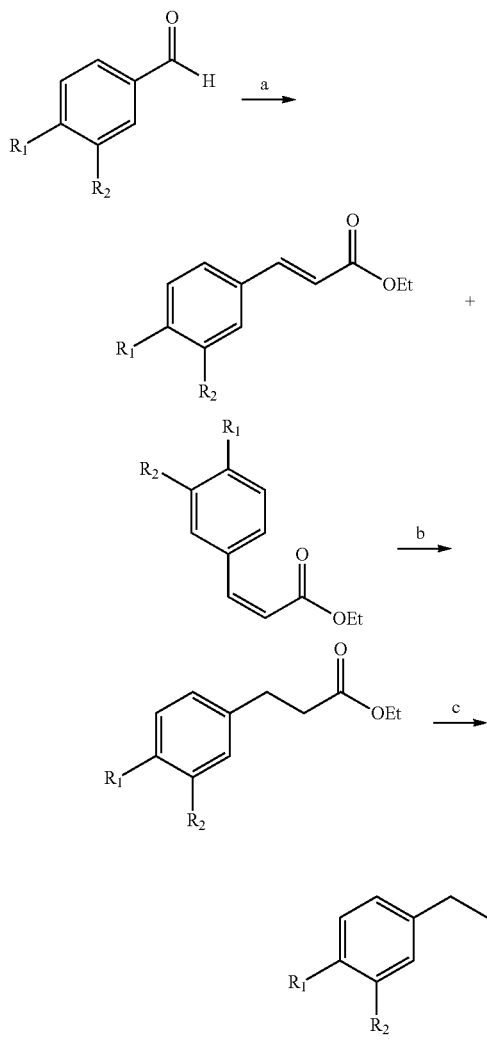

a. Ph$_3$P=CHCOOEt, THF
b. Catalyst, H$_2$, EtOH
c. NaOH, MeOH

Route D(i): Synthesis of (R)-3-aryl-2-methylpropanoic acid

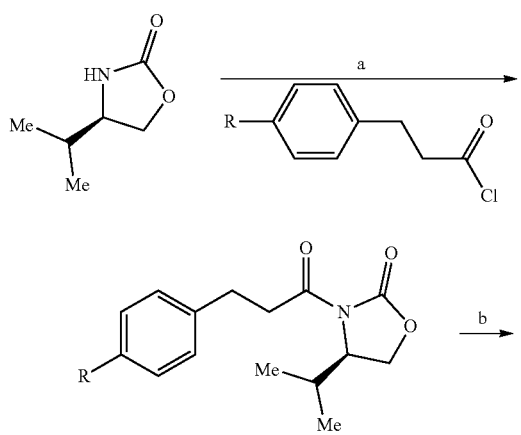

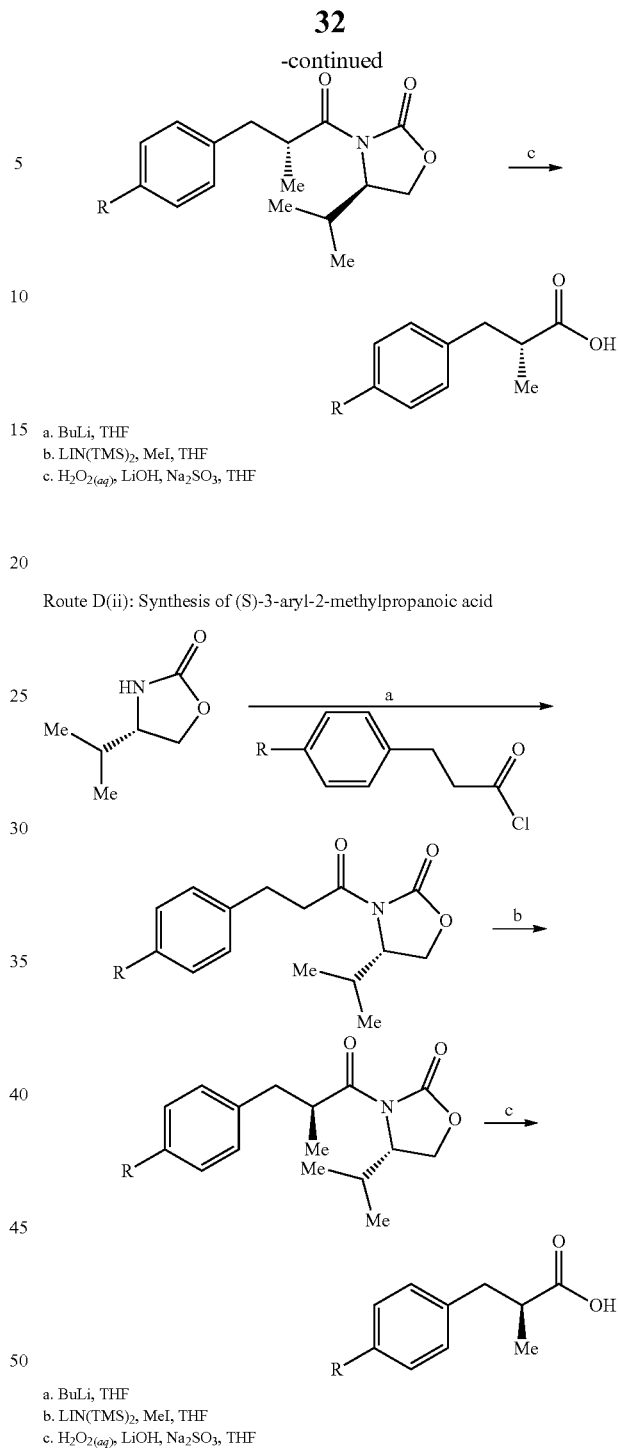

a. BuLi, THF
b. LiN(TMS)$_2$, MeI, THF
c. H$_2$O$_{2(aq)}$, LiOH, Na$_2$SO$_3$, THF

Route D(ii): Synthesis of (S)-3-aryl-2-methylpropanoic acid a. BuLi, THF
b. LiN(TMS)$_2$, MeI, THF
c. H$_2$O$_{2(aq)}$, LiOH, Na$_2$SO$_3$, THF The preparation of chiral intermediates is illustrated in the Reference Examples that follow below.

A key to the abbreviations used in all the above schemes is provided in the Examples section below.

A benzimidazolyl isoxazole of formula (I) may be converted into a pharmaceutically acceptable salt, and salts may be converted into the free compound, by conventional methods. Pharmaceutically acceptable salts include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds bearing a free carboxy substituent, the salts include both the above-mentioned acid addition salts and the salts of sodium, potassium, calcium and ammonium. The latter are prepared by treating the free benzimidazolyl isoxazole of formula (I), or an acid addition salt thereof, with the corresponding metal base or ammonia.

A benzimidazolyl isoxazole of formula (I) or a pharmaceutically acceptable salt thereof is hereafter referred to as a compound of the invention. Compounds of the invention have been found in biological tests to bind to the histone acetyltransferase (HAT), p300, as described in Example 46 below.

p300 is a transcriptional coactivator involved in the regulation of multiple biological processes; proliferation, apoptosis, cell cycle regulation and DNA damage response. p300 primarily functions as a transcription cofactor for a number of oncoproteins including Jun, Fos and E2F. In addition, it acts as a histone acetyltransferase and can also acetylate multiple non-histone proteins such as p53, p73, and Rb. p300 has been reported to act as a tumour suppressor or as an oncoprotein dependent upon the nature of the cancer. Multiple studies have shown that p300 expression correlates with disease progression and decreased survival.

p300 is up-regulated in human prostate cancer progression and has been shown to be an AR co-activator (Debes, J. D., et al., (2003) 'p300 in prostate cancer proliferation and progression,' *Cancer Res.*, Vol. 63, pp. 7638-7640; and Linja, M. J. et al., (2004) 'Expression of androgen receptor coregulators in prostate cancer,' *Clin. Cancer Res.*, Vol. 10, pp. 1032-1040).

p300 has recently been shown to directly regulate AR protein degradation (Zhong et al., 2014). p300 mediated AR acetylation was shown to inhibit AR ubiquitination and subsequent AR proteasome degradation (Zhong et al., 2014, cited above). The direct inhibition of p300 activity would therefore promote AR degradation.

Given the high molecular heterogeneity of prostate cancer, the identification of appropriate biomarkers is critical to the effective positioning and evaluation of targeted small molecule therapies. It is proposed that markers of the development of the CRPC phenotype via AR resurgence are used for patient stratification for the evaluation of p300 modulators. These include PSA and circulating tumour cell (CTC) counts. In terms of biomarkers to enable the monitoring of the modulation of p300 activity, direct readouts include; determination of the AR and AR splice variant levels; modulation of AR activity by assessing levels of AR responsive genes including PSA, TMPRSS2 and KLK2. Other surrogate markers of AR functional activity include p21, c-Myc and p53. Given that multiple therapeutic agents which modulate AR activity are approved for use in CRPC, biomarkers to assess effects of p300 targeting and subsequent AR modulation are already widely available and used in clinical settings.

Various types of cancer have been shown to express AR. In addition to prostate cancer, these include breast and bladder cancer. Modulation of p300 activity would be expected to have therapeutic utility in the treatment of such cancers and other indications in which AR is expressed. In addition, it is feasible that p300 regulates the levels of other nuclear hormone receptors, thereby further expanding the clinical utility of p300 targeted agents.

A compound of the invention has activity as a modulator p300 and/or CBP activity. It may therefore be used to treat cancer, or another clinical condition in which AR is expressed. The cancers that can be treated are those which express AR, or which are otherwise associated with AR. These cancers include prostate cancer, breast cancer and bladder cancer. The prostate cancer may be, for instance, castration-resistant prostate cancer (CRPC). A human or animal patient suffering from cancer may thus be treated by a method comprising the administration thereto of a compound of the invention. The condition of the patient may thereby be improved or ameliorated.

A compound of the invention may thus be administered to a human or animal patient in conjunction with radiotherapy or another chemotherapeutic agent for the treatment of cancer. The present invention therefore further provides a combination therapy wherein a compound of the invention, or a pharmaceutical composition comprising a compound of the invention, is administered concurrently or sequentially with radiotherapy; or is administered concurrently sequentially or as a combined preparation with another chemotherapeutic agent or agents, for the treatment of cancer.

The or each other chemotherapeutic agent will be an agent conventionally used for the type of cancer being treated. Classes of chemotherapeutic agents with which a compound of the invention is typically combined for the treatment of prostate cancer include androgen receptor antagonists, for instance Enzalutamide, and inhibitors of CYP17A1 (17α-hydroxylase/C17,20 lyase), for instance Abiraterone. Other chemotherapeutic agents with which a compound of the invention could be administered in combination therapy include Docetaxel.

The term "combination" as used herein refers to simultaneous, separate or sequential administration. Where the administration is sequential or separate, the delay in administering the second component should not be such as to lose the beneficial effect of the combination.

The present invention further provides a product comprising
  (a) a compound of the invention as defined above; and
  (b) a chemotherapeutic agent;
for separate, simultaneous or sequential administration in the prophylactic or therapeutic treatment of cancer, for instance the specific types of cancer mentioned above. The chemotherapeutic agent may be, for instance, an androgen receptor antagonist or an inhibitor of CYP17A1. More specifically, it may Enzalutamide or Abiraterone.

A compound of the invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound of the invention is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan monooleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

C) By inhalation, in the form of aerosols or solutions for nebulizers.

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

E) Topically, in the form of creams, ointments, jellies, collyriums, solutions or suspensions.

The invention will be further described in the Examples and Reference Examples which follow:

Examples

Abbreviations

AcOH glacial acetic acid
aq aqueous
Ac acetyl
Boc tert-butoxycarbonyl
br broad
CatCart® catalytic cartridge
CDI 1,1-carbonyl-diimidazole
d doublet
DCM Dichloromethane
DIPEA N,N-diisopropylethylamine
DMF N,N-dimethylformamide
DMSO dimethyl sulfoxide
(ES+) electrospray ionization, positive mode
Et Ethyl
EtOAc ethyl acetate
FCS foetal calf serum
HOBt 1-hydroxybenzotriazole
hr hour(s)
(M+H)+ protonated molecular ion
Me methyl
MeCN acetonitrile
MeOH methanol
MHz megahertz
min minute(s)
m/z: mass-to-charge ratio
NMP 1-methylpyrrolidin-2-one (N-methyl-2-pyrrolidone)
NMR nuclear magnetic resonance (spectroscopy)
Ph phenyl
PBS phosphate buffered saline
PPh$_3$ triphenylphosphine
q quartet
RT room temperature
RP HPLC reverse phase high performance liquid chromatography
s singlet
SCX solid supported cation exchange (resin)
S$_N$Ar nucleophilic aromatic substitution
t triplet
TBAF tetrabutylammonium fluoride
TEA triethylamine
TFA trifluoroacetic acid
THF tetrahydrofuran
TIPS-Cl chlorotriisopropylsilane
TMB 3,3',5,5'-tetramethylbenzidine
XantPhos 4,5-bis(diphenylphosphino)-9,9-dimethylxanthene
HATU N-[(Dimethylamino)-1H-1,2,3-triazolo-[4,5-b]pyridin-1-ylmethylene]-N-methylmethanaminium hexafluorophosphate N-oxide

General Procedures

All starting materials and solvents were either obtained from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μM) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Analytical Methods

Reverse Phase High Performance Liquid Chromatography:

Analytical HPLC was carried out using a Waters Xselect CSH C18, 2.5 μm, 4.6×30 mm column eluting with a gradient of 0.1% Formic Acid in MeCN in 0.1% aqueous Formic Acid; a Waters Xbridge BEH C18, 2.5 μm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid (Method 1); a Waters Xbridge BEH C18, 2.5 μm, 4.6×30 mm column eluting with a gradient of MeCN in aqueous 10 mM Ammonium Bicarbonate (Method 2). UV and mass spectra of the eluted peaks were measured using a variable wavelength detector on either an Agilent 1200 with or an Agilent Infinity 1260 LCMS with 6120 single quadrupole mass spectrometer with positive and negative ion electrospray. Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 μm, 19×50 mm column using a gradient MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters FractionLynx LCMS.

1H NMR Spectroscopy: 1H NMR spectra were acquired on a Bruker Avance III spectrometer at 400 MHz. Either the central peaks of chloroform-d, dimethylsulfoxide-d6 or an internal standard of tetramethylsilane were used as references.

$^1$H NMR Spectroscopy:

$^1$H NMR spectra were acquired on a Bruker Avance III spectrometer at 400 MHz using residual undeuterated solvent as reference

Reference Examples: Preparation of Chiral Intermediates (Chiral (R)- and (S)-3-aryl-2-methylpropanoic acids) via Routes C, D(i) and D(ii)

(R)-3-(3-(4-chlorophenyl)propanoyl)-4-isopropyloxazolidin-2-one

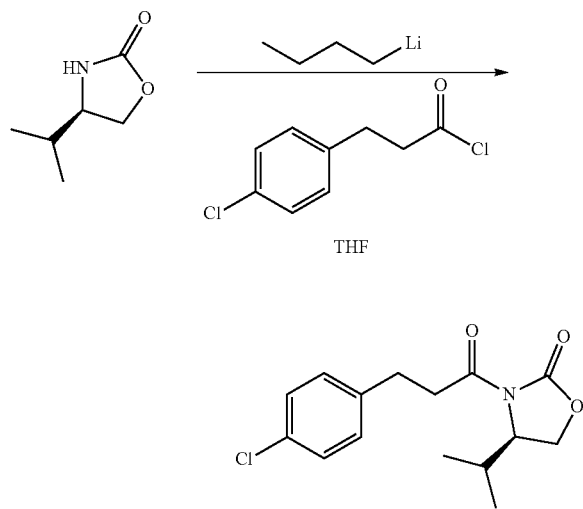

To a solution of 3-(4-chlorophenyl)propanoic acid (5 g, 27.1 mmol) in THF (100 mL) under nitrogen at RT was added dropwise oxalyl chloride (7.11 mL, 81.0 mmol). When the addition was complete a drop of DMF was added and the reaction mixture was stirred for 1.5 hrs. The solvent was removed in vacuo to afford crude 3-(4-chlorophenyl) propanoyl chloride, which was used in the following (assuming 100% yield):

A solution of (R)-4-isopropyloxazolidin-2-one (3.24 g, 25.1 mmol) in THF (100 mL) was cooled to −78° C. N-Butyllithium (10.23 mL, 25.6 mmol) was added dropwise. When the addition was complete crude 3-(4-chlorophenyl) propanoyl chloride (5.5 g, 27.1 mmol) in THF (8 mL) was added dropwise. The CO$_2$/acetone bath was left in place and the reaction mixture was left to warm to rt over 18 hrs. Saturated ammonium chloride (30 mL) was added to the reaction mixture. After stirring for 10 mins the solvent was removed in vacuo and the residue was partitioned between DCM (300 mL) and water (100 mL). The organic phase was collected and washed with brine (2×100 mL), then passed through a phase sep cartridge. The solvent was removed in vacuo and the crude product was purified by chromatography (120 g silica, 0-100% EtOAc in isohexanes, gradient elution) to afford (R)-3-(3-(4-chlorophenyl) propanoyl)-4-isopropyloxazolidin-2-one (5.25 g, 17.75 mmol, 70.8% yield) as a white crystalline solid; Rt 2.55 min (Method 1), m/z 296 (M+H)+(ES+).

(R)-3-((R)-3-(4-chlorophenyl)-2-methylpropanoyl)-4-isopropyloxazolidin-2-one

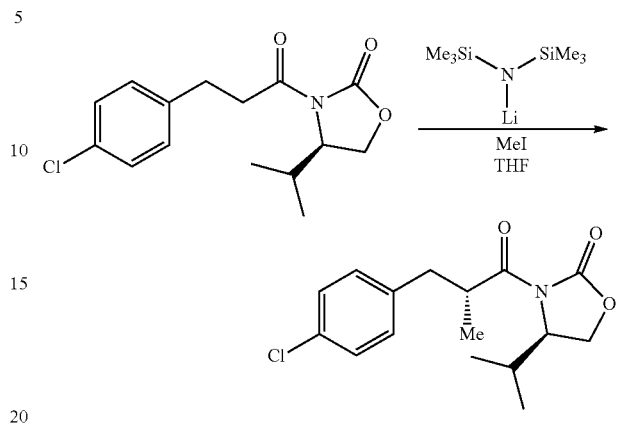

A solution of (R)-3-(3-(4-chlorophenyl)propanoyl)-4-isopropyloxazolidin-2-one (0.5 g, 1.691 mmol) in THF (10 mL) was cooled to −78° C. Lithium bis(trimethylsilyl)amide (2.03 mL, 2.029 mmol) was added dropwise. When the addition was complete the reaction mixture was stirred at −78° C. for 30 mins. Methyl iodide (0.53 mL, 8.45 mmol) was added dropwise and the reaction mixture warmed to RT over 18 hrs. The reaction mixture was quenched with the addition of water (10 mL), then partitioned between EtOAc (100 mL) and water (30 mL). The aqueous phase was extracted with EtOAc (50 mL). Combined organics were dried (sodium sulfate) and passed through a phase sep column. The solvents were removed in vacuo and the residue purified by chromatography (40 g silica, 10-100% ether in isohexanes, gradient elution) to afford (R)-3-((R)-3-(4-chlorophenyl)-2-methylpropanoyl)-4-isopropyl oxazolidin-2-one (158 mg, 0.510 mmol, 30.2% yield) as a clear oil; Rt 2.70 min (Method 1), m/z 310/312 (M+H)+(ES+).

(R)-3-(4-chlorophenyl)-2-methylpropanoic acid

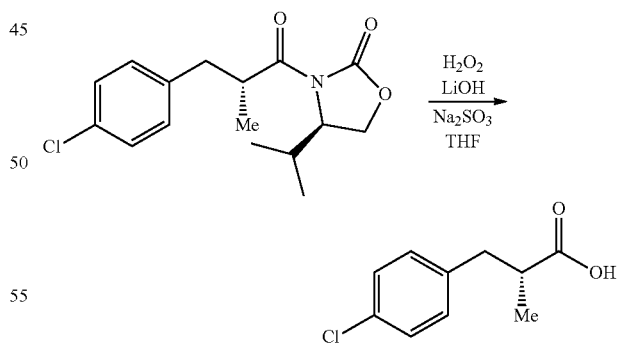

To a cold (0° C.) solution of (R)-3-((R)-3-(4-chlorophenyl)-2-methylpropanoyl)-4-isopropyl oxazolidin-2-one (144 mg, 0.47 mmol) in THF (6 mL) and water (2 mL) was added hydrogen peroxide, 35 wt % aq solution (2.04 mL, 23.24 mmol). After stirring for 2 minutes lithium hydroxide, 1M solution (1.63 mL, 1.63 mmol) was added and the reaction left to warm to RT over 18 hrs. After recooling in an icebath, water (30 mL) was added and then sodium sulfite was added portionwise. After stirring for 5 mins between each portion the reaction was checked for excess hydrogen peroxide (starch iodide paper). When no excess oxidant was present the organic solvent was removed in vacuo. The aqueous residue was extracted with DCM (2×50 mL) then acidified to pH1 with the addition of 1M HCl (~30 mL). The acidic aqueous solution was extracted with EtOAc (3×100 mL). Combined organics were dried (MgSO4) then passed through a phase sep cartridge. The solvents were removed in vacuo to afford (R)-3-(4-chlorophenyl)-2-methylpropanoic acid (87 mg, 0.429 mmol, 92% yield) as a colourless oil; Rt 2.06 min (Method 1), m/z 197/199 (M−H)−(ES).

(S)-3-(3-(4-chlorophenyl)propanoyl)-4-isopropyloxazolidin-2-one

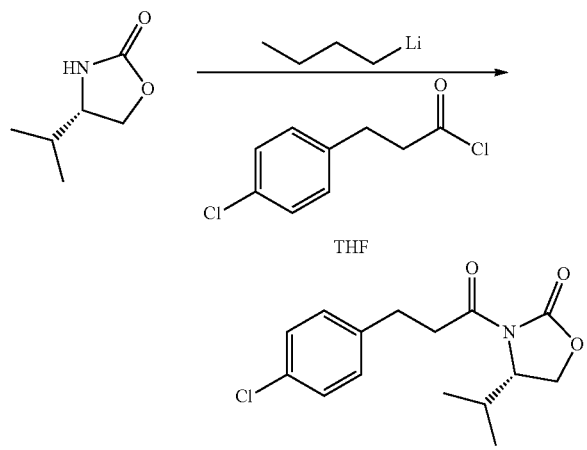

To a solution of 3-(4-chlorophenyl)propanoic acid (5 g, 27.1 mmol) in THF (100 mL) under nitrogen at RT was added dropwise oxalyl chloride (7.11 mL, 81.0 mmol). When the addition was complete a drop of DMF was added and the reaction mixture stirred for 1.5 hrs. The solvent was removed in vacuo to afford crude 3-(4-chlorophenyl)propanoyl chloride, which was used in the following (assuming 100% yield):
A solution of (S)-4-isopropyloxazolidin-2-one (3.24 g, 25.1 mmol) in THF (100 mL) was cooled to −78° C. N-Butyl-ithium (10.23 mL, 25.6 mmol) was added dropwise. When the addition was complete crude 3-(4-chlorophenyl)pro-panoyl chloride (5.5 g, 27.1 mmol) in THF (8 mL) was added dropwise. The CO2/acetone bath was left in place and the reaction mixture was left to warm to rt over 18 hrs. Saturated ammonium chloride (30 mL) was added to the reaction mixture. After stirring for 10 mins the solvent was removed in vacuo and the residue was partitioned between DCM (300 mL) and water (100 mL). The organic phase was collected and washed with brine (2×100 mL), then passed through a phase sep cartridge. The solvent was removed in vacuo and the crude product was purified by chromatography (120 g silica, 0-100% EtOAc in isohexanes, gradient elution) to afford (S)-3-(3-(4-chlorophenyl) propanoyl)-4-isopropyloxazolidin-2-one (6.42 g, 21.71 mmol, 87.0% yield) as a white crystalline solid; Rt 2.54 min (Method 1), m/z 296/298 (M+H)+(ES+).

(S)-3-((S)-3-(4-chlorophenyl)-2-methylpropanoyl)-4-isopropyloxazolidin-2-one

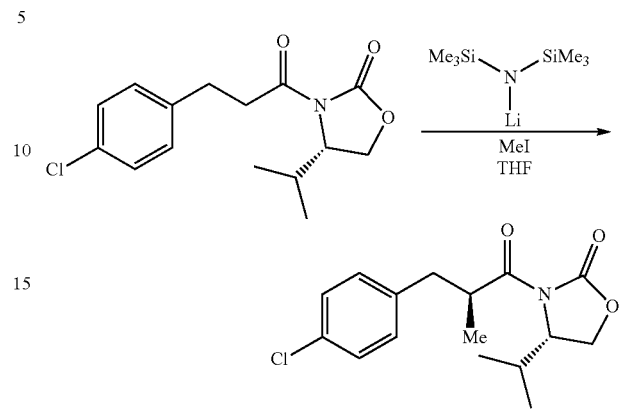

A solution of (S)-3-(3-(4-chlorophenyl)propanoyl)-4-iso-propyloxazolidin-2-one (1.0 g, 3.38 mmol) in THF (20 mL) was cooled to −78° C. Lithium bis(trimethylsilyl)amide (4.06 mL, 4.06 mmol) was added dropwise. When the addition was complete the reaction mixture was stirred at −78° C. for 30 mins. Methyl iodide (1.06 mL, 16.91 mmol) was added dropwise and the reaction mixture warmed to RT over 18 hrs. The reaction mixture was quenched with the addition of water (20 mL), then partitioned between EtOAc (200 mL) and water (60 mL). The aqueous phase was extracted with EtOAc (100 mL). Combined organics were dried (sodium sulfate) and passed through a phase sep column. The solvents were removed in vacuo and the residue purified by chromatography (80 g silica, 10-100% ether in isohexanes, gradient elution) to afford (S)-3-((S)-3-(4-chlorophenyl)-2-methylpropanoyl)-4-isopropyl oxazoli-din-2-one (478 mg, 1.53 mmol, 45.2% yield) as a clear oil; Rt 2.69 min (Method 1), m/z 310/312 (M+H)+(ES+).

(S)-3-(4-chlorophenyl)-2-methylpropanoic acid

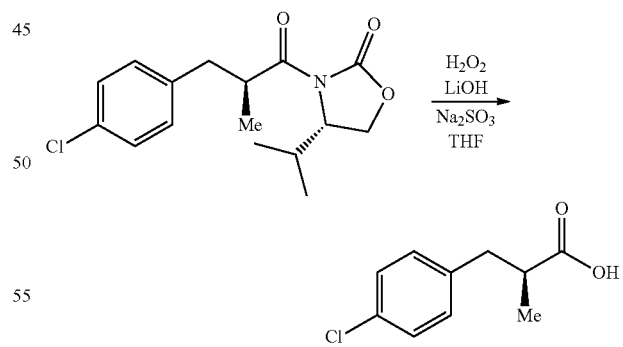

To a cold (0° C.) solution of (S)-3-((S)-3-(4-chlorophe-nyl)-2-methylpropanoyl)-4-isopropyl oxazolidin-2-one (460 mg, 1.49 mmol) in THF (18 mL) and water (6 mL) was added hydrogen peroxide, 35 wt % aq solution (6.50 mL, 74.20 mmol). After stirring for 2 minutes lithium hydroxide, 1M solution (5.20 mL, 5.20 mmol) was added and the reaction left to warm to RT over 18 hrs. After recooling in an icebath, water (90 mL) was added and then sodium sulfite was added portionwise. After stirring for 5 mins between each portion the reaction was checked for excess hydrogen peroxide (starch iodide paper). When no excess oxidant was present the organic solvent was removed in vacuo. The aqueous residue was extracted with DCM (2×100 mL) then acidified to pH1 with the addition of 1M HCl (~65 mL). The acidic aqueous solution was extracted with EtOAc (3×100 mL). Combined organics were dried (MgSO₄) then passed through a phase sep cartridge. The solvents were removed in vacuo to afford (S)-3-(4-chlorophenyl)-2-methylpropanoic acid (280 mg, 1.37 mmol, 92% yield) as a colourless oil; Rt 2.06 min (Method 1), m/z 197/199 (M−H)⁻ (ES⁻).

(R)-3-(3-(4-chloro-3-fluorophenyl)propanoyl)-4-isopropyloxazolidin-2-one

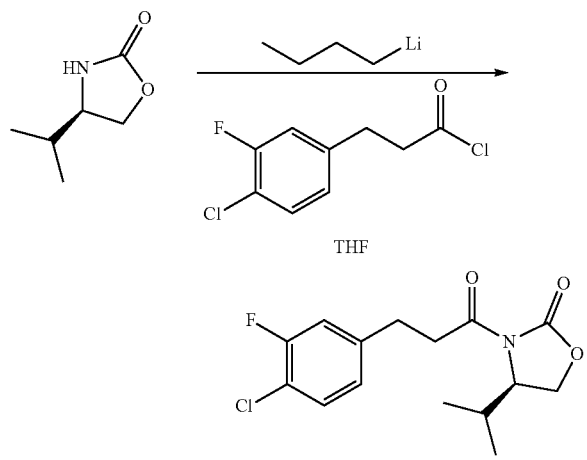

To a solution of 3-(4-chloro-3-fluorophenyl)propanoic acid (7.17 g, 35.4 mmol) in dry DCM (100 mL) under nitrogen at RT was added dropwise oxalyl chloride (6.20 mL, 70.8 mmol). When the addition was complete a drop of DMF was added and the reaction mixture stirred for 1.5 hrs. The solvent was removed in vacuo and the residue azeotroped with toluene to afford crude 3-(4-chloro-3-fluorophenyl)propanoyl chloride, which was used in the following (assuming 100% yield):

A solution of (R)-4-isopropyloxazolidin-2-one (4.57 g, 35.4 mmol) in THF (100 mL, 35.4 mmol) was cooled to −78° C. n-Butyllithium (15.57 mL, 38.9 mmol) was added dropwise. When the addition was complete, crude 3-(4-chloro-3-fluorophenyl)propanoyl chloride (7.82 g, 35.4 mmol) in THF (8 mL) was added dropwise. The CO2/acetone bath was left in place and the reaction mixture was left to warm to rt over 18 hrs. Saturated ammonium chloride (30 mL) was added to the reaction mixture. After stirring for 10 mins the solvents were removed in vacuo and the residue was partitioned between DCM (300 mL) and water (100 mL). The organic phase was collected and washed with brine (2×100 mL), then passed through a phase sep cartridge. The solvent was removed in vacuo and the crude product purified by chromatography (120 g silica, 0-100% EtOAc in isohexanes, gradient elution) to afford (R)-3-(3-(4-chloro-3-fluorophenyl)propanoyl)-4-isopropyloxazolidin-2-one (7.52 g, 23.48 mmol, 66.4% yield) as a pale yellow solid; Rt 2.55 min (Method 1), m/z 313/315 (M+H)+(ES+).

(R)-3-((R)-3-(4-chloro-3-fluorophenyl)-2-methylpropanoyl)-4-isopropyloxazolidin-2-one

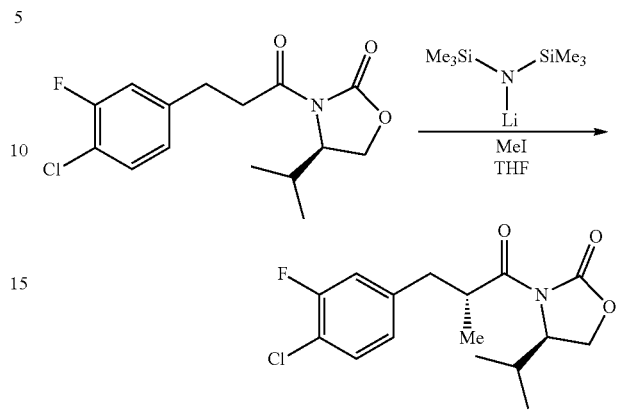

A solution of (R)-3-(3-(4-chloro-3-fluorophenyl)propanoyl)-4-isopropyloxazolidin-2-one (8.34 g, 26.6 mmol) in THF (100 mL) was cooled to −78° C. Lithium bis(trimethylsilyl)amide (31.9 mL, 31.9 mmol) was added dropwise. When the addition was complete the reaction mixture was stirred at −78° C. for 60 mins. Methyl iodide (4.16 mL, 66.5 mmol) was added dropwise and the reaction mixture left at −78° C. for 1 hr before warming to RT over 24 hrs. The reaction mixture was quenched with the addition of water (20 mL), then partitioned between EtOAc (200 mL) and water (60 mL). The aqueous phase was extracted with EtOAc (100 mL). Combined organics were dried (sodium sulfate), filtered and evaporated under reduced pressure. The crude product was purified by chromatography (120 g silica, 10-100% ether in isohexanes, gradient elution) to afford (R)-3-((R)-3-(4-chloro-3-fluorophenyl)-2-methylpropanoyl)-4-isopropyloxazolidin-2-one (5.40 g, 16.15 mmol, 60.7% yield) as a waxy yellow solid. Rt 2.69 min (Method 1), m/z 327/329 (M+H)+(ES+).

(R)-3-(4-chloro-3-fluorophenyl)-2-methylpropanoic acid

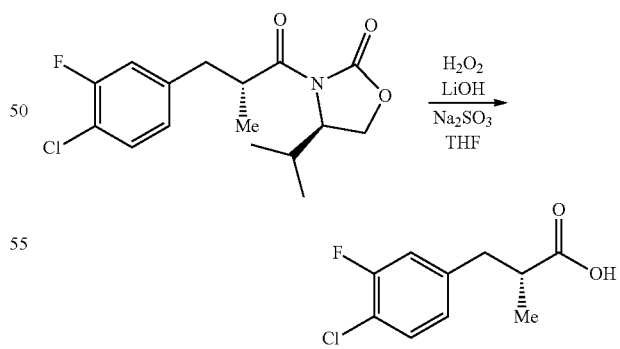

To a cold (0° C.) solution of (R)-3-((R)-3-(4-chloro-3-fluorophenyl)-2-methylpropanoyl)-4-isopropyloxazolidin-2-one (5.401 g, 16.48 mmol) in THF (200 mL) and water (60 mL) was added hydrogen peroxide, 30 wt % aq solution (67.3 mL, 659 mmol). After stirring for 2 minutes lithium hydroxide, 1M solution (57.7 mL, 57.7 mmol) was added and the reaction left to warm to RT over 18 hrs. After recooling in an icebath, water (100 mL) was added and then sodium sulfite was added portionwise. After stirring for 5 mins between each portion the reaction was checked for excess hydrogen peroxide (starch iodide paper). When no excess oxidant was present the organic solvent was removed in vacuo. The aqueous residue was extracted with EtOAc (2×150 mL) then acidified to pH with the addition of 1M HCl (~100 mL). The acidic aqueous solution was extracted with EtOAc (3×200 mL). Combined organics were dried (MgSO4), filtered and the solvents removed in vacuo to afford an oil. The crude product was purified by chromatography (80 g silica, 0-70% EtOAc/isohexane, gradient elution) to afford (R)-3-(4-chloro-3-fluorophenyl)-2-methylpropanoic acid (3.34 g, 14.49 mmol, 88% yield) as a pale yellow oil; Rt 2.09 min (Method 1), m/z 215/217 (M_H)–(ES).

(S)-3-(3-(4-chloro-3-fluorophenyl)propanoyl)-4-isopropyloxazolidin-2-one

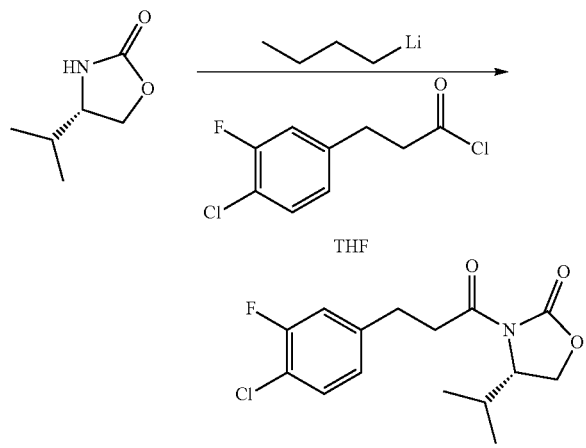

To a solution of 3-(4-chloro-3-fluorophenyl)propanoic acid (7.17 g, 35.4 mmol) in dry DCM (100 mL) under nitrogen at RT was added dropwise oxalyl chloride (6.20 mL, 70.8 mmol). When the addition was complete a drop of DMF was added and the reaction mixture stirred for 1.5 hrs. The solvent was removed in vacuo and the residue azeotroped with toluene to afford crude 3-(4-chloro-3-fluorophenyl)propanoyl chloride, which was used in the following (assuming 100% yield):

A solution of (S)-4-isopropyloxazolidin-2-one (4.57 g, 35.4 mmol) in THF (100 mL, 35.4 mmol) was cooled to −78° C. n-Butyllithium (15.57 mL, 38.9 mmol) was added dropwise. When the addition was complete, crude 3-(4-chloro-3-fluorophenyl)propanoyl chloride (7.82 g, 35.4 mmol) in THF (8 mL) was added dropwise. The CO2/acetone bath was left in place and the reaction mixture was left to warm to rt over 18 hrs. Saturated ammonium chloride (30 mL) was added to the reaction mixture. After stirring for 10 mins the solvents were removed in vacuo and the residue was partitioned between DCM (300 mL) and water (100 mL). The organic phase was collected and washed with brine (2×100 mL), then passed through a phase sep cartridge. The solvent was removed in vacuo and the crude product purified by chromatography (120 g silica, 0-100% EtOAc in isohexanes, gradient elution) to afford (S)-3-(3-(4-chloro-3-fluorophenyl)propanoyl)-4-isopropyloxazolidin-2-one (6.16 g, 16.88 mmol, 47.7% yield) as a white solid; Rt 2.55 min (Method 1), m/z 313/315 (M+H)+(ES+).

(S)-3-((S)-3-(4-chloro-3-fluorophenyl)-2-methylpropanoyl)-4-isopropyloxazolidin-2-one

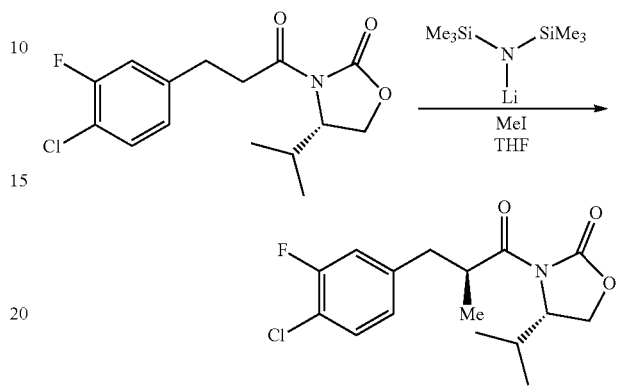

A solution of (S)-3-(3-(4-chloro-3-fluorophenyl)propanoyl)-4-isopropyloxazolidin-2-one (7.37 g, 23.5 mmol) in THF (100 mL) was cooled to −78° C. Lithium bis(trimethylsilyl)amide (28.2 mL, 28.2 mmol) was added dropwise. When the addition was complete the reaction mixture was stirred at −78° C. for 60 mins. Methyl iodide (3.67 mL, 58.7 mmol) was added dropwise and the reaction mixture left at −78° C. for 1 hr before warming to RT over 24 hrs. The reaction mixture was quenched with the addition of water (20 mL), then partitioned between EtOAc (200 mL) and water (60 mL). The aqueous phase was extracted with EtOAc (100 mL). Combined organics were dried (sodium sulfate), filtered and evaporated under reduced pressure. The crude product was purified by chromatography (120 g silica, 10-100% ether in isohexanes, gradient elution) to afford (S)-3-((S)-3-(4-chloro-3-fluorophenyl)-2-methylpropanoyl)-4-isopropyloxazolidin-2-one (4.92 g, 14.26 mmol, 60.7% yield) as a waxy yellow solid. Rt 2.72 min (Method 1), m/z 327/329 (M+H)+(ES+).

(S)-3-(4-chloro-3-fluorophenyl)-2-methylpropanoic acid

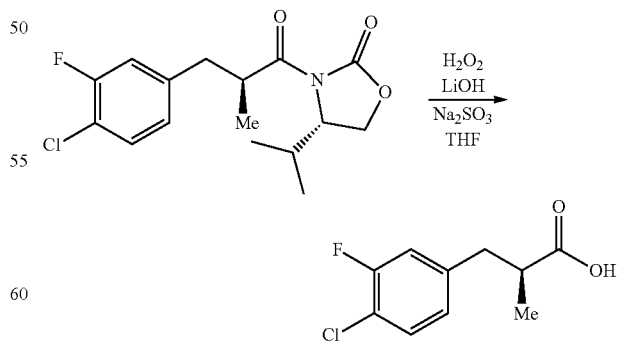

To a cold (0° C.) solution of (S)-3-((S)-3-(4-chloro-3-fluorophenyl)-2-methylpropanoyl)-4-isopropyloxazolidin-2-one (4.92 g, 15.01 mmol) in THF (200 mL) and water (60 mL) was added hydrogen peroxide, 30 wt % aq solution (61.3 mL, 600 mmol). After stirring for 2 minutes lithium hydroxide, 1M solution (52.5 mL, 52.5 mmol) was added and the reaction left to warm to RT over 18 hrs. After recooling in an icebath, water (100 mL) was added and then sodium sulfite was added portionwise. After stirring for 5 mins between each portion the reaction was checked for excess hydrogen peroxide (starch iodide paper). When no excess oxidant was present the organic solvent was removed in vacuo. The aqueous residue was extracted with EtOAc (2×150 mL) then acidified to pH1 with the addition of 1M HCl (~100 mL). The acidic aqueous solution was extracted with EtOAc (3×200 mL). Combined organics were dried (MgSO4), filtered and the solvents removed in vacuo to afford an oil. The crude product was purified by chromatography (80 g silica, 0-70% EtOAc/isohexane, gradient elution) to afford (S)-3-(4-chloro-3-fluorophenyl)-2-methylpropanoic acid (3.04 g, 13.47 mmol, 90% yield) as a pale yellow oil; Rt 2.10 min (Method 1), m/z 215/217 (M_H)−(ES).

Ethyl (E/Z)-3-(3-fluoro-4-(trifluoromethoxy)phenyl)acrylate

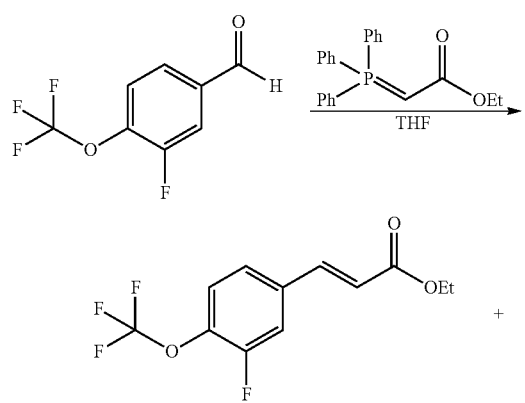

Ethyl 2-(triphenylphosphoranylidene)acetate (23.44 g, 67.3 mmol) and 3-fluoro-4-(trifluoromethoxy)benzaldehyde (10 g, 48.1 mmol) in dry THF (300 mL, 6102 mmol) was heated to 60° C. for 2 hrs. The solvent was removed in vacuo, the residue triturated with ether (500 mL) and filtered. The filtrate was evaporated under reduced pressure to afford a pale yellow solid, which was purified by chromatography (330 g silica, 0-50% diethyl ether in isohexanes) to afford (E/Z)-ethyl 3-(3-fluoro-4-(trifluoromethoxy)phenyl)acrylate (12.17 g, 43.7 mmol, 91% yield) as a pale colourless oil. Rt 2.68 min (Method 1), m/z 279 (M+H)+(ES+).

Ethyl 3-(3-fluoro-4-(trifluoromethoxy)phenyl)propanoate

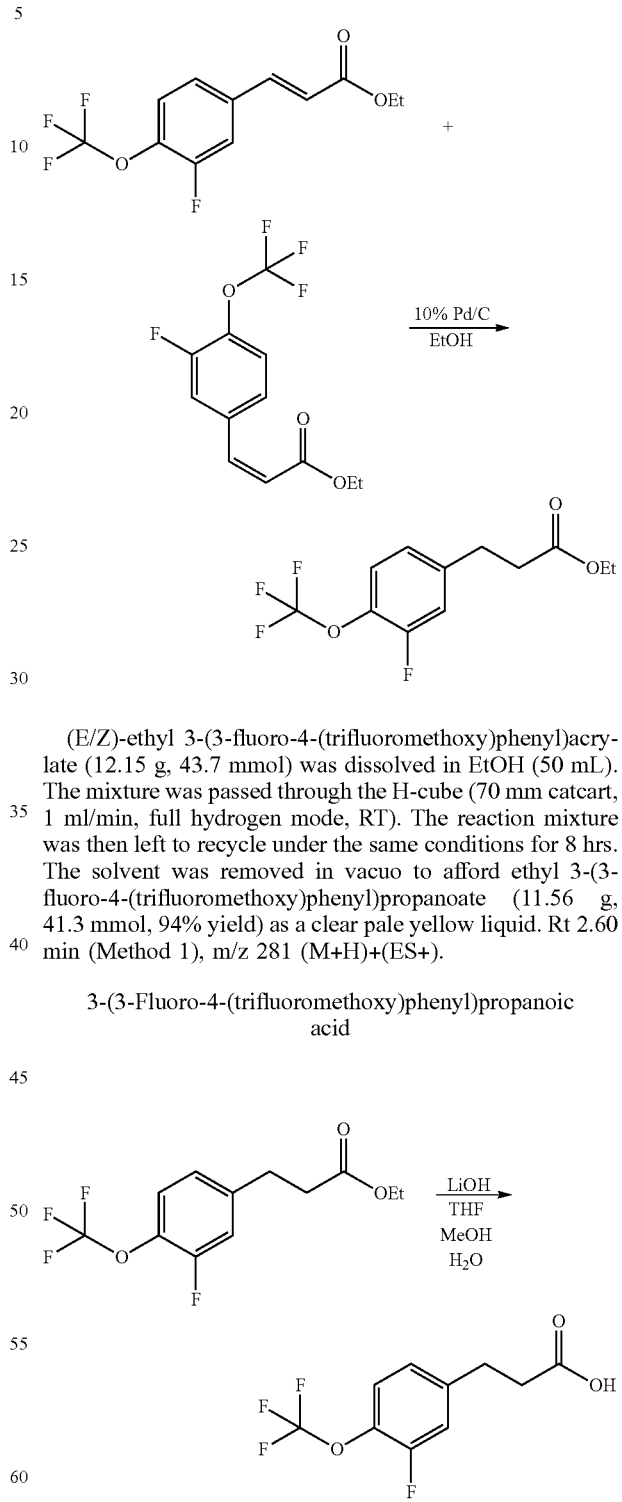

(E/Z)-ethyl 3-(3-fluoro-4-(trifluoromethoxy)phenyl)acrylate (12.15 g, 43.7 mmol) was dissolved in EtOH (50 mL). The mixture was passed through the H-cube (70 mm catcart, 1 ml/min, full hydrogen mode, RT). The reaction mixture was then left to recycle under the same conditions for 8 hrs. The solvent was removed in vacuo to afford ethyl 3-(3-fluoro-4-(trifluoromethoxy)phenyl)propanoate (11.56 g, 41.3 mmol, 94% yield) as a clear pale yellow liquid. Rt 2.60 min (Method 1), m/z 281 (M+H)+(ES+).

3-(3-Fluoro-4-(trifluoromethoxy)phenyl)propanoic acid

To a solution of ethyl 3-(3-fluoro-4-(trifluoromethoxy)phenyl)propanoate (11.56 g, 41.3 mmol) in THF (200 mL) was added lithium hydroxide, 1M soln (83 mL, 83 mmol). Methanol (50 mL) was added and the reaction mixture was stirred at RT for 18 hrs. The organic solvent was removed in vacuo and the remaining aqueous phase was acidified to pH1 with the addition of 6M HCl. The solution was extracted with ethyl acetate (2×250 mL). Combined organics were dried (MgSO4) and collected via phase sep cartridge. The solvent was removed in vacuo to afford 3-(3-fluoro-4-(trifluoromethoxy) phenyl)propanoic acid (10.19 g, 39.6 mmol, 96% yield) as a light yellow solid. Rt 2.15 min (Method 1), m/z 251 (M_H)–(ES).

(R)-3-(3-(3-fluoro-4-(trifluoromethoxy)phenyl)propanoyl)-4-isopropyloxazolidin-2-one

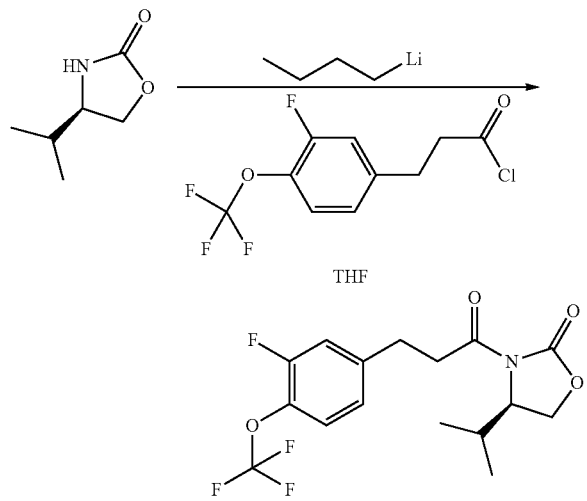

To a solution of 3-(3-fluoro-4-(trifluoromethoxy)phenyl) propanoic acid (10.18 g, 40.4 mmol) in dry THF (200 mL) under nitrogen at RT was added dropwise oxalyl chloride (10.60 mL, 121 mmol). When the addition was complete a drop of DMF was added and the reaction mixture stirred for 1.5 hrs. The solvent was removed in vacuo to afford crude 3-(3-fluoro-4-(trifluoromethoxy)phenyl)propanoyl chloride, which was used in the following (assuming 100% yield):

A solution of (R)-4-isopropyloxazolidin-2-one (2.60 g, 20.14 mmol) in THF (100 mL) was cooled to −78° C. N-Butyllithium (8.22 mL, 20.54 mmol) was added dropwise. When the addition was complete crude 3-(3-fluoro-4-(trifluoromethoxy)phenyl)propanoyl chloride (5.45 g, 20.14 mmol) in THF (10 mL) was added dropwise. The CO2/acetone bath was left in place and the reaction mixture was left to warm to rt over 18 hrs. Saturated ammonium chloride (30 mL) was added to the reaction mixture. After stirring for 10 mins the solvent was removed in vacuo and the residue was partitioned between EtOAc (300 mL) and water (100 mL). The organic phase was collected and washed with brine (2×100 mL), then left to stand for 48 h. The organic solution was dried (MgSO4), then passed through a phase sep cartridge. The solvent was removed in vacuo and the crude product purified by chromatography (120 g silica, 0-100% EtOAc in isohexanes, gradient elution) to afford (R)-3-(3-(3-fluoro-4-(trifluoromethoxy)phenyl)propanoyl)-4-isopropyloxazolidin-2-one (5.94 g, 14.71 mmol, 73.1% yield) as a white crystalline solid. Rt 2.68 min (Method 1), m/z no mass ions (M+H)+(ES+); 1H NMR (400 MHz, DMSO-d6) δ 7.51-7.35 (m, 2H), 7.21 (ddd, J=8.5, 2.1, 1.1 Hz, 1H), 4.42-4.20 (m, 3H), 3.27 (ddd, J=17.3, 8.3, 6.8 Hz, 1H), 3.09 (dt, J=17.3, 7.3 Hz, 1H), 2.92 (td, J=7.3, 2.7 Hz, 2H), 2.13 (hd, J=7.0, 3.8 Hz, 1H), 0.84 (d, J=7.1 Hz, 3H), 0.75 (d, J=6.8 Hz, 3H).

(R)-3-((R)-3-(3-fluoro-4-(trifluoromethoxy)phenyl)-2-methylpropanoyl)-4-isopropyl oxazolidin-2-one

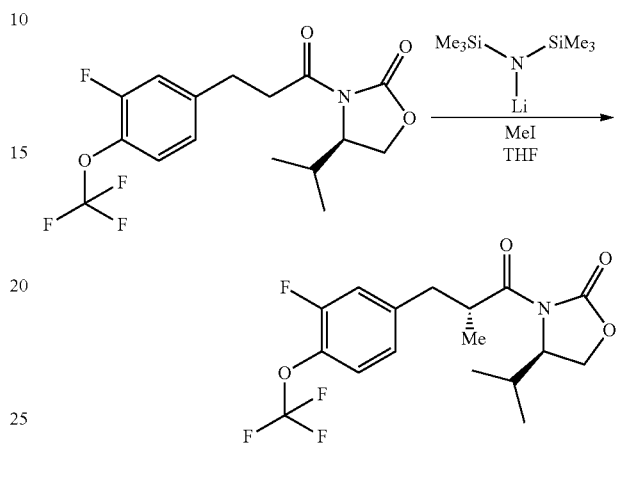

A solution of (R)-3-(3-(3-fluoro-4-(trifluoromethoxy) phenyl)propanoyl)-4-isopropyloxazolidin-2-one (1 g, 2.75 mmol) in THF (20 mL) was cooled to −78° C. lithium bis(trimethylsilyl)amide (3.30 mL, 3.30 mmol) was added dropwise. When the addition was complete the reaction mixture was stirred at −78° C. for 30 mins. Methyl iodide (0.861 mL, 13.76 mmol) was added dropwise and the reaction mixture left to warm to RT over 18 hrs. The reaction mixture was quenched with the addition of water (20 mL, then partitioned between EtOAc (200 mL) and water (60 mL). The aqueous phase was extracted with EtOAc (100 mL). Combined organics were dried (sodium sulfate) and passed through a phase sep column. The solvent was removed in vacuo and the residue purified by chromatography (24 g silica, 10-100% ether in isohexanes, gradient elution) to afford (R)-3-((R)-3-(3-fluoro-4-(trifluoromethoxy) phenyl)-2-methylpropanoyl)-4-isopropyloxazolidin-2-one (570 mg, 1.511 mmol, 54.9% yield) as an oil. 1H NMR (400 MHz, DMSO-d6) δ 7.47 (tq, J=8.4, 1.2 Hz, 1H), 7.35 (dd, J=11.6, 2.0 Hz, 1H), 7.16 (ddd, J=8.5, 2.0, 1.1 Hz, 1H), 4.41-4.31 (m, 1H), 4.31-4.21 (m, 2H), 3.92 (dt, J=7.6, 6.7 Hz, 1H), 3.03-2.95 (m, 1H), 2.66 (dd, J=13.6, 7.7 Hz, 1H), 2.17 (pd, J=6.9, 3.9 Hz, 1H), 1.10 (d, J=6.9 Hz, 3H), 0.82 (dd, J=23.4, 7.0 Hz, 6H).

(R)-3-(3-fluoro-4-(trifluoromethoxy)phenyl)-2-methylpropanoic acid

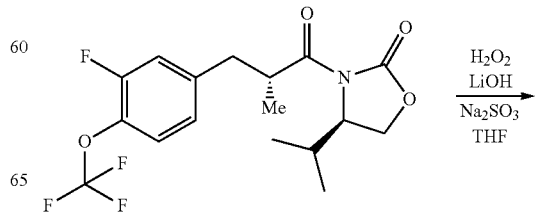

-continued

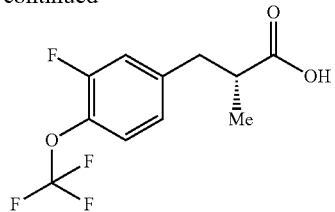

To a cold (0° C.) solution of (R)-3-((R)-3-(3-fluoro-4-(trifluoromethoxy)phenyl)-2-methyl propanoyl)-4-isopropyloxazolidin-2-one (1.28 g, 3.39 mmol) in THF (60 mL) and water (20 mL) was added hydrogen peroxide, 35 wt % aq solution (14.85 ml, 170 mmol). After stirring for 2 minutes lithium hydroxide, 1M solution (11.87 ml, 11.87 mmol) was added and the reaction left to warm to RT over 18 hrs. After recooling in an icebath, water (100 mL) was added and then sodium sulfite was added portionwise. After stirring for 5 mins between each portion the reaction was checked for excess hydrogen peroxide (starch iodide paper). When no excess oxidant was present the organic solvent was removed in vacuo. The aqueous residue was extracted with EtOAc (2×150 mL) then acidified to pH1 with the addition of 1M HCl (~30 mL). The acidic aqueous solution was extracted with EtOAc (2×150 mL). Combined organics were dried (MgSO4), filtered and the solvents were removed in vacuo to afford (R)-3-(3-fluoro-4-(trifluoromethoxy)phenyl)-2-methylpropanoic acid (1.05 g, 3.91 mmol, 115% yield) as a colourless oil. Rt 2.26 min (Method 1), m/z 265 (M_H)− (ES).

Example 1: 4-(2-(1-(3-fluoro-4-methoxyphenyl) propan-2-yl)-1-(1-methylpyrrolidin-3-yl)-1H-benzo [d]imidazol-5-yl)-3,5-dimethylisoxazole N-(4-(3,5-dimethylisoxazol-4-yl)-2-nitrophenyl)-1-methylpyrrolidin-3-amine

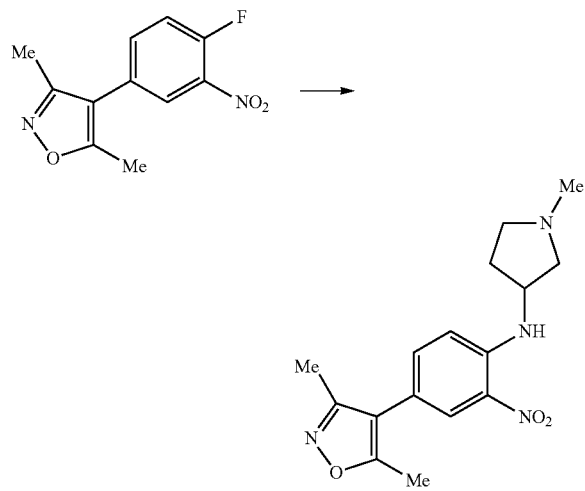

4-(4-fluoro-3-nitrophenyl)-3,5-dimethylisoxazole (1.1 g, 4.42 mmol) was dissolved in dry THF (12 mL, 146 mmol) under nitrogen, TEA (1.233 mL, 8.85 mmol) was added, followed by 1-methylpyrrolidin-3-amine (0.665 g, 6.64 mmol) and the reaction mixture stirred at RT for 2.5 days. The reaction mixture was poured onto ice water (60 mL), extracted with EtOAc (2×60 mL), the combined organics washed with brine (30 mL), dried over MgSO4, filtered and concentrated in vacuo. The crude product was loaded onto a column of SCX (15 g) in MeOH. The column was washed with MeOH and then the product was eluted with 0.7 M ammonia in MeOH. The resultant mixture was concentrated in vacuo to afford N-(4-(3,5-dimethylisoxazol-4-yl)-2-nitrophenyl)-1-methylpyrrolidin-3-amine as an orange oil (1.26 g, 81%) and used in the next step without further manipulation; Rt 1.06 min (method 1); m/z 317 (M+H)+(ES+).

4-(3,5-dimethylisoxazol-4-yl)-N1-(1-methylpyrrolidin-3-yl)benzene-1,2-diamine

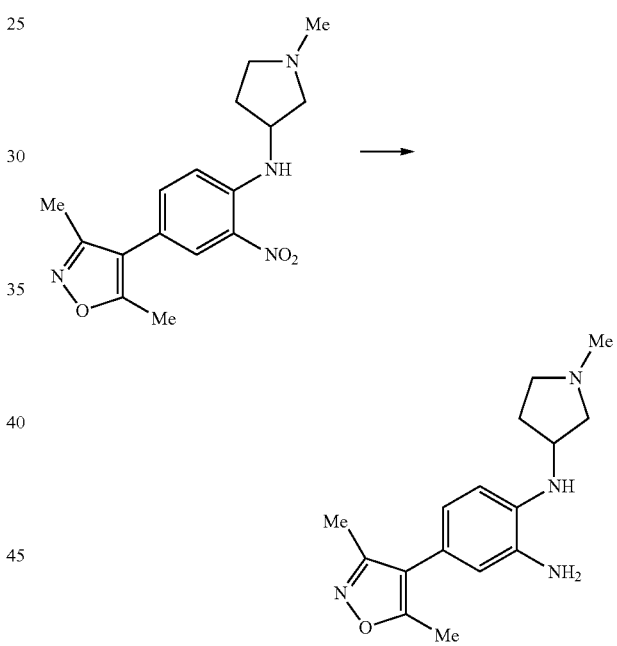

N-(4-(3,5-dimethylisoxazol-4-yl)-2-nitrophenyl)-1-methylpyrrolidin-3-amine (1.26 g, 3.58 mmol) and aqueous concentrated ammonia (2.79 mL, 71.7 mmol) were dissolved in THF (45 mL, 549 mmol) and water (45 mL, 2498 mmol), sodium dithionite (6.24 g, 35.8 mmol) were added and the reaction mixture stirred at RT for 2 h. Further concentrated ammonia (1.396 mL, 35.8 mmol) and sodium dithionite (3.12 g, 17.92 mmol) were added and the reaction mixture stirred at RT for 1 h. The phases were separated, the aqueous extracted with EtOAc (30 mL), the combined organics washed with brine (30 mL), dried over MgSO4, filtered and concentrated in vacuo to give 4-(3,5-dimethylisoxazol-4-yl)-N1-(1-methylpyrrolidin-3-yl)benzene-1,2-diamine as a pink-red oil (1.06 g, 76%); m/z 463 (M+H)+(ES+).

4-(2-(1-(3-fluoro-4-methoxyphenyl)propan-2-yl)-1-(1-methylpyrrolidin-3-yl)-1H-benzo[d]imidazol-5-yl)-3,5-dimethylisoxazole

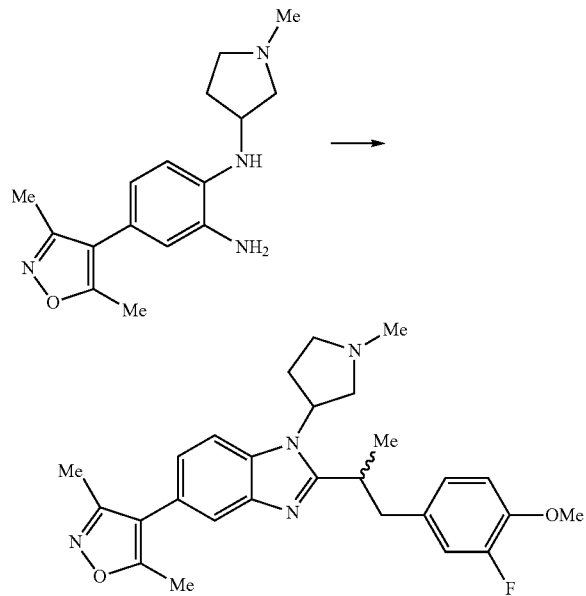

A mixture of 4-(3,5-dimethylisoxazol-4-yl)-N1-(1-methylpyrrolidin-3-yl)benzene-1,2-diamine (100 mg, 0.35 mmol), 3-(3-fluoro-4-methoxyphenyl)-2-methylpropanoic acid (97 mg, 0.455 mmol), HATU (173 mg, 0.455 mmol), DIPEA (202 µl, 1.155 mmol) in DMF (1750 µl, 0.350 mmol) was stirred overnight. The mixture was diluted with EtOAc (2 mL) and water (2 mL). The layers were separated and the organic layer was washed with water (3×2 mL), dried (MgSO₄), filtered and reduced in vacuo. The residue was dissolved in AcOH (2 mL) and then heated at 80° C. overnight. The mixture was cooled to room temperature, evaporated in vacuo and the residue azeotropped with toluene. The crude product was purified by chromatography on the Companion (12 g column, 0-10% MeOH/DCM) to afford 4-(2-(1-(3-fluoro-4-methoxyphenyl)propan-2-yl)-1-(1-methylpyrrolidin-3-yl)-1H-benzo[d]imidazol-5-yl)-3,5-dimethylisoxazole 1 (32 mg, 20%) as a white solid; Rt 1.26 min (Method 1); m/z 463 (M+H)+(ES+); ¹H NMR (d₆-DMSO) δ: 8.14 (s, 1H), 8.05 (ddd, 1H), 7.58 (d, 1H), 7.15 (ddd, 1H), 7.09 (ddd, 1H), 7.01 (t, 1H), 6.91 (t, 1H), 5.23 (dd, 1H), 3.77 (d, 3H), 3.65 (p, 1H), 3.14-2.98 (m, 3H), 2.94-2.82 (m, 1H), 2.40 (s, 3H), 2.38-2.26 (m, 5H), 2.23 (s, 3H), 2.15-1.90 (m, 2H), 1.26 (t, 3H).

Example 2: 4-(2-(1-(3-fluoro-4-(trifluoromethoxy)phenyl)propan-2-yl)-1-(1-methylpyrrolidin-3-yl)-1H-benzo[d]imidazol-5-yl)-3,5-dimethylisoxazole

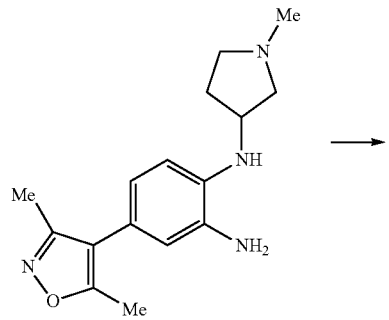

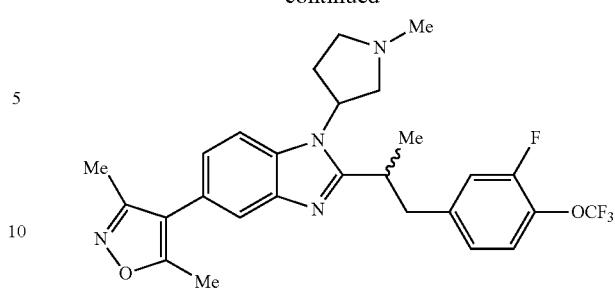

DIPEA (0.152 mL, 0.873 mmol) was added to a solution of 4-(3,5-dimethylisoxazol-4-yl)-N1-(1-methylpyrrolidin-3-yl)benzene-1,2-diamine (0.1 g, 0.349 mmol), 3-(3-fluoro-4-(trifluoromethoxy)phenyl)-2-methylpropanoic acid (0.102 g, 0.384 mmol) and HATU (0.173 g, 0.454 mmol) in DMF (1 mL, 12.91 mmol) at 0° C., allowed to warm to room temperature and stirred at RT for 20 h. The reaction was diluted with EtOAc (30 mL), washed with aqueous NaHCO₃ (20 mL), water (20 mL) and brine (10 mL), dried (MgSO4), filtered and evaporated in vacuo to give the crude amide as a light brown gum, which was dissolved in AcOH (3 mL, 52.4 mmol) and heated at 90° C. for 3 h. The temperature was reduced to 80° C., 4M HCl/dioxane (3 mL, 12.00 mmol) added and stirred at 80° C. for 20 h. Further HCl/dioxane (3 mL, 12.00 mmol) added and stirred at 90° C. for 16 h. The solvents were evaporated in vacuo and azeotroped with toluene (30 mL). The solid residue was dissolved in DCM (5 mL), absorbed onto SCX, washed with 20% MeOH/DCM, eluted with 20% 2M methanolic ammonia/DCM and evaporated in vacuo. The residue was purified by preparative HPLC (Gilson, Basic (0.1% Ammonium Bicarbonate), Basic, Waters X-Bridge Prep-C18, 5 µm, 19×50 mm column, 50-80% MeCN in Water) to give 4-(2-(1-(3-fluoro-4-(trifluoromethoxy)phenyl)propan-2-yl)-1-(1-methylpyrrolidin-3-yl)-1H-benzo[d]imidazol-5-yl)-3,5-dimethylisoxazole 2 (40 mg, 22%) as a off white solid; Rt 2.65 min (Method 2), m/z 517 (M+H)+(ES+); ¹H NMR (d₆-DMSO) δ: 8.07 (1H, dd), 7.60 (1H, m), 7.48-7.36 (2H, m), 7.18 (0.5H, t), 7.16 (0.5H, t), 7.13 (0.5H, dd), 7.07 (0.5H, dd), 5.25 (0.5H, m), 5.24 (0.5H, m), 3.74 (1H, m), 3.25-2.98 (3.5H, m), 2.78 (0.5H, m), 2.62 (0.5H, m), 2.41 (3H, s), 2.36 (1.5H, s), 2.31 (1.5H, s), 2.29 (2H, m), 2.24 (3H, s), 2.1-1.88 (1.5H, m), 1.31 (1.5H, d), 1.28 (1.5H, d).

Example 3 4-(2-(1-(4-chloro-3-fluorophenyl)propan-2-yl)-1-(3-(methylsulfonyl)propyl)-1H-benzo[d]imidazol-5-yl)-3,5-dimethylisoxazole 4-(3,5-dimethylisoxazol-4-yl)-N1-(3-(methylsulfonyl)propyl)benzene-1,2-diamine

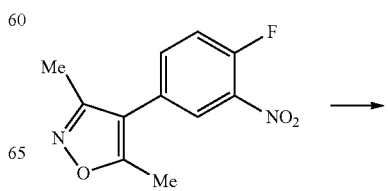

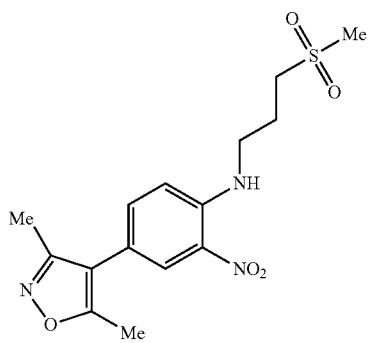

TEA (4.28 mL, 30.7 mmol) was added to a stirring mixture of 3-(methylsulfonyl)propan-1-amine hydrochloride (2 g, 11.52 mmol) and 4-(4-fluoro-3-nitrophenyl)-3,5-dimethylisoxazole (1.813 g, 7.68 mmol) in DMF (20 mL) and the resulting was stirred at 50° C. for 19 hours. The mixture was cooled down and poured on ice-water (150 mL). The orange precipitate was filtered off and washed with water (3×100 mL) then dried to afford 4-(3,5-dimethylisoxazol-4-yl)-N-(3-(methylsulfonyl)propyl)-2-nitroaniline (2.0 g, 5.38 mmol, 70%) as a orange solid; m/z 354 (M+H)+ (ES+).

4-(3,5-dimethylisoxazol-4-yl)-N1-(3-(methylsulfonyl)propyl)benzene-1,2-diamine

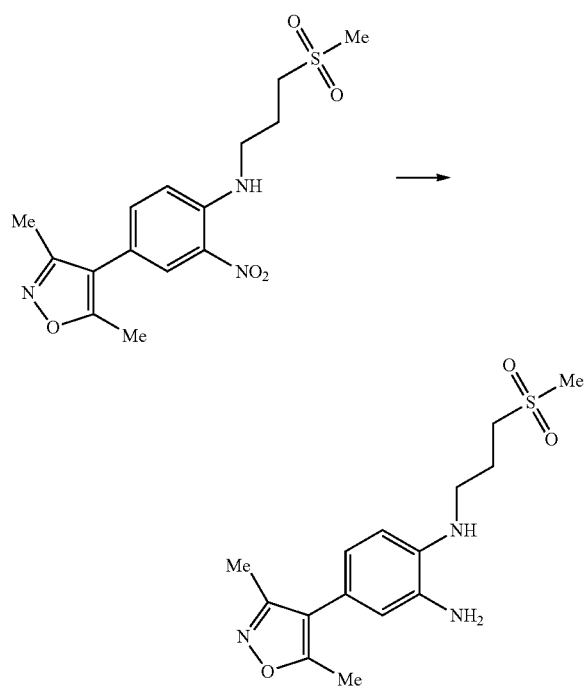

4-(3,5-dimethylisoxazol-4-yl)-N-(3-(methylsulfonyl)propyl)-2-nitroaniline (2 g, 5.43 mmol) was dissolved in THF/water (1:1, 400 mL) and concentrated aqueous ammonia (4.23 mL, 109 mmol), sodium dithionite (9.46 g, 54.3 mmol) were sequentially added. The reaction mixture stirred at RT for 2.25 h. The phases were separated, the aqueous extracted with EtOAc (100 mL), the combined organics washed with brine (2×100 mL), dried over Na$_2$SO$_4$, filtered and concentrated in vacuo to give 4-(3,5-dimethylisoxazol-4-yl)-N$^1$-(3-(methylsulfonyl)propyl) benzene-1,2-diamine (1.78 g, 5.23 mmol, 96% yield) as a light tan solid; m/z 324 (M+H)+ (ES+).

4-(2-(1-(4-chloro-3-fluorophenyl)propan-2-yl)-1-(3-(methylsulfonyl)propyl)-1H-benzo[d]imidazol-5-yl)-3,5-dimethylisoxazole

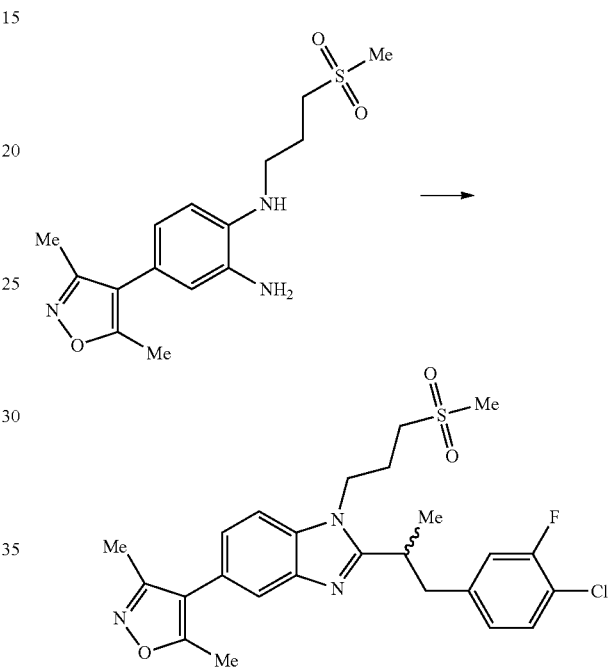

DIPEA (0.162 mL, 0.928 mmol) was added to a solution of 4-(3,5-dimethylisoxazol-4-yl)-N1-(3-(methylsulfonyl)propyl)benzene-1,2-diamine (0.12 g, 0.371 mmol), 3-(4-chloro-3-fluorophenyl)-2-methylpropanoic acid (0.088 g, 0.408 mmol) and HATU (0.183 g, 0.482 mmol) in DMF (1 mL, 12.91 mmol) at 0° C., allowed to attain room temperature and stirred at RT for 2 days. The reaction was diluted with EtOAc (30 mL), washed with aqNaHCO3 (20 mL), water (20 mL) and brine (10 mL), dried (MgSO4), filtered and evaporated in vacuo to give crude amide, which was dissolved in AcOH (10 mL, 175 mmol) and stirred at 90° C. for 16 h. The solvent was evaporated in vacuo, azeotroped with toluene (20 mL) and the residue purified by preparative HPLC (Waters, Acidic (0.1% Formic Acid), Acidic, Waters X-Bridge Prep-C18, 5 μm, 19×50 mm column, 20-50% MeCN in Water) to give 4-(2-(1-(4-chloro-3-fluorophenyl) propan-2-yl)-1-(3-(methylsulfonyl)propyl)-1H-benzo[d] imidazol-5-yl)-3,5-dimethylisoxazole 3 (50 mg, 29%) as a colourless foam; Rt 2.12 min m/z 504 (M+H)+(ES+); 1H NMR (d6-DMSO) δ: 7.65 (1H, d), 7.61 (1H, d), 7.45 (1H, m), 7.34 (1H, dd), 7.21 (1H, dd), 7.10 (1H, dd), 4.32 (2H, t), 3.54 (1H, m), 3.29-3.16 (3H, m), 3.00 (3H, s), 2.99 (1H, m), 2.41 (3H, s), 2.24 (3H, s), 2.06 (2H, m), 1.29 (3H, d).

Example 4: 4-(2-(1-(3-fluoro-4-(trifluoromethoxy) phenyl)propan-2-yl)-1-(3-(methyl sulfonyl)propyl)-1H-benzo[d]imidazol-5-yl)-3,5-dimethylisoxazole 4-(2-(1-(3-fluoro-4-(trifluoromethoxy)phenyl)propan-2-yl)-1-(3-(methylsulfonyl)propyl)-1H-benzo[d]imidazol-5-yl)-3,5-dimethylisoxazole

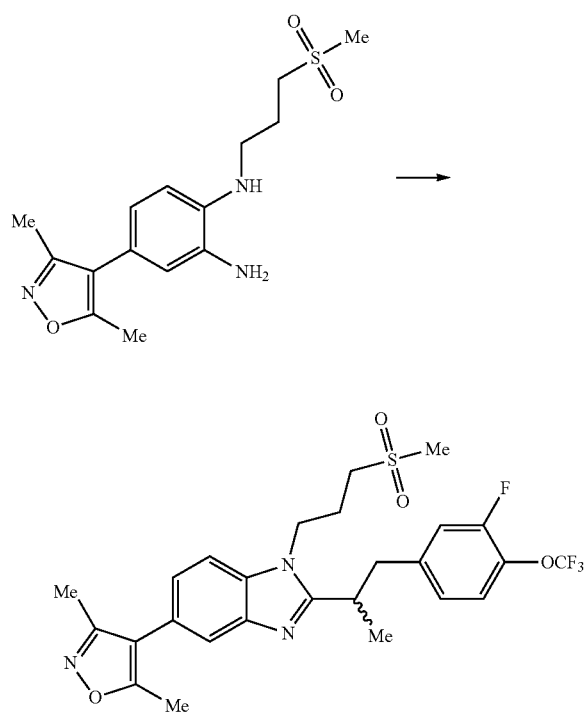 [SMILES: Cc1noc(C)c1-c1ccc(NCCCS(C)(=O)=O)c(N)c1 ; Cc1noc(C)c1-c1ccc2c(c1)nc(C(C)Cc1ccc(OC(F)(F)F)c(F)c1)n2CCCS(C)(=O)=O]

DIPEA (0.162 mL, 0.928 mmol) was added to a solution of 4-(3,5-dimethylisoxazol-4-yl)-N1-(3-(methylsulfonyl)propyl)benzene-1,2-diamine (0.12 g, 0.371 mmol), 3-(3-fluoro-4-(trifluoromethoxy)phenyl)-2-methylpropanoic acid (0.109 g, 0.408 mmol) and HATU (0.183 g, 0.482 mmol) in DMF (1 mL) at 0° C., allowed to warm to room temperature and stirred at RT for 3 h. The reaction was diluted with EtOAc (30 mL), washed with aqueous NaHCO3 (20 mL), water (20 mL) and brine (10 mL), dried (MgSO₄), filtered and evaporated in vacuo to give crude amide, which was redissolved in AcOH (10 mL, 175 mmol) and stirred at 90° C. for 16 h. The solvent was evaporated in vacuo, azeotroped with toluene (20 mL) and the residue purified by preparative HPLC (Waters, Acidic (0.1% Formic Acid), Acidic, Waters X-Bridge Prep-C18, 5 μm, 19×50 mm column, 10-60% MeCN in Water) to give 4-(2-(1-(3-fluoro-4-(trifluoromethoxy)phenyl)propan-2-yl)-1-(3-(methyl sulfonyl)propyl)-1H-benzo[d]imidazol-5-yl)-3,5-dimethylisoxazole 4 (48 mg, 26%) as a colourless foam; Rt 1.88 min, m/z 554.2 (M+H)+(ES+); 1H NMR (d6-DMSO) δ: 7.65 (1H, d), 7.61 (1H, d), 7.45 (2H, m), 7.21 (1H, dd), 7.19 (1H, d), 4.33 (2H, t), 3.55 (1H, m), 3.28-3.19 (3H, m), 3.03 (1H, m), 3.00 (3H, s), 2.41 (3H, s), 2.24 (3H, s), 2.07 (2H, m), 1.29 (3H, d).

Example 5 4-(5-(3,5-dimethylisoxazol-4-yl)-2-(1-(3-fluoro-4-methoxyphenyl)propan-2-yl)-1H-benzo[d]imidazol-1-yl)tetrahydro-2H-thiopyran 1,1-dioxide 4-((4-(3,5-dimethylisoxazol-4-yl)-2-nitrophenyl)amino)tetrahydro-2H-thiopyran 1,1-dioxide

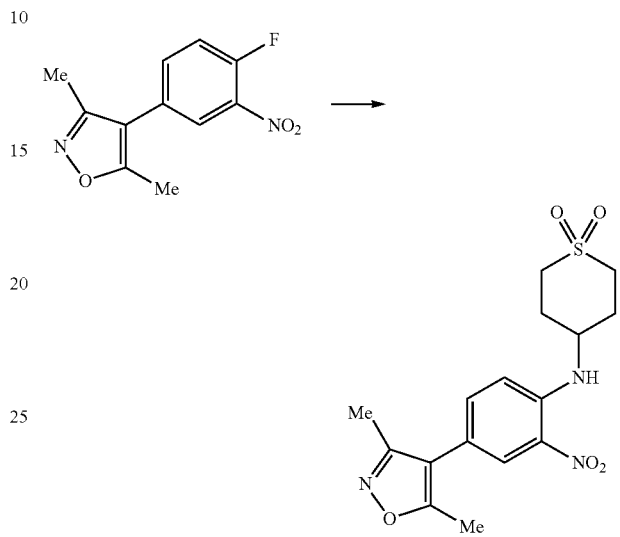

To a mixture of 4-(4-fluoro-3-nitrophenyl)-3,5-dimethylisoxazole (5.2 g, 22.02 mmol) and 4-aminotetrahydro-2H-thiopyran 1,1-dioxide, HCl (6.13 g, 33.0 mmol) in THF (20 mL) was added TEA (6.14 mL, 44.0 mmol) in DMF (50 mL) dropwise. The mixture was stirred at 90° C. for 24 hours. Saturated ammonium chloride (50 mL) was added and the precipitate taken into EtOAc (40 mL). The organic layer was washed with brine (2×40 mL) and dried over MgSO₄ then evaporated to dryness. The orange residue was purified by chromatography on silica gel (4 g column, 0-100% in) to afford 4-((4-(3,5-dimethylisoxazol-4-yl)-2-nitrophenyl)amino)tetrahydro-2H-thiopyran 1,1-dioxide (8.2 g, 100%) as a bright orange solid; m/z 366 (M+H)+(ES+).

4-((2-amino-4-(3,5-dimethylisoxazol-4-yl)phenyl)amino)tetrahydro-2H-thiopyran 1,1-dioxide

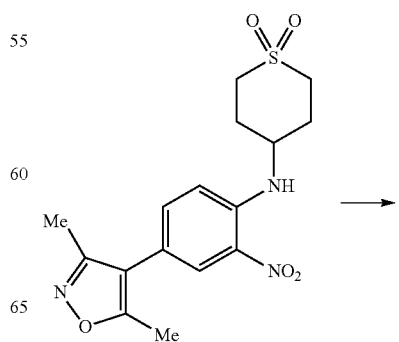

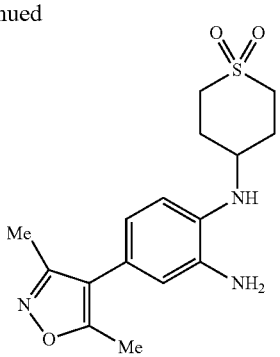

4-((4-(3,5-dimethylisoxazol-4-yl)-2-nitrophenyl)amino) tetrahydro-2H-thiopyran 1,1-dioxide (3.14 g, 8.59 mmol) was added to a solution of sodium dithionite (14.96 g, 86 mmol) and concentrated aqueous ammonia (6.69 mL, 172 mmol) in THF/water (1:1, 100 mL) and the reaction mixture stirred at RT for 2 hours. The reaction mixture was concentrated in vacuo to remove the organics and the bulk of the aqueous. The residue was partitioned between EtOAc (200 mL) and brine (40 mL), the phases separated and the organics dried over MgSO₄, filtered and concentrated in vacuo to give product as a dark red oil. The mixture was triturated with DCM to give 4-((2-amino-4-(3,5-dimethyl-isoxazol-4-yl)phenyl)amino) tetrahydro-2H-thiopyran 1,1-dioxide (1.55 g, 51%) as a light pink solid; m/z 336 (M+H)+(ES+).

4-(5-(3,5-dimethylisoxazol-4-yl)-2-(1-(3-fluoro-4-methoxyphenyl)propan-2-yl)-1H-benzo[d]imidazol-1-yl)tetrahydro-2H-thiopyran 1,1-dioxide

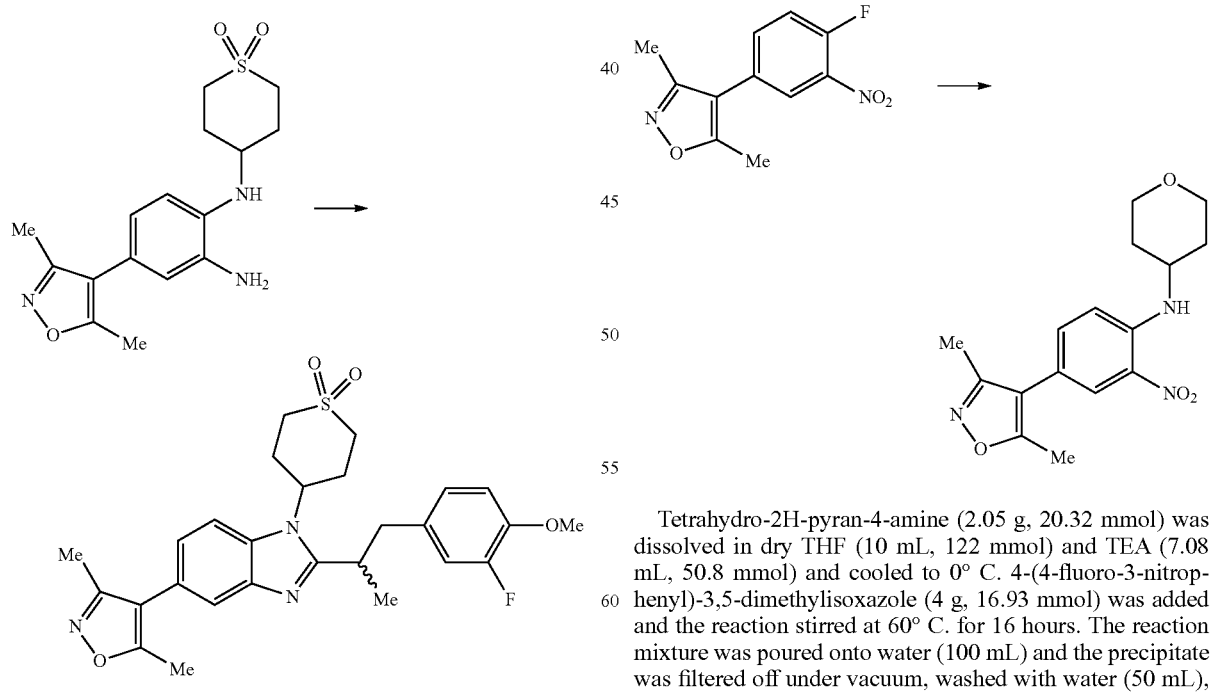

DIPEA (0.187 mL, 1.073 mmol) was added dropwise to a stirring solution of 4-((2-amino-4-(3,5-dimethylisoxazol-4-yl)phenyl)amino)tetrahydro-2H-thiopyran 1,1-dioxide (0.12 g, 0.358 mmol), 3-(3-fluoro-4-methoxyphenyl)-2-methylpropanoic acid (0.091 g, 0.429 mmol) and 2-(3H-[1,2,3]triazolo[4,5-b]pyridin-3-yl)-1,1,3,3-tetramethylisouronium hexafluorophosphate(V) (0.299 g, 0.787 mmol) in DMF (3 mL) and the resulting red solution was stirred at room temperature for 4 hours. The mixture was diluted with water and extracted with ethyl acetate (100 mL) (×2). The organic layer was dried (MgSO4), filtered and evaporated under reduced pressure to give intermediate as a brown oil. The crude product was purified by chromatography on the Companion (12 g column, 0-10% MeOH in DCM) to afford the amide intermediate, which was redissolved in acetic acid (2 mL) and heated to 100 C for 16 hours then evaporated to dryness. The crude product was purified by preparative HPLC (Waters, Acidic (0.1% Formic acid), Basic, Waters X-Bridge Prep-C18, 5 µm, 19×50 mm column, 20-50% MeCN in Water) to afford 4-(5-(3,5-dimethylisoxazol-4-yl)-2-(1-(3-fluoro-4-methoxyphenyl)propan-2-yl)-1H-benzo[d]imidazol-1-yl)tetrahydro-2H-thiopyran 1,1-dioxide (12 mg, 6%) as a cream solid; Rt 2.07 (Method 2), m/z 512 (M+H)+ (ES+); 1H NMR (d6-DMSO) δ: 7.64 (d, 1H), 7.56 (d, 1H), 7.23 (dd, 1H), 7.21-7.09 (m, 1H), 7.10-6.90 (m, 2H), 4.91 (t, 1H), 3.78 (s, 3H), 3.62 (t, 1H), 3.54-3.40 (m, 1H), 3.39 (m, 2H), 3.26-3.15 (m, 1H), 3.09 (dd, 1H), 2.94 (dd, 1H), 2.87-2.71 (m, 1H), 2.42 (s, 3H), 2.25 (s, 5H), 1.64 (s, 1H), 1.29 (d, 3H).

Example 6: 4-(2-(1-(4-fluorophenyl)propan-2-yl)-1-(tetrahydro-2H-pyran-4-yl)-1H-benzo[d]imidazol-5-yl)-3,5-dimethylisoxazole N-(4-(3,5-dimethylisoxazol-4-yl)-2-nitrophenyl) tetrahydro-2H-pyran-4-amine Tetrahydro-2H-pyran-4-amine (2.05 g, 20.32 mmol) was dissolved in dry THF (10 mL, 122 mmol) and TEA (7.08 mL, 50.8 mmol) and cooled to 0° C. 4-(4-fluoro-3-nitrophenyl)-3,5-dimethylisoxazole (4 g, 16.93 mmol) was added and the reaction stirred at 60° C. for 16 hours. The reaction mixture was poured onto water (100 mL) and the precipitate was filtered off under vacuum, washed with water (50 mL), isohexane (100 mL) and dried in vacuo to give N-(4-(3,5-dimethylisoxazol-4-yl)-2-nitrophenyl)tetrahydro-2H-pyran-4-amine (4.85 g, 87%) as a bright orange solid; m/z 318 (M+H)+(ES+).

4-(3,5-dimethylisoxazol-4-yl)-N1-(tetrahydro-2H-pyran-4-yl)benzene-1,2-diamine

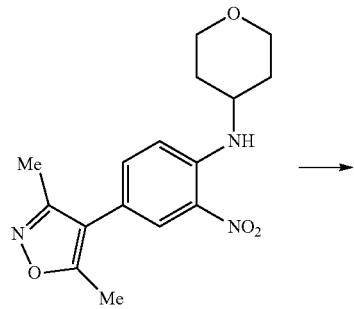

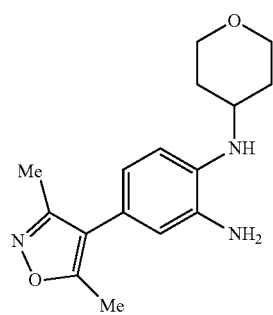

Sodium dithionite (24.96 g, 143 mmol) was added to a solution of N-(4-(3,5-dimethylisoxazol-4-yl)-2-nitrophenyl)tetrahydro-2H-pyran-4-amine (4.55 g, 14.34 mmol) and concentrated aqueous ammonia (11.17 mL, 287 mmol) in THF/water (1:1, 100 mL) and the reaction mixture stirred at RT for 2 hours. The reaction mixture was concentrated in vacuo to remove the organics and the bulk of the aqueous. The residue was partitioned between EtOAc (200 mL) and brine (40 mL), the phases separated and the organics dried over MgSO4, filtered and concentrated in vacuo to give product as a dark brown solid. The crude product was purified by chromatography on silica gel (80 g column, 0-100% ethyl acetate in isohexane) to afford 4-(3,5-dimethylisoxazol-4-yl)-N1-(tetrahydro-2H-pyran-4-yl)benzene-1,2-diamine (2.77 g, 67%) as a purple foam; m/z 288 (M+H)+ (ES+).

4-(2-(1-(4-fluorophenyl)propan-2-yl)-1-(tetrahydro-2H-pyran-4-yl)-1H-benzo[d]imidazol-5-yl)-3,5-dimethylisoxazole

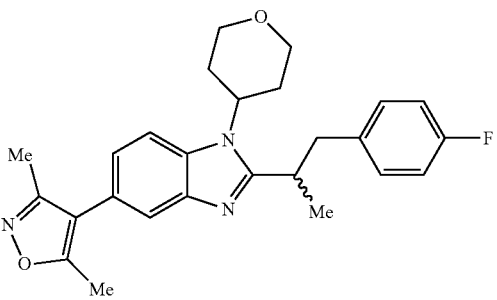

DIPEA (0.22 mL, 1.253 mmol) was added dropwise to a stirring solution of 4-(3,5-dimethylisoxazol-4-yl)-N1-(tetrahydro-2H-pyran-4-yl)benzene-1,2-diamine (0.12 g, 0.418 mmol), 3-(4-fluorophenyl)-2-methylpropanoic acid (0.091 g, 0.501 mmol) and 2-(3H-[1,2,3]triazolo[4,5-b]pyridin-3-yl)-1,1,3,3-tetramethylisouronium hexafluorophosphate(V) (0.349 g, 0.919 mmol) in DMF (10 mL) and the resulting brown solution was stirred at room temperature for 16 hours. The mixture was diluted with water and extracted with diethyl ether (150 mL) (×2). The organic layer was dried (MgSO4), filtered and evaporated under reduced pressure to give intermediate as a brown oil. The oil was dissolved in acetic acid (2 mL) and heated to 90° C. for 32 hours. The mixture was evaporated to dryness and the crude product was purified by preparative HPLC (Waters, Acidic (0.1% Formic acid), Acidic, Waters X-Select Prep-C18, 5 μm, 19×50 mm column, 10-40% MeCN in Water) to afford 4-(2-(1-(4-fluorophenyl)propan-2-yl)-1-(tetrahydro-2H-pyran-4-yl)-1H-benzo[d]imidazol-5-yl)-3,5-dimethylisoxazole (66 mg, 36%) as a light tan solid; Rt 1.67 mn (Method 1), m/z 434 (M+H)+(ES+); 1H NMR (d6-DMSO) δ: 7.67 (d, 1H), 7.61 (d, 1H), 7.30-7.19 (m, 2H), 7.14 (dd, 1H), 7.10-7.01 (m, 2H), 4.69-4.48 (m, 1H), 3.98 (ddd, 2H), 3.67 (p, 1H), 3.62-3.53 (m, 1H), 3.53-3.43 (m, 1H), 3.14 (dd, 1H), 3.00 (dd, 1H), 2.41 (s, 3H), 2.34 (td, 2H), 2.24 (s, 3H), 1.74 (d, 1H), 1.32 (d, 3H), 1.22 (d, 1H).

Example 7: 3,5-dimethyl-4-(2-(1-(pyridin-2-yl)propan-2-yl)-1-(tetrahydro-2H-pyran-4-yl)-1H-benzo[d]imidazol-5-yl) isoxazole

3,5-dimethyl-4-(2-(1-(pyridin-2-yl)propan-2-yl)-1-(tetrahydro-2H-pyran-4-yl)-1H-benzo[d]imidazol-5-yl)isoxazole

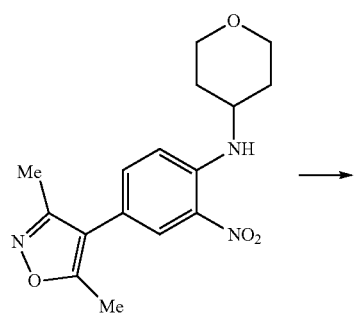

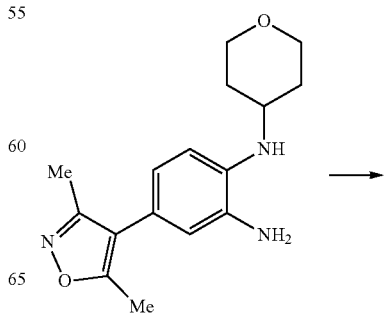

-continued

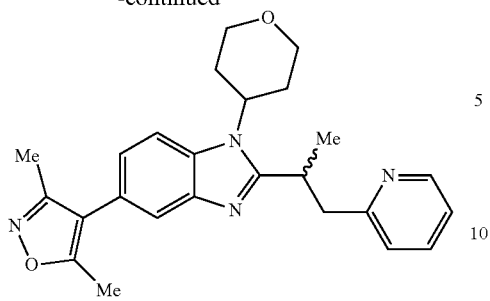

DIPEA (63.6 μl, 0.365 mmol) was added to a mixture of 2-methyl-3-(pyridin-2-yl)propanoic acid (60.4 mg, 0.365 mmol), 4-(3,5-dimethylisoxazol-4-yl)-N1-(tetrahydro-2H-pyran-4-yl)benzene-1,2-diamine (100 mg, 0.348 mmol) and 2-(3H-[1,2,3]triazolo[4,5-b]pyridin-3-yl)-1,1,3,3-tetramethylisouronium hexafluorophosphate(V) (139 mg, 0.365 mmol) in DMF (1 mL). The reaction mixture was stirred at rt for 18 h. DCM (10 mL) and saturated sodium bicarbonate solution (5 mL) were added and the reaction mixture shaken thoroughly. The organic phase was collected, washed with brine (10 mL) and collected via PhaseSep cartridge. The solvent was removed in vacuo to afford a loose brown solid, which was redissolved in acetic acid (1 mL) and heated to 80° C. with stirring for 72 h. After cooling to rt, methanol (5 mL) was added and the solution was treated to SCX chromatography; eluting the compound with 1% ammonia in methanol solution. The ammoniacal eluent was concentrated in vacuo and the crude residue was purified by chromatography (4 g silica, 0-10% methanol in DCM, gradient elution) to afford 3,5-dimethyl-4-(2-(1-(pyridin-2-yl)propan-2-yl)-1-(tetrahydro-2H-pyran-4-yl)-1H-benzo[d]imidazol-5-yl) isoxazole (20 mg, 13%) as an off white solid; Rt 1.29 min (Method 1), m/z 417 (M+H)+(ES+); 1H NMR (d6-DMSO) δ: 8.49 (ddd, J=4.8, 1.9, 0.9 Hz, 1H), 7.71-7.55 (m, 3H), 7.26-7.08 (m, 3H), 4.71 (dd, J=13.6, 9.4 Hz, 1H), 4.14-3.88 (m, 3H), 3.64-3.45 (m, 2H), 3.43-3.26 (m, 28H), 3.20-3.08 (m, 2H), 2.39 (s, 4H), 2.22 (s, 3H), 1.78 (d, J=12.8 Hz, 1H), 1.48-1.31 (m, 4H)

Example 8: 4-(2-(1-(3-fluoro-4-methoxyphenyl) propan-2-yl)-1-(1-methylpiperidin-4-yl)-1H-benzo [d]imidazol-5-yl)-3,5-dimethylisoxazole N-(4-bromo-2-nitrophenyl)-1-methylpiperidin-4-amine

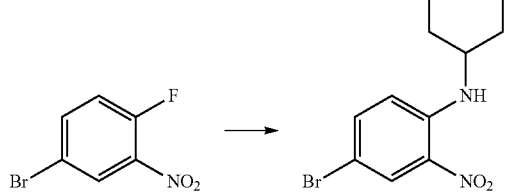

4-bromo-1-fluoro-2-nitrobenzene (2.5 g, 11.36 mmol) was dissolved in dry THF (20 mL) and TEA (3.17 mL, 22.73 mmol) and cooled to 0° C. under nitrogen. 1-methylpiperidin-4-amine (1.62 g, 14.20 mmol) was added and the reaction mixture stirred at RT overnight. Further 1-methylpiperidin-4-amine (0.649 g, 5.68 mmol) was added and the reaction mixture stirred at RT overnight. The reaction mixture was poured onto water (100 mL) and the precipitate was filtered off under vacuum, washed with water (50 mL), isohexane (100 mL) and dried in vacuo to give N-(4-bromo-2-nitrophenyl)-1-methylpiperidin-4-amine (3.73 g, 99%) as a bright orange solid; m/z 314/316 (M+H)+(ES+).

4-bromo-N1-(1-methylpiperidin-4-yl)benzene-1,2-diamine

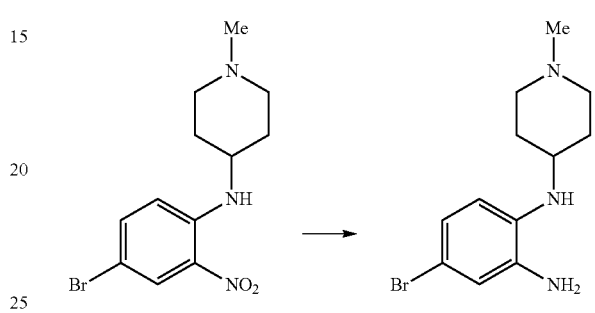

N-(4-bromo-2-nitrophenyl)-1-methylpiperidin-4-amine (3.73 g, 11.28 mmol) and concentrated aqueous ammonia (8.78 mL, 226 mmol) were dissolved in THF/water (1:1, 240 mL), sodium dithionite (19.64 g, 113 mmol) was added and the reaction mixture was stirred at RT for 1.5 h. The phases were separated, the aqueous extracted with EtOAc (60 mL), the combined organics washed with brine (30 mL), dried over MgSO4, filtered and concentrated in vacuo to give red solid, (2.09 g, 59%), which was used without further purification; m/z 284/286 (M+H)+(ES+).

5-bromo-2-(1-(3-fluoro-4-methoxyphenyl)propan-2-yl)-1-(1-methylpiperidin-4-yl)-1H-benzo[d]imidazole

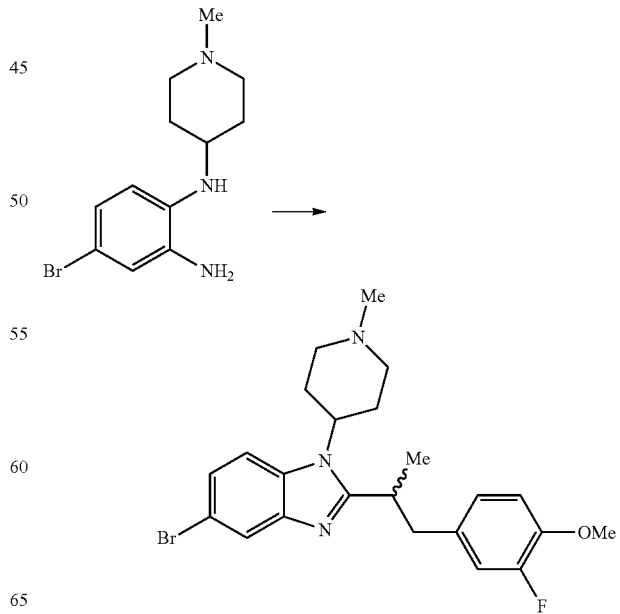

A mixture of 4-bromo-N1-(1-methylpiperidin-4-yl)benzene-1,2-diamine (99 mg, 0.35 mmol), 3-(3-fluoro-4-methoxyphenyl)-2-methylpropanoic acid (97 mg, 0.455 mmol), HATU (173 mg, 0.455 mmol), DIPEA (202 µl, 1.155 mmol) in DMF (1750 µl, 0.350 mmol) was stirred overnight. The mixture was diluted with EtOAc (2 mL) and water (2 mL). The layers were separated and the organic layer was washed with water (3×2 mL), dried (MgSO4), filtered and reduced in vacuo. The mixture was diluted with AcOH (2 mL) and then heated at 80° C. overnight. The mixture was cooled to room temperature and then azeotropped with toluene. The crude product was purified by chromatography on the Companion (12 g column, 0-10% MeOH/DCM) to afford 5-bromo-2-(1-(3-fluoro-4-methoxyphenyl)propan-2-yl)-1-(1-methylpiperidin-4-yl)-1H-benzo[d]imidazole (115 mg, 68%) as a white solid; m/z 479 (M+H)+(ES+).

4-(2-(1-(3-fluoro-4-methoxyphenyl)propan-2-yl)-1-(1-methylpiperidin-4-yl)-1H-benzo[d]imidazol-5-yl)-3,5-dimethylisoxazole

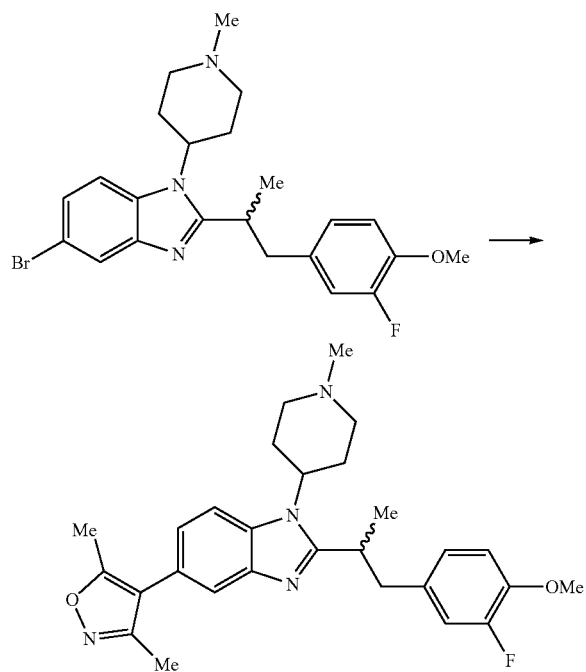

(3,5-dimethylisoxazol-4-yl)boronic acid (51.9 mg, 0.368 mmol) followed by Pd(PPh3)4 (42.5 mg, 0.037 mmol) were added to a degassed mixture of 5-bromo-2-(1-(3-fluoro-4-methoxyphenyl)propan-2-yl)-1-(1-methylpiperidin-4-yl)-1H-benzo[d]imidazole (113 mg, 0.245 mmol) and potassium carbonate (102 mg, 0.736 mmol) in 3:1 dioxane:H2O (20 mL) and the mixture was stirred under nitrogen at 90° C. for overnight. The mixture was allowed to cool to room temperature and water was added. The mixture was transferred into a separating funnel and the crude product was extracted with EtOAc. The organic layer was dried (MgSO4), filtered and reduced in vacuo. The crude product was purified by preparative HPLC (Waters, Acidic (0.1% Formic acid), Acidic, Waters X-Select Prep-C18, 5 µm, 19×50 mm column, 5-95% MeCN in Water) to afford 4-(2-(1-(3-fluoro-4-methoxyphenyl)propan-2-yl)-1-(1-methylpiperidin-4-yl)-1H-benzo[d]imidazol-5-yl)-3,5-dimethylisoxazole (32 mg, 27%) as a white solid; Rt 1.24 min (Method 1), 477.3 (M+H)+(ES+); 1H NMR (d6-DMSO) δ: 7.66-7.56 (m, 2H), 7.15-7.06 (m, 2H), 7.05-6.95 (m, 1H), 6.90 (d, 1H), 4.27 (t, 1H), 3.75 (s, 3H), 3.60 (q, 1H), 3.06 (dd, 1H), 3.00-2.80 (m, 3H), 2.40 (s, 4H), 2.23 (d, 6H), 2.19-1.98 (m, 2H), 1.72 (d, 1H), 1.30 (d, 3H), 1.18 (d, 1H).

Example 9: 1-(4-((2-(1-(4-chlorophenyl)propan-2-yl)-5-(3,5-dimethylisoxazol-4-yl)-1H-benzo[d]imidazol-1-yl)methyl)piperidin-1-yl)ethan-1-one tert-butyl-4-(((4-(3,5-dimethylisoxazol-4-yl)-2-nitrophenyl)amino)methyl)piperidine-1-carboxylate

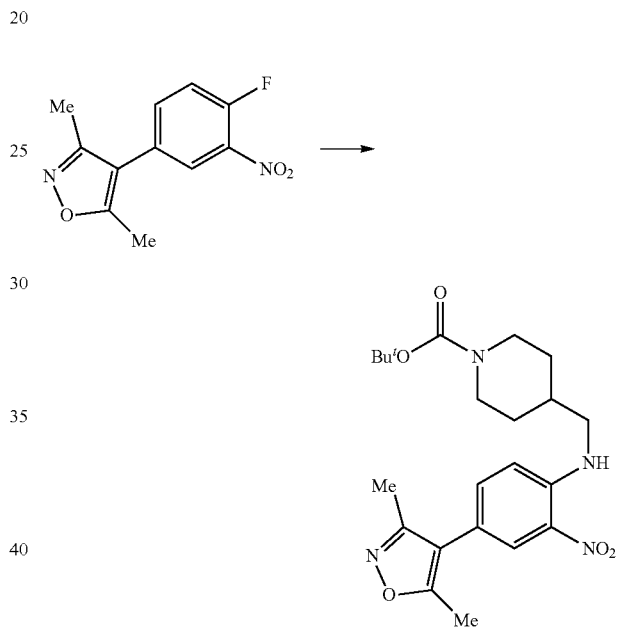

4-(4-fluoro-3-nitrophenyl)-3,5-dimethylisoxazole (2.5 g, 10.27 mmol) was dissolved in dry THF (30 mL, 366 mmol) under nitrogen and cooled to 0° C., then TEA (4.29 mL, 30.8 mmol) was added, followed by tert-butyl 4-(aminomethyl)piperidine-1-carboxylate (3.30 g, 15.40 mmol) and the reaction mixture allowed up to RT with stirring overnight. Further tert-butyl 4-(aminomethyl)piperidine-1-carboxylate (1.7 g, 7.93 mmol) and TEA (2.146 mL, 15.40 mmol) were added and the reaction mixture heated to 40° C. overnight. The reaction mixture was cooled to RT, the reaction mixture was poured onto ice cold water (100 mL), extracted with EtOAc (3×100 mL), the combined organics washed with brine (75 mL), dried over Na2SO4, filtered and concentrated in vacuo, dried azeotropically with Et2O. The crude product was purified by chromatography on the Companion (120 g column, 20-100% EtOAc in isohexanes, dry loaded, 50 mL fractions). fl9-36 were combined and concentrated in vacuo to give tert-butyl 4-(((4-(3,5-dimethylisoxazol-4-yl)-2-nitrophenyl)amino)methyl)piperidine-1-carboxylate as a orange solid, (4.45 g, 94%); m/z 431 (M+H)+(ES+).

4-(3,5-dimethylisoxazol-4-yl)-2-nitro-N-(piperidin-4-ylmethyl)aniline hydrochloride

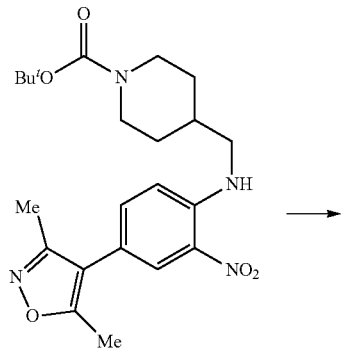

tert-butyl-4-(((4-(3,5-dimethylisoxazol-4-yl)-2-nitrophenyl)amino)methyl)piperidine-1-carboxylate (4.45 g, 9.61 mmol) was suspended in 4M HCl in dioxane (25 mL, 100 mmol) under nitrogen and stirred at RT for 6 h. The reaction mixture was concentrated in vacuo, dried azeotropically with Et$_2$O to give 4-(3,5-dimethylisoxazol-4-yl)-2-nitro-N-(piperidin-4-ylmethyl)aniline hydrochloride as a orange solid (3.78 g, 100%); m/z 331 (M+H)+(ES+).

1-(4-(((4-(3,5-dimethylisoxazol-4-yl)-2-nitrophenyl)amino)methyl)piperidin-1-yl)ethanone

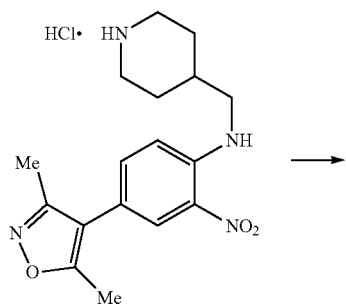

4-(3,5-dimethylisoxazol-4-yl)-2-nitro-N-(piperidin-4-yl-methyl)aniline hydrochloride 4-(3,5-dimethylisoxazol-4-yl)-2-nitro-N-(piperidin-4-yl-methyl)aniline hydrochloride (3.78 g, 9.58 mmol) was suspended in dry DCM (30 mL, 466 mmol) under nitrogen and cooled to 0° C., DIPEA (5.02 mL, 28.7 mmol) was added over 5 min, followed by AcCl (0.750 mL, 10.54 mmol) over 5 min and the reaction mixture allowed to warm slowly to RT overnight. The reaction mixture was diluted with DCM (30 mL) and sat. NaHCO3 (20 mL), the phases separated, the organics washed with water (20 mL), 10% citric acid (20 mL), water (20 mL), brine (20 mL), dried over MgSO$_4$, filtered and concentrated in vacuo to give 1-(4-(((4-(3,5-dimethylisoxazol-4-yl)-2-nitrophenyl)amino)methyl)piperidin-1-yl)ethanone as a deep red oil (4.88 g, 98%), which was used without further purification; m/z 343 (M+H)+(ES+).

1-(4-(((2-amino-4-(3,5-dimethylisoxazol-4-yl)phenyl)amino)methyl)piperidin-1-yl)ethanone

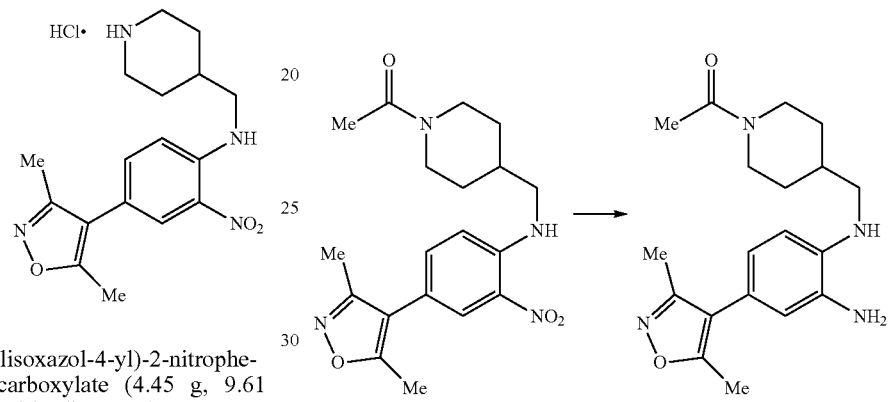

1-(4-(((4-(3,5-dimethylisoxazol-4-yl)-2-nitrophenyl)amino)methyl)piperidin-1-yl)ethanone (4.88 g, 9.43 mmol) and concentrated aqueous ammonia (7.35 mL, 189 mmol) were dissolved in THF (100 mL, 1220 mmol) and water (100 mL, 5551 mmol), sodium dithionite (16.43 g, 94 mmol) was added and the reaction mixture stirred at RT for 3.75 h. The phases were separated, the aqueous extracted with EtOAc (200 mL), the combined organics were washed with brine (80 mL), dried over Na$_2$SO$_4$, filtered and concentrated in vacuo, dried azeotropically with Et$_2$O to give 1-(4-(((2-amino-4-(3,5-dimethylisoxazol-4-yl)phenyl)amino) methyl) piperidin-1-yl)ethanone as a pink solid (2.98 g, 88%), which was used without further purification; m/z 343 (M+H)+(ES+).

1-(4-((2-(1-(4-chlorophenyl)propan-2-yl)-5-(3,5-dimethylisoxazol-4-yl)-1H-benzo[d]imidazol-1-yl)methyl)piperidin-1-yl)ethan-1-one

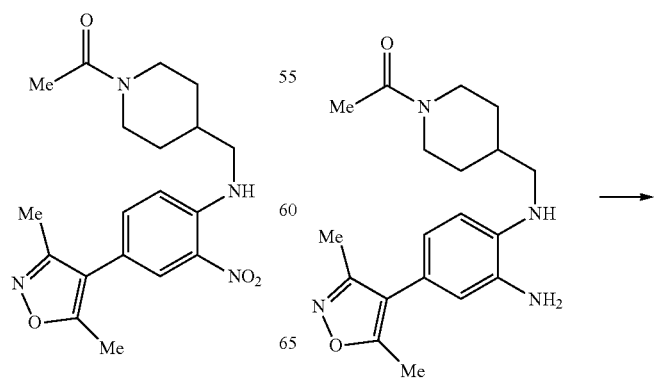

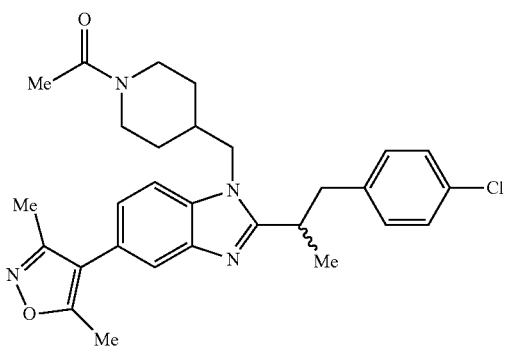

DIPEA (0.229 mL, 1.314 mmol) was added dropwise to a stirring solution of 1-(4-(((2-amino-4-(3,5-dimethylisoxazol-4-yl)phenyl)amino)methyl)piperidin-1-yl)ethanone (0.15 g, 0.438 mmol), 3-(4-chlorophenyl)-2-methylpropanoic acid (0.104 g, 0.526 mmol) and 2-(3H-[1,2,3]triazolo[4,5-b]pyridin-3-yl)-1,1,3,3-tetramethylisouronium hexafluorophosphate (V) (0.366 g, 0.964 mmol) in DMF (10 mL) and the resulting brown solution was stirred at room temperature for 16 hours. The mixture was diluted with water and extracted with diethyl ether (150 mL) (×2). The organic layer was dried (MgSO4), filtered and evaporated under reduced pressure to give intermediate as a brown oil. The oil was dissolved in acetic acid (2 mL) and heated to 90 C for 32 hours. The mixture was evaporated to dryness. The crude product was purified by preparative HPLC (Waters, Acidic (0.1% Formic acid), Acidic, Waters X-Select Prep-C18, 5 μm, 19×50 mm column, 10-40% MeCN in Water) to afford crude product not pure enough so the crude product was purified by preparative HPLC (Waters, Basic (0.1% Ammonium Bicarbonate), Basic, Waters X-Bridge Prep-C18, 5 μm, 19×50 mm column, 30-50% MeCN in Water) to afford 1-(4-((2-(1-(4-chlorophenyl)propan-2-yl)-5-(3,5-dimethylisoxazol-4-yl)-1H-benzo[d]imidazol-1-yl)methyl)piperidin-1-yl)ethanone (10 mg, 4%) as a white solid; Rt 1.66 min (Method 1), m/z 506 (M+H)+(ES+); 1H NMR (400 MHz, DMSO-d6) δ 7.64-7.53 (m, 2H), 7.30-7.25 (m, 2H), 7.21 (d, 2H), 7.15 (dd, 1H), 4.32 (d, 1H), 3.98 (hept, 2H), 3.78-3.54 (m, 1H), 3.40 (dt, 1H), 3.22 (ddd, 1H), 2.97 (dd, 1H), 2.89-2.64 (m, 1H), 2.42 (s, 3H), 2.25 (m, 5H), 1.96 (d, 3H), 1.70 (s, 1H), 1.32 (dd, 4H), 1.23-1.01 (m, 2H).

Example 10: 4-(2-(1-(3-fluoro-4-methoxyphenyl)propan-2-yl)-1-((tetrahydro-2H-pyran-4-yl)methyl)-1H-benzo[d]imidazol-5-yl)-3,5-dimethylisoxazole 4-(3,5-dimethylisoxazol-4-yl)-2-nitro-N-((tetrahydro-2H-pyran-4-yl)methyl)aniline

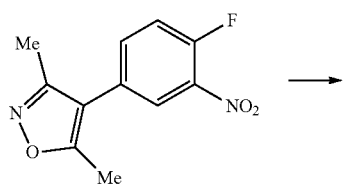

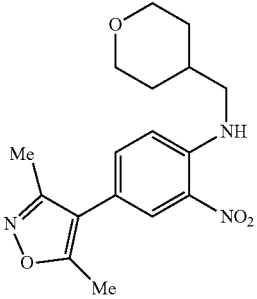

4-(4-fluoro-3-nitrophenyl)-3,5-dimethylisoxazole (1.1 g, 4.66 mmol) was dissolved in dry THF (12 mL, 146 mmol) and TEA (1.298 mL, 9.31 mmol) and cooled to 0° C. (tetrahydro-2H-pyran-4-yl)methanamine (0.670 g, 5.82 mmol) was added and the reaction stirred at RT for 3 h, then further (tetrahydro-2H-pyran-4-yl)methanamine (0.268 g, 2.329 mmol) was added and the reaction mixture stirred at RT overnight. Further (tetrahydro-2H-pyran-4-yl)methanamine (0.161 g, 1.397 mmol) was charged and the reaction mixture heated to 40° C. for 2 h. The reaction mixture was cooled to RT, poured onto ice water (60 mL), the resulting precipitate filtered off, washed with ice cold water (20 mL), the solids dried in vacuo to give 4-(3,5-dimethylisoxazol-4-yl)-2-nitro-N-((tetrahydro-2H-pyran-4-yl)methyl)aniline as a bright orange solid (1.93 g, 100%); m/z 332 (M+H)+ (ES+).

4-(3,5-dimethylisoxazol-4-yl)-N1-((tetrahydro-2H-pyran-4-yl)methyl)benzene-1,2-diamine

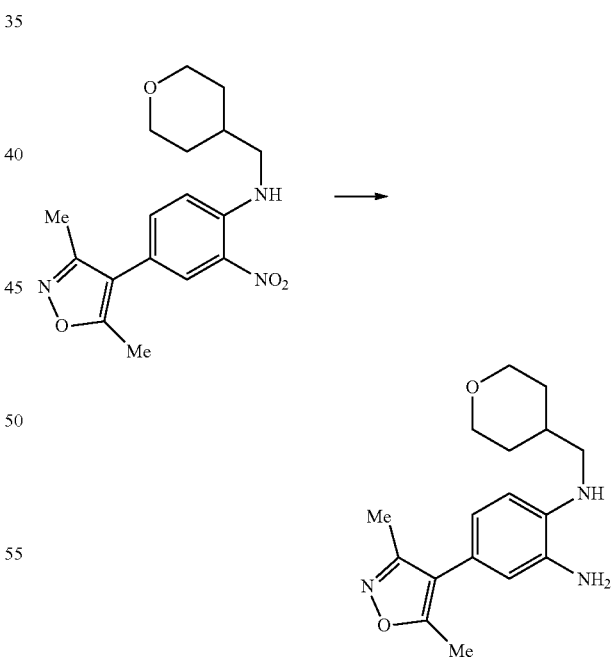

4-(3,5-dimethylisoxazol-4-yl)-2-nitro-N-((tetrahydro-2H-pyran-4-yl)methyl)aniline (1.93 g, 4.66 mmol) and NH4OH (3.63 mL, 93 mmol) were dissolved THF (60 mL, 732 mmol) and WATER (60 mL, 3331 mmol), sodium dithionite (8.11 g, 46.6 mmol) was added and the reaction mixture stirred at RT for 1 h. The reaction mixture was concentrated in vacuo to remove the organics, the resulting suspension extracted with EtOAc (2×60 mL), the combined organics washed with brine (30 mL), the organics dried over MgSO4, filtere and concentrated in vacuo to give 4-(3,5-dimethylisoxazol-4-yl)-N1-((tetrahydro-2H-pyran-4-yl)methyl)benzene-1,2-diamine as a pink solid (1.17 g, %); m/z 302 (M+H)+(ES+).

4-(2-(1-(3-fluoro-4-methoxyphenyl)propan-2-yl)-1-((tetrahydro-2H-pyran-4-yl)methyl)-1H-benzo[d]imidazol-5-yl)-3,5-dimethylisoxazole

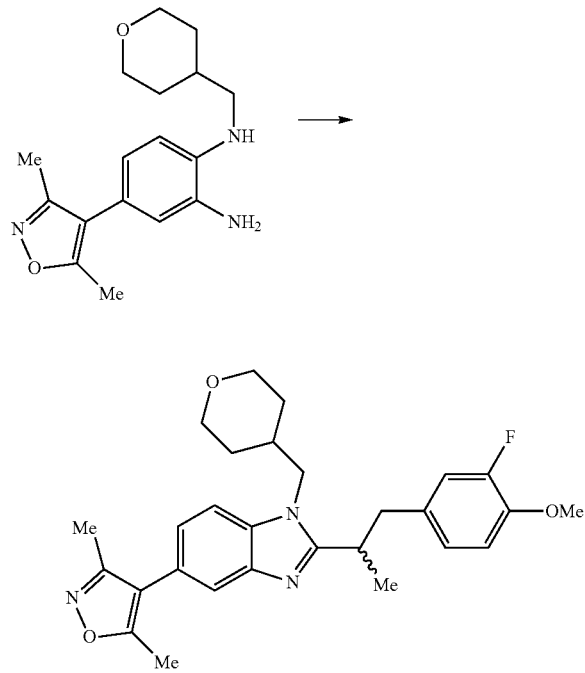

4-(3,5-dimethylisoxazol-4-yl)-N1-((tetrahydro-2H-pyran-4-yl)methyl)benzene-1,2-diamine (250 mg, 0.788 mmol) and 3-(3-fluoro-4-methoxyphenyl)-2-methylpropanoic acid (201 mg, 0.946 mmol) were dissolved in DMF (5 mL, 64.6 mmol) under nitrogen, HATU (360 mg, 0.946 mmol) was added followed by DIPEA (0.275 mL, 1.576 mmol) and the reaction mixture stirred at RT over the weekend. The reaction mixture was concentrated in vacuo, the residue partuitioned between EtOAc (50 mL) and water (20 mL), the organics washed with brine (20 mL), dried over MgSO4, filtered and concentrated in vacuo to give a pink solid, which was redissolved in AcOH (20 mL, 349 mmol) and heated to 100° C. overnight. The reaction mixture was cooled to RT, concentrated in vacuo and the residue loaded onto a column of SCX (10 g) in MeOH. The column was washed with MeOH and then the product was eluted with 0.7 M ammonia in MeOH. The resultant mixture was concentrated in vacuo to afford a brown oily solid, 218 mg. 1H NMR in DMSO-d6 1218-47 cru was consistent with product structure at ~70% purity. The crude product was purified by chromatography on the Companion (40 g column, 0-4% MeOH in DCM, dry loaded, slow gradient). f51-53 were combined and concentrated in vacuo to give 4-(2-(1-(3-fluoro-4-methoxyphenyl)propan-2-yl)-1-((tetrahydro-2H-pyran-4-yl)methyl)-1H-benzo[d]imidazol-5-yl)-3,5-dimethylisoxazole as a cream solid (63 mg, 16%); Rt 1.64 min (Method 1), m/z 478 (M+H)+(ES+); 1H NMR (d6-DMSO) δ 7.63-7.56 (m, 2H), 7.15 (dd, 1H), 7.04 (dd, 1H), 6.97 (t, 1H), 6.88 (dd, 1H), 3.98 (dd, 2H), 3.73 (s, 5H), 3.46-3.35 (m, 1H), 3.20-3.11 (m, 1H), 3.11-2.95 (m, 2H), 2.91 (dd, 1H), 2.41 (s, 3H), 2.24 (s, 3H), 1.64 (s, 1H), 1.36-1.09 (m, 7H).

Example 11 4-(2-(1-(4-chlorophenyl)propan-2-yl)-1-(2-(tetrahydro-2H-pyran-4-yl)ethyl)-1H-benzo[d]imidazol-5-yl)-3,5-dimethylisoxazole 4-(3,5-dimethylisoxazol-4-yl)-2-nitro-N-(2-(tetrahydro-2H-pyran-4-yl)ethyl)aniline

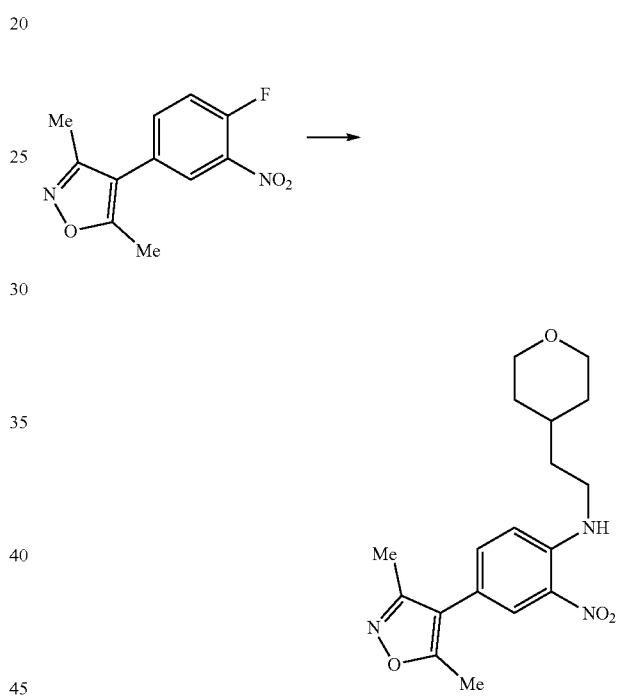

DIPEA (7.99 mL, 45.8 mmol) was added to a suspension of 2-(tetrahydro-2H-pyran-4-yl)ethanamine hydrochloride (3.63 g, 21.89 mmol) in THF (30 mL, 366 mmol) and stirred for 15 min. A solution of 4-(4-fluoro-3-nitrophenyl)-3,5-dimethylisoxazole (4.7 g, 19.90 mmol) in THF (40 mL, 488 mmol) was added to the suspension and stirred at RT for a further 2 h. DMF (10 mL, 129 mmol) was added and the reaction stirred at RT for a further 2 h. The reaction was heated at 50° C. for 20 h and then at 70° C. for a further 20 h. The solvent volume was reduced by evaporation in vacuo and the residue diluted with EtOAc (200 mL). The solution was washed with water (3×50 mL) and brine (30 mL), dried (MgSO4), filtered and evaporated in vacuo. The residual solid was purified by chromatography on the Companion (220 g column, 0-30% EtOAc in (2:1 DCM/isohexane), loaded in DCM) to give 4-(3,5-dimethylisoxazol-4-yl)-2-nitro-N-(2-(tetrahydro-2H-pyran-4-yl)ethyl)aniline (5.6 g, 80%) as a orange solid; m/z 346 (M+H)+(ES+).

4-(3,5-dimethylisoxazol-4-yl)-N1-(2-(tetrahydro-2H-pyran-4-yl)ethyl)benzene-1,2-diamine

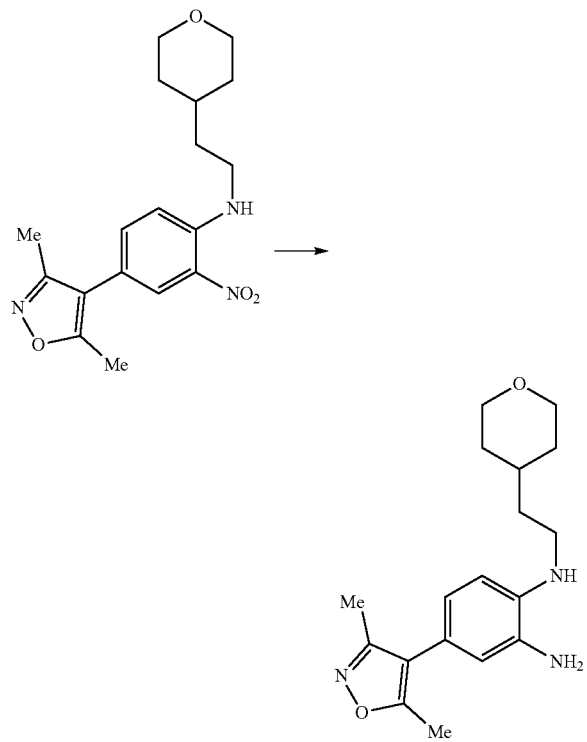

4-(3,5-dimethylisoxazol-4-yl)-2-nitro-N-(2-(tetrahydro-2H-pyran-4-yl)ethyl)aniline (5.6 g, 16.21 mmol) and concentrated aqueous ammonia (10 mL, 257 mmol) were dissolved in THF/water (1:1, 300 mL), sodium dithionite (28.2 g, 162 mmol) added and the reaction mixture stirred at RT for 2.5 h. The layers were separated, the aqueous extracted with EtOAc (100 mL), the combined organics washed with brine (50 mL), dried (MgSO4), filtered and evaporated in vacuo to give 4-(3,5-dimethylisoxazol-4-yl)-N1-(2-(tetrahydro-2H-pyran-4-yl)ethyl)benzene-1,2-diamine (4.7 g, 91%) as a pink solid; m/z 316.2 (M+H)+(ES+).

4-(2-(1-(4-chlorophenyl)propan-2-yl)-1-(2-(tetrahydro-2H-pyran-4-yl)ethyl)-1H-benzo[d]imidazol-5-yl)-3,5-dimethylisoxazole

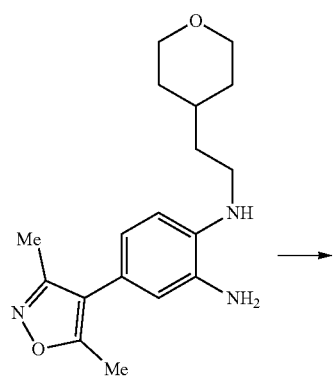

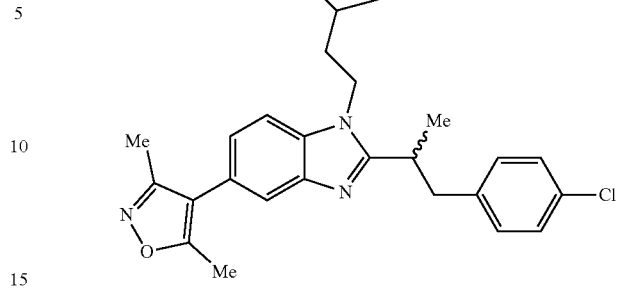

DIPEA (0.166 mL, 0.951 mmol) was added to a solution of 4-(3,5-dimethylisoxazol-4-yl)-N1-(2-(tetrahydro-2H-pyran-4-yl)ethyl)benzene-1,2-diamine (0.12 g, 0.380 mmol), 3-(4-chlorophenyl)-2-methylpropanoic acid (0.091 g, 0.457 mmol) and HATU (0.203 g, 0.533 mmol) in DMF (2 mL, 25.8 mmol) at 0° C., allowed to warm to room temperature and stirred at RT for 48 h. The reaction was diluted with EtOAc (30 mL), washed with aqueous saturated NaHCO3 (20 mL), water (20 mL) and brine (10 mL), dried (MgSO$_4$), filtered and evaporated in vacuo to give the amide intermediate, which was redissolved in acetic acid (3 mL, 52.4 mmol) and stirred at 80° C. for 16 h. The solvent was evaporated in vacuo, azeotroped with toluene (20 mL) and the residue purified by preparative HPLC (Gilson, Basic (0.1% Ammonium Bicarbonate), Basic, Waters X-Bridge Prep-C18, 5 μm, 19×50 mm column, 30-60% MeCN in Water) then by chromatography on the Companion (40 g column, 0-30% (20% MeOH/DCM) in DCM, loaded in DCM) to give 4-(2-(1-(4-chlorophenyl)propan-2-yl)-1-(2-(tetrahydro-2H-pyran-4-yl)ethyl)-1H-benzo[d]imidazol-5-yl)-3,5-dimethylisoxazole (42 mg, 22%) as a white foam; Rt 1.86 min (Method 1), m/z 478 (M+H)+(ES+); 1H NMR (d6-DMSO) δ: 7.60 (1H, dd), 7.53 (1H, d), 7.28 (2H, m), 7.17 (3H, m), 4.10 (2H, m), 3.83 (2H, m), 3.41 (1H, m), 3.29-3.14 (3H, m), 2.98 (1H, dd), 2.41 (3H, s), 2.24 (3H, s), 1.65-1.41 (4H, m), 1.33 (3H, d), 1.25-1.11 (3H, m)

Example 12: 4-(2-(1-(3-chloro-4-(trifluoromethoxy)phenyl)propan-2-yl)-5-(3,5-dimethylisoxazol-4-yl)-1H-benzo[d]imidazol-1-yl)tetrahydro-2H-thiopyran 1,1-dioxide

4-(2-(1-(3-chloro-4-(trifluoromethoxy)phenyl)propan-2-yl)-5-(3,5-dimethylisoxazol-4-yl)-1H-benzo[d]imidazol-1-yl)tetrahydro-2H-thiopyran 1,1-dioxide

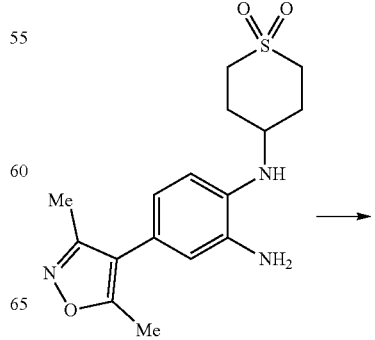

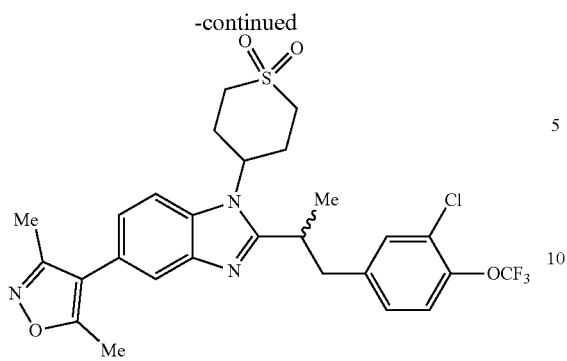
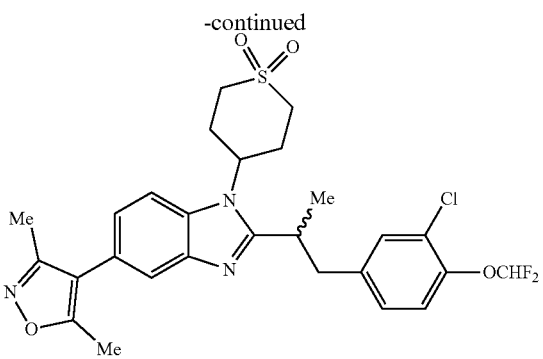

4-((2-amino-4-(3,5-dimethylisoxazol-4-yl)phenyl)amino)tetrahydro-2H-thiopyran 1,1-dioxide (120 mg, 0.340 mmol) and 3-(3-chloro-4-(trifluoromethoxy)phenyl)-2-methylpropanoic acid (108 mg, 0.374 mmol) were dissolved in dry DMF (4 mL, 51.7 mmol) under nitrogen. HATU (155 mg, 0.408 mmol) was added, followed by DIPEA (0.178 mL, 1.020 mmol) and the reaction mixture stirred at RT over the weekend. The reaction mixture was concentrated in vacuo, the residue was dissolved in EtOAc (50 mL), washed with 1M HCl (20 mL), water (20 mL), sat. K2CO3 (20 mL), water (20 mL), brine (20 mL), dried over MgSO4, filtered and concentrated in vacuo, dried azeotropically with Et₂O to give the amide intermediate, which was redissolved in AcOH (6 mL, 105 mmol) under nitrogen and heated to 100° C. for 2.5 h, then warmed to 110° C. for 48 hours. The reaction mixture was cooled to RT, concentrated in vacuo, dried azeotropically with PhMe, then Et₂O. The crude product was purified by chromatography on the Companion (40 g column, 1-3% MeOH in DCM, dry loaded) then by preparative HPLC (Gilson, Acidic (0.1% Formic acid), Acidic, Waters X-Select Prep-C18, 5 µm, 19×50 mm column, 30-60% MeCN in Water) to give 4-(2-(1-(3-chloro-4-(trifluoromethoxy)phenyl)propan-2-yl)-5-(3,5-dimethylisoxazol-4-yl)-1H-benzo[d]imidazol-1-yl)tetrahydro-2H-thiopyran 1,1-dioxide (84 mg, 40%) as a off-white solid; Rt 2.21 min (Method 1), m/z 582 (M+H)+(ES+); 1H NMR (d6-DMSO) δ: 7.67-7.62 (2H, m), 7.57 (1H, d), 7.47 (1H, dd), 7.32 (1H, dd), 7.24 (1H, dd), 4.95 (1H, tt), 3.70-3.48 (3H, m), 3.22 (1H, dd), 3.22-3.12 (2H, m), 3.07 (1H, dd), 2.95-2.75 (2H, m), 2.42 (3H, s), 2.24 (3H, s), 2.24-2.14 (1H, m), 1.85-1.73 (1H, m), 1.28 (3H, d).

Example 13: 4-(2-(1-(3-chloro-4-(difluoromethoxy)phenyl)propan-2-yl)-5-(3,5-dimethylisoxazol-4-yl)-1H-benzo[d]imidazol-1-yl)tetrahydro-2H-thiopyran 1,1-dioxide 4-(2-(1-(3-chloro-4-(difluoromethoxy)phenyl)propan-2-yl)-5-(3,5-dimethylisoxazol-4-yl)-1H-benzo[d]imidazol-1-yl)tetrahydro-2H-thiopyran 1,1-dioxide

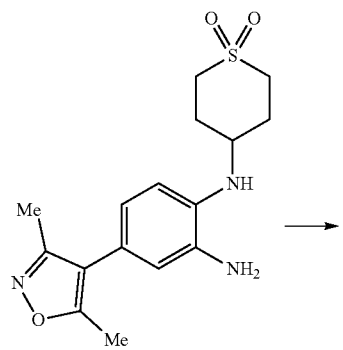

4-((2-amino-4-(3,5-dimethylisoxazol-4-yl)phenyl)amino)tetrahydro-2H-thiopyran 1,1-dioxide (120 mg, 0.340 mmol) and 3-(3-chloro-4-(difluoromethoxy)phenyl)-2-methylpropanoic acid (102 mg, 0.374 mmol) were dissolved in dry DMF (4 mL, 51.7 mmol) under nitrogen. HATU (155 mg, 0.408 mmol) was added, followed by DIPEA (0.178 mL, 1.020 mmol) and the reaction mixture stirred at RT overnight. The reaction mixture was concentrated in vacuo, the residue was dissolved in EtOAc (50 mL), washed with 1M HCl (20 mL), water (20 mL), sat. K₂CO₃ (20 mL), water (20 mL), brine (20 mL), dried over MgSO4, filtered and concentrated in vacuo, dried azeotropically with Et2O to give the amide intermediate, which was dissolved in AcOH (6 mL, 105 mmol) under nitrogen and heated to 110° C. for 2 days. The reaction mixture was cooled to RT, concentrated in vacuo, dried azeotropically with PhMe then Et₂O. The crude product was purified by chromatography on the Companion (40 g column, 0-3% MeOH in DCM, dry loaded) and then by preparative HPLC (Gilson, Acidic (0.1% Formic acid), Acidic, Waters X-Select Prep-C18, 5 µm, 19×50 mm column, 25-55% MeCN in Water) to give 4-(2-(1-(3-chloro-4-(difluoromethoxy)phenyl)propan-2-yl)-5-(3,5-dimethylisoxazol-4-yl)-1H-benzo[d]imidazol-1-yl)tetrahydro-2H-thiopyran 1,1-dioxide (71 mg, %) as a white solid; Rt 2.01 min (Method 1); m/z 564 (M+H)+(ES+); 1H NMR (d6-DMSO) δ: 7.59-7.53 (2H, m), 7.28-7.22 (3H, m), 7.21 (1H, t), 4.94 (1H, tt), 3.73-3.63 (1H, m), 3.62 (1H, dt), 3.51 (1H, dt), 3.25-3.14 (2H, m), 3.17 (1H, dd), 3.04 (1H, dd), 2.93-2.73 (2H, m), 2.41 (3H, s), 2.24 (3H, s), 2.19 (1H, br d), 1.71 (1H, br d), 1.29 (3H, d).

Example 14: 4-(2-(3,4-dichlorophenethyl)-5-(3,5-dimethylisoxazol-4-yl)-1H-benzo[d]imidazol-1-yl)tetrahydro-2H-thiopyran 1,1-dioxide 4-(2-(3,4-dichlorophenethyl)-5-(3,5-dimethylisoxazol-4-yl)-1H-benzo[d]imidazol-1-yl)tetrahydro-2H-thiopyran 1,1-dioxide

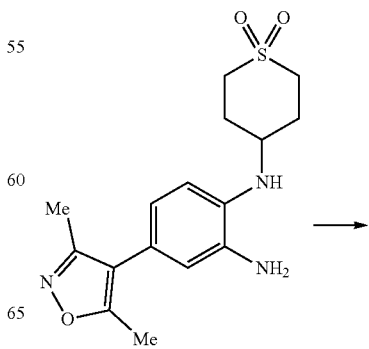

77
-continued

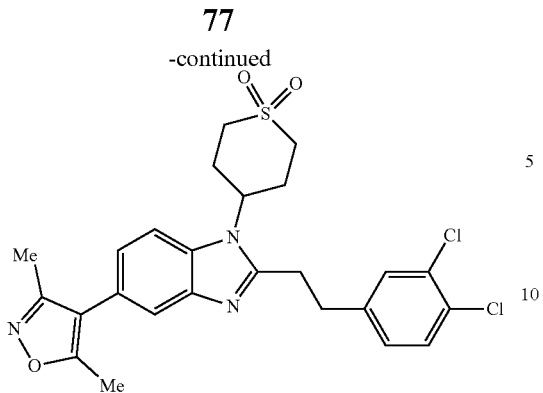

4-((2-amino-4-(3,5-dimethylisoxazol-4-yl)phenyl)amino) tetrahydro-2H-thiopyran 1,1-dioxide (120 mg, 0.340 mmol) and 3-(3,4-dichlorophenyl)propanoic acid (82 mg, 0.374 mmol) were dissolved in dry DMF (4 mL, 51.7 mmol) under nitrogen, HATU (155 mg, 0.408 mmol) was added, followed by DIPEA (0.178 mL, 1.020 mmol) and the reaction mixture stirred at RT for 5 h. The reaction mixture was concentrated in vacuo, the residue was dissolved in EtOAc (50 mL), washed with 1M HCl (20 mL), water (20 mL), saturated aqueous $K_2CO_3$ (20 mL), water (20 mL), brine (20 mL), dried over MgSO4, filtered and concentrated in vacuo to give the amide intermediate, which was redissolved in AcOH (5 mL, 87 mmol) under nitrogen and heated to 90° C. overnight. The reaction mixture was cooled to RT, concentrated in vacuo, dried azeotropically with toluene, then $Et_2O$. The crude product was purified by chromatography on the Companion (40 g Grace column, 0-4% MeOH in DCM) then by preparative HPLC (Gilson, Acidic (0.1% Formic acid), Acidic, Waters X-Select Prep-C18, 5 μm, 19×50 mm column, 20-50% MeCN in Water) to afford 4-(2-(3,4-dichlorophenethyl)-5-(3,5-dimethylisoxazol-4-yl)-1H-benzo[d]imidazol-1-yl)tetrahydro-2H-thiopyran 1,1-dioxide (73 mg, 58%) as a white solid; Rt 2.23 min (Method 2), m/z 518 (M+H)+(ES+); 1H NMR (d6-DMSO) δ: 7.76 (1H, d), 7.68 (1H, d), 7.65 (2H, d), 7.43 (1H, dd), 7.31 (1H, dd), 4.96 (1H, tt), 3.61 (2H, dt), 3.36-3.28 (3H, m), 3.28-3.21 (3H, m), 2.91 (2H, q), 2.47 (3H, s), 2.30 (3H, s), 2.26 (2H, br d).

Example 15: 4-(2-(4-ethylphenethyl)-1-(3-(methylsulfonyl)propyl)-1H-benzo[d]imidazol-5-yl)-3,5-dimethylisoxazole 4-(2-(4-ethylphenethyl)-1-(3-(methylsulfonyl)propyl)-1H-benzo[d]imidazol-5-yl)-3,5-dimethylisoxazole

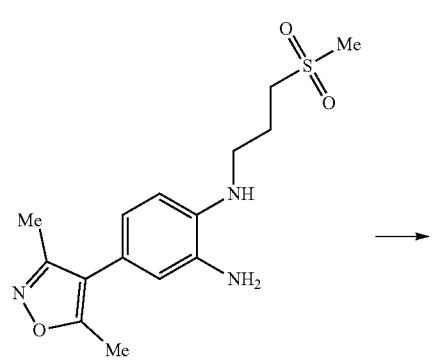

78
-continued

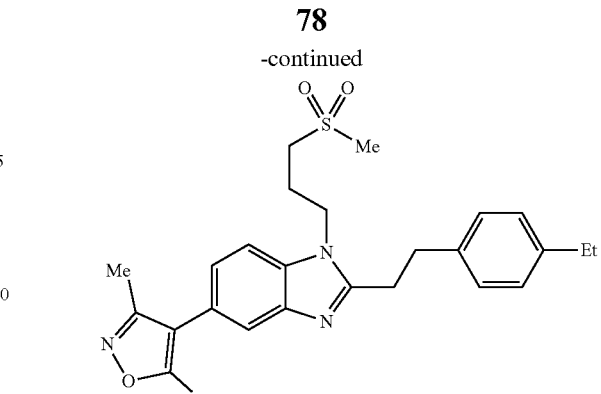

DIPEA (0.194 mL, 1.113 mmol) was added dropwise to a stirring solution of 4-(3,5-dimethylisoxazol-4-yl)-N1-(3-(methylsulfonyl)propyl)benzene-1,2-diamine (0.12 g, 0.371 mmol), 3-(4-ethylphenyl)propanoic acid (0.079 g, 0.445 mmol) and 2-(3H-[1,2,3]triazolo[4,5-b]pyridin-3-yl)-1,1,3,3-tetramethylisouronium hexafluorophosphate(V) (0.310 g, 0.816 mmol) in DMF (10 mL) and the resulting brown solution was stirred at room temperature for 16 hours. The mixture was diluted with water and extracted with diethyl ether (2×150 mL). The organic layer was dried (MgSO$_4$), filtered and evaporated under reduced pressure to give intermediate as a brown oil. The oil was dissolved in acetic acid (2 mL) and heated to 90° C. for 16 hours. The mixture was evaporated to dryness and the residue was purified by preparative HPLC (Waters, Acidic (0.1% Formic acid), Acidic, Waters X-Select Prep-C18, 5 μm, 19×50 mm column, 10-40% MeCN in Water) to afford 4-(2-(4-ethylphenethyl)-1-(3-(methylsulfonyl)propyl)-1H-benzo[d]imidazol-5-yl)-3,5-dimethylisoxazole (51 mg, 29%) as a light tan solid; Rt 1.65 min (Method 1), m/z 466 (M+H)+(ES+); 1H NMR (d6-DMSO) δ: 7.68-7.62 (m, 1H), 7.62-7.58 (m, 1H), 7.27-7.23 (m, 2H), 7.21 (dd, 1H), 7.17-7.11 (m, 2H), 4.34 (t, 2H), 3.23 (q, 2H), 3.19-3.10 (m, 4H), 3.00 (s, 3H), 2.57 (q, 2H), 2.41 (s, 3H), 2.24 (s, 3H), 2.19-2.04 (m, 2H), 1.17 (t, 3H).

Example 16: 4-(2-(2-(1H-pyrrolo[2,3-b]pyridin-3-yl)ethyl)-1-(tetrahydro-2H-pyran-4-yl)-1H-benzo[d]imidazole-5-yl)-3,5-dimethylisoxazole 4-(2-(2-(1H-pyrrolo[2,3-b]pyridin-3-yl)ethyl)-1-(tetrahydro-2H-pyran-4-yl)-1H-benzo[d]imidazole-5-yl)-3,5-dimethylisoxazole

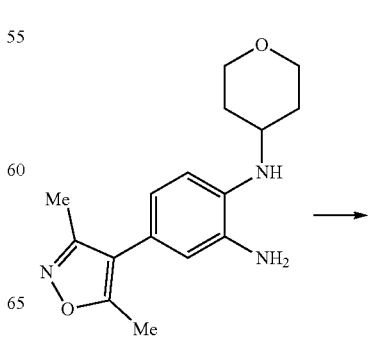

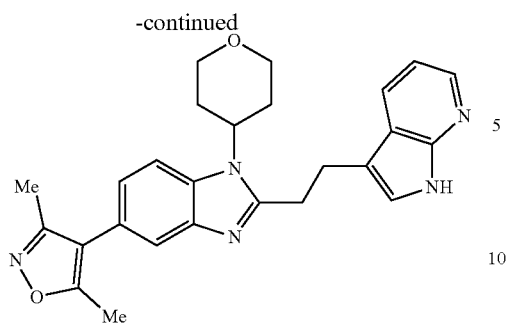

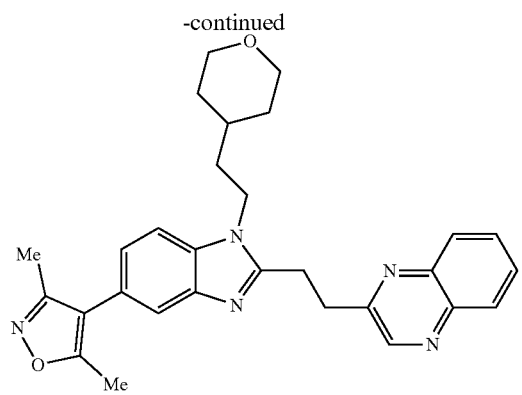

DIPEA (0.218 mL, 1.253 mmol) was added dropwise to a stirring solution of 4-(3,5-dimethylisoxazol-4-yl)-N1-(tetrahydro-2H-pyran-4-yl)benzene-1,2-diamine (0.12 g, 0.418 mmol), 3-(1H-pyrrolo[2,3-b]pyridin-3-yl)propanoic acid (0.095 g, 0.501 mmol) and 2-(3H-[1,2,3]triazolo[4,5-b]pyridin-3-yl)-1,1,3,3-tetramethylisouronium hexafluorophosphate(V) (0.349 g, 0.919 mmol) in DMF (3 mL) and the resulting brown solution was stirred at room temperature for 16 hours. The mixture was diluted with water and extracted with ethyl acetate (50 mL) (×2). The organic layer was dried (MgSO4), filtered and evaporated under pressure. The crude product was purified by chromatography on the Companion (12 g column, 0-10% MeOH in DCM) to afford the amide intermediate, which was dissolved in 4M HCl in dioxane (2 mL) and heated to 60° C. for 2 hours. The crude product was purified by chromatography on silica gel (12 g column, 0-10% MeOH in DCM) then by preparative HPLC (Waters, Basic (0.1% Ammonium Bicarbonate), Basic, Waters X-Bridge Prep-C18, 5 µm, 19×50 mm column, 25-55% MeCN in Water) to afford 4-(2-(2-(1H-pyrrolo[2,3-b]pyridin-3-yl)ethyl)-1-(tetrahydro-2H-pyran-4-yl)-1H-benzo[d]imidazol-5-yl)-3,5-dimethylisoxazole (14 mg, 7.5%) as a cream solid; Rt 1.81 min (Method 2), m/z 442 (M+H)+ (ES+); 1H NMR (d6-DMSO) δ: 11.29 (s, 1H), 8.13 (dd, 1H), 7.97 (dd, 1H), 7.60 (d, 1H), 7.52 (d, 1H), 7.23 (d, 1H), 7.06 (dd, 1H), 6.99 (dd, 1H), 4.48-4.31 (m, 1H), 3.85 (dd, 2H), 3.27 (m, 6H), 2.34 (s, 3H), 2.25 (td, 2H), 2.17 (s, 3H), 1.55-1.42 (m, 2H).

Example 17: 3,5-dimethyl-4-(2-(2-(quinoxalin-2-yl)ethyl)-1-(2-(tetrahydro-2H-pyran-4-yl)ethyl)-1H-benzo[d]imidazol-5-yl)isoxazole 3,5-dimethyl-4-(2-(2-(quinoxalin-2-yl)ethyl)-1-(2-(tetrahydro-2H-pyran-4-yl)ethyl)-1H-benzo[d]imidazol-5-yl)isoxazole

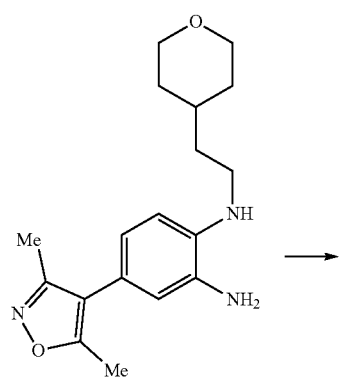

4M HCl in dioxane (2 mL, 8.00 mmol) and 1M aqueous HCl (0.2 mL, 0.200 mmol) were added to N-(5-(3,5-dimethylisoxazol-4-yl)-2-((2-(tetrahydro-2H-pyran-4-yl)ethyl)amino)phenyl)-3-(quinoxalin-2-yl)propanamide (60 mg, 0.120 mmol) and the solution stirred at 60° C. for 5 h. The solution was evaporated in vacuo, azeotroped with toluene (20 mL) and the residue purified by preparative HPLC (Gilson, Basic (0.1% Ammonium Bicarbonate), Basic, Waters X-Bridge Prep-C18, 5 µm, 19×50 mm column, 40-60% MeCN in Water) to give 3,5-dimethyl-4-(2-(2-(quinoxalin-2-yl)ethyl)-1-(2-(tetrahydro-2H-pyran-4-yl)ethyl)-1H-benzo[d]imidazol-5-yl) isoxazole (30 mg, 52%) as a light brown foam; Rt 1.56 min (Method 1), m/z 482 (M+H)+(ES+); 1H NMR (d6-DMSO) δ: 11.29 (s, 1H), 8.13 (dd, 1H), 7.97 (dd, 1H), 7.60 (d, 1H), 7.52 (d, 1H), 7.23 (d, 1H), 7.06 (dd, 1H), 6.99 (dd, 1H), 4.48-4.31 (m, 1H), 3.85 (dd, 2H), 3.27 (m, 6H), 2.34 (s, 3H), 2.25 (td, 2H), 2.17 (s, 3H), 1.55-1.42 (m, 2H).

Example 18: 2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide tert-butyl 2-((4-(3,5-dimethylisoxazol-4-yl)-2-nitrophenyl)amino)acetate

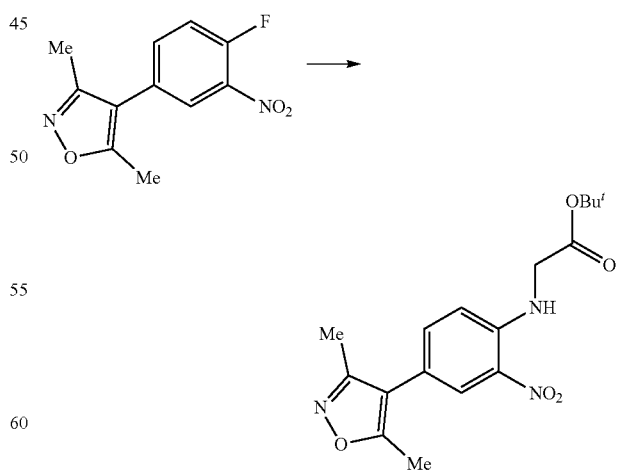

tert-butyl 2-aminoacetate hydrochloride (3.54 g, 21.10 mmol) was dissolved in dry THF (50 mL, 610 mmol) and TEA (6.30 mL, 45.2 mmol) and cooled to 0° C. 4-(4-fluoro-3-nitrophenyl)-3,5-dimethylisoxazole (4.45 g, 15.07 mmol)

was added and the reaction was heated to 70 C for 16 hours. The reaction mixture was poured onto water (300 mL) and filtered under vacuum. The solid was washed with water (300 mL), followed by isohexane (300 mL). The crude product was purified by chromatography on silica gel (80 g column, 0-20% ethyl acetate in isohexane) to afford tert-butyl 2-((4-(3,5-dimethylisoxazol-4-yl)-2-nitrophenyl)amino)acetate (4.92 g, 75%) as a bright orange solid; m/z 348 (M+H)+(ES+).

2-((4-(3,5-dimethylisoxazol-4-yl)-2-nitrophenyl)amino)acetic acid

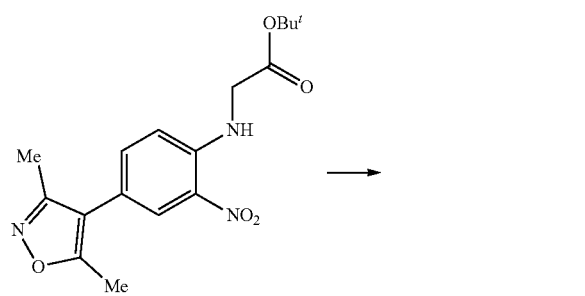

A mixture of tert-butyl 2-((4-(3,5-dimethylisoxazol-4-yl)-2-nitrophenyl)amino)acetate (4.92 g, 14.16 mmol) in DCM (30 mL) was treated with trifluoroacetic acid (1.091 mL, 14.16 mmol) and stirred over the week-end at room temperature. The precipitate was filtered off and washed with iso-hexanes then dried in vacuo to afford 2-((4-(3,5-dimethylisoxazol-4-yl)-2-nitrophenyl)amino)acetic acid (4.01 g, 83%); m/z 292 (M+H)+(ES+).

2-((2-amino-4-(3,5-dimethylisoxazol-4-yl)phenyl)amino)-N-(tetrahydrofuran-3-yl)acetamide

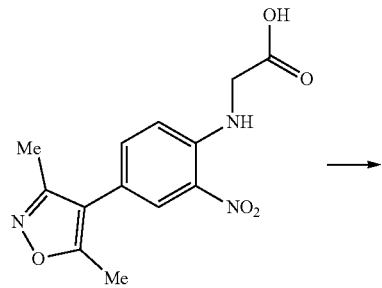

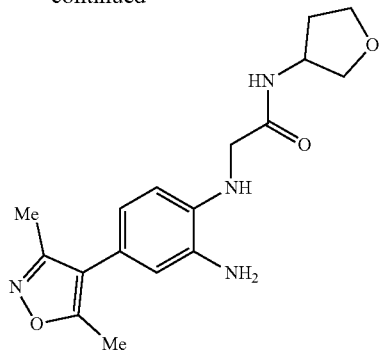

TEA (3.84 mL, 27.5 mmol) was added dropwise to 2-((4-(3,5-dimethylisoxazol-4-yl)-2-nitrophenyl)amino)acetic acid (4.01 g, 13.77 mmol), HATU (6.54 g, 17.21 mmol) and tetrahydrofuran-3-amine hydrochloride (2.127 g, 17.21 mmol) in DMF (10 mL) in a ice-water bath and the resulting dark orange mixture was warmed to room temperature with vigorous stirring for 24 hours. The mixture was treated with brine (20 mL) and filtered off. The orange precipitate was washed with water (3×40 mL) and then purified by chromatography on silica gel (80 g column, 0-100% ethyl acetate in isohexane) to afford 2-((4-(3,5-dimethylisoxazol-4-yl)-2-nitrophenyl)amino)-N-(tetrahydrofuran-3-yl)acetamide (3.37 g, 9.07 mmol, 65.9% yield) as a red oil; m/z 361 (M+H)+(ES+).

2-((2-amino-4-(3,5-dimethylisoxazol-4-yl)phenyl)amino)-N-(tetrahydrofuran-3-yl)acetamide

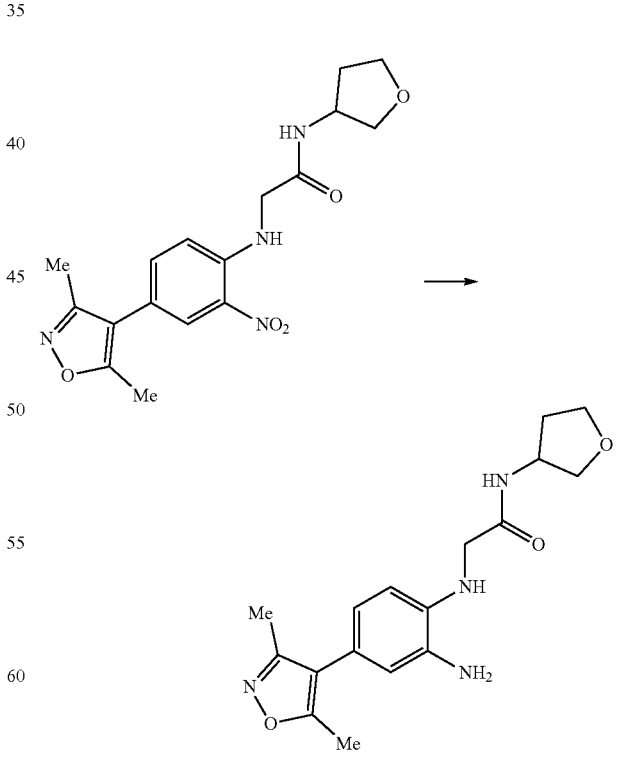

2-((4-(3,5-dimethylisoxazol-4-yl)-2-nitrophenyl)amino)-N-(tetrahydrofuran-3-yl)acetamide (3.37 g, 9.35 mmol) was added to a solution of Sodium dithionite (16.28 g, 94 mmol)

and concentrated aqueous ammonia (7.28 mL, 187 mmol) in THF/water (1:1, 100 mL) and the reaction mixture stirred at RT for 2 hours. The reaction mixture was concentrated in vacuo to remove the organics and the bulk of the aqueous. The residue was partitioned between EtOAc (200 mL) and brine (40 mL), the phases separated and the organics dried over MgSO$_4$, filtered and concentrated in vacuo. The crude product was purified by chromatography on silica gel (80 g column, 0-10% DCM in MeOH) to afford 2-((2-amino-4-(3,5-dimethylisoxazol-4-yl)phenyl)amino)-N-(tetrahydrofuran-3-yl)acetamide (1.81 g, 56%) as a pink foam; m/z 331 (M+H)+(ES+).

2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide

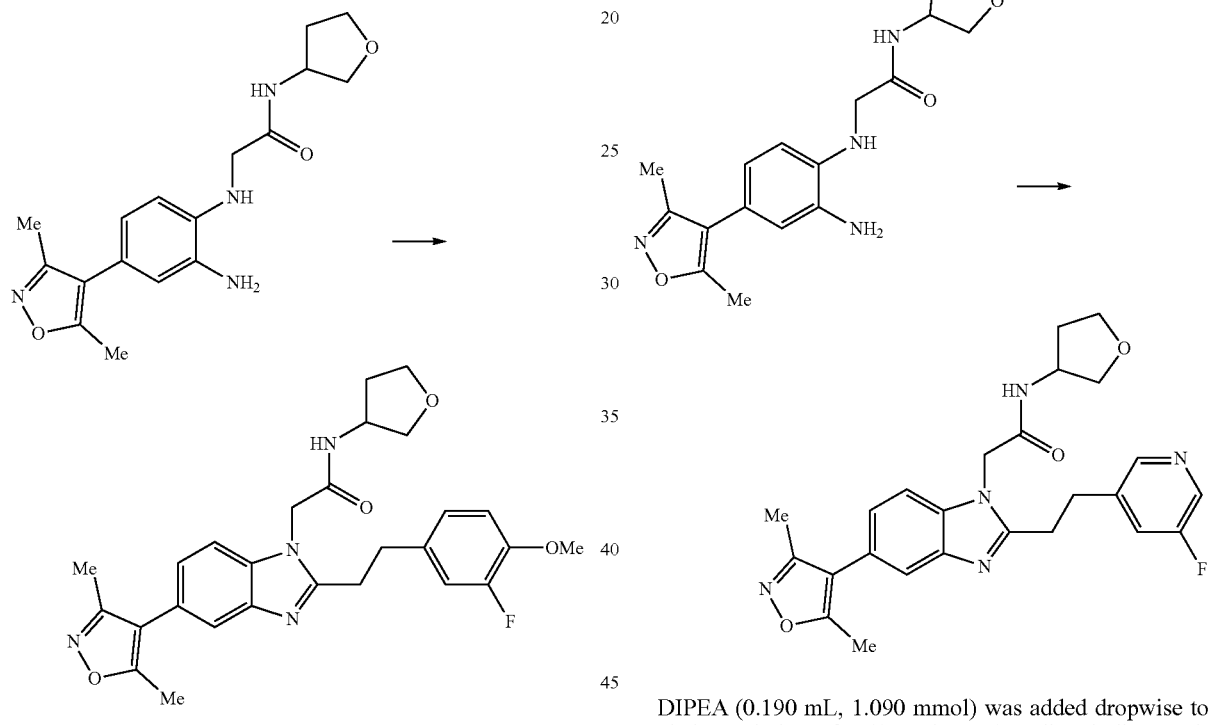

DIPEA (0.190 mL, 1.090 mmol) was added dropwise to a stirring solution of 2-((2-amino-4-(3,5-dimethylisoxazol-4-yl)phenyl)amino)-N-(tetrahydrofuran-3-yl)acetamide (0.12 g, 0.363 mmol), 3-(3-fluoro-4-methoxyphenyl)propanoic acid (0.101 g, 0.509 mmol) and 2-(3H-[1,2,3]triazolo[4,5-b]pyridin-3-yl)-1,1,3,3-tetramethylisouronium hexafluorophosphate(V) (0.304 g, 0.799 mmol) in DMF (10 mL) and the resulting brown solution was stirred at room temperature for 16 hours. The mixture was diluted with water and extracted with diethyl ether (2×150 mL). The organic layer was dried (MgSO4), filtered and evaporated under pressure to give intermediate as a brown oil. The oil was dissolved in 4M HCl in dioxane (1 mL) and heated to 50° C. for 2 hours. The mixture was evaporated to dryness and the crude product was purified by preparative HPLC (Waters, Acidic (0.1% Formic acid), Acidic, Waters X-Select Prep-C18, 5 µm, 19×50 mm column, 10-40% MeCN in Water) to afford 2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide (39 mg, 21%) as a white solid; Rt 1.89 min (Method 2); m/z 493 (M+H)+(ES+); 1H NMR (d6-DMSO) δ: 8.75 (d, 1H), 7.57 (d, 1H), 7.53-7.43 (m, 1H), 7.26-7.15 (m, 2H), 7.12-7.02 (m, 2H), 4.92 (s, 2H), 4.27 (ddq, 1H), 3.81 (s, 4H), 3.78-3.66 (m, 2H), 3.52 (dd, 1H), 3.09 (s, 4H), 2.41 (s, 3H), 2.24 (s, 3H), 2.18-2.03 (m, 1H), 1.77 (m, 1H).

Example 19: 2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide 2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide

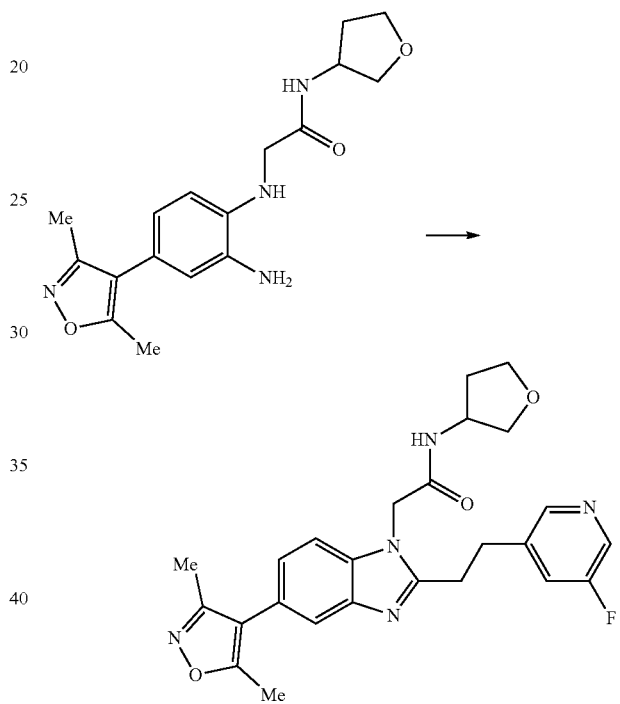

DIPEA (0.190 mL, 1.090 mmol) was added dropwise to a stirring solution of 2-((2-amino-4-(3,5-dimethylisoxazol-4-yl)phenyl)amino)-N-(tetrahydrofuran-3-yl)acetamide (0.12 g, 0.363 mmol), 3-(5-fluoropyridin-3-yl)propanoic acid (0.086 g, 0.509 mmol) and 2-(3H-[1,2,3]triazolo[4,5-b]pyridin-3-yl)-1,1,3,3-tetramethylisouronium hexafluorophosphate(V) (0.304 g, 0.799 mmol) in DMF (10 mL) and the resulting brown solution was stirred at room temperature for 16 hours. The mixture was diluted with water and extracted with diethyl ether (2×150 mL). The organic layer was dried (MgSO4), filtered and evaporated under pressure to give intermediate as a brown oil. The oil was dissolved in 4M HCl in dioxane (1 mL) and heated to 50° C. for 2 hours. The mixture was evaporated to dryness. The crude product was purified by chromatography on the Companion (40 g column, 0-10% MeOH in DCM) then by preparative HPLC (Waters, Basic (0.1% Ammonium Bicarbonate), Basic, Waters X-Bridge Prep-C18, 5 µm, 19×50 mm column, 20-50% MeCN in Water) to afford 2-(5-(3,5-dimethylisoxazol-4-yl)-2-(2-(5-fluoropyridin-3-yl)ethyl)-1H-benzo[d]imidazol-1-yl)-N-(tetrahydrofuran-3-yl)acetamide (23 mg, 13%) as a white solid; Rt 1.61 min (Method 2), m/z 464

(M+H)+(ES+); 1H NMR (d6-DMSO) δ: 8.73 (d, 1H), 8.46-8.37 (m, 2H), 7.74 (ddd, 1H), 7.58 (dd, 1H), 7.49 (dd, 1H), 7.19 (dd, 1H), 4.93 (s, 2H), 4.27 (dh, 1H), 3.84 (dd, 1H), 3.79-3.65 (m, 2H), 3.52 (dd, 1H), 3.31-3.08 (m, 4H), 2.40 (s, 3H), 2.23 (s, 3H), 2.18-2.03 (m, 1H), 1.77 (m, 1H).

Example 20: 2-(5-(3,5-dimethylisoxazol-4-yl)-2-(1-(3-fluoro-4-methoxyphenyl)propan-2-yl)-1H-benzo[d]imidazol-1-yl)-N-(tetrahydrofuran-3-yl)acetamide Tert-butyl 2-((4-bromo-2-nitrophenyl)amino)acetate

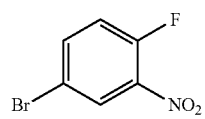  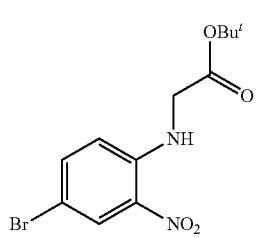

To a mixture of 4-bromo-1-fluoro-2-nitrobenzene (14.17 g, 64.4 mmol) and tert-butyl 2-aminoacetate hydrochloride (13.5 g, 81 mmol) in THF (180 mL) was added TEA (17.96 mL, 129 mmol) in THF (20 mL) dropwise. The resulting orange mixture was stirred at room temperature for 18 hours then water (300 mL) was added. After decantation of the biphasic mixture, a orange precipitate was stirred in iso-hexanes (300 mL) and filtered off and washed with iso-hexanes (200 mL) to give 2-((4-bromo-2-nitrophenyl)amino)acetate as a crystalline orange solid (2.00 g, 9%); m/z 275/277 (M+H-Bu$^t$)+(ES+).

2-((4-bromo-2-nitrophenyl)amino)acetic acid

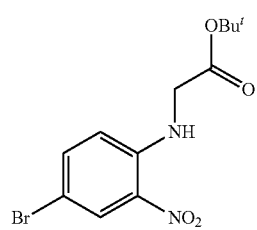

A mixture of tert-butyl 2-((4-bromo-2-nitrophenyl)amino)acetate (2 g, 6.04 mmol) in DCM (10 mL) was treated with trifluoroacetic acid (0.465 mL, 6.04 mmol) and stirred over the week-end at room temperature. The precipitate was filtered off and washed with iso-hexanes then dried in vacuo to afford 2-((4-bromo-2-nitrophenyl)amino)acetic acid (1.57 g, 5.59 mmol, 93% yield) as a yellow solid; m/z 275/277 (M+H)+(ES+).

2-((4-bromo-2-nitrophenyl)amino)-N-(tetrahydrofuran-3-yl)acetamide

 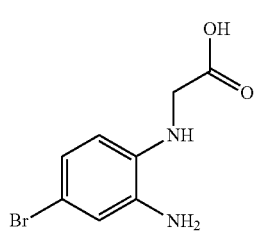

TEA (507 µl, 3.64 mmol) was added dropwise to 2-((4-bromo-2-nitrophenyl)amino)acetic acid (500 mg, 1.818 mmol), HATU (864 mg, 2.272 mmol) and tetrahydrofuran-3-amine (198 mg, 2.272 mmol) in DCM (5 mL) and the resulting dark red mixture was stirred at room temperature for 2 hours. The mixture was treated with sodium hydrogenocarbonate (20 mL) and the precipitate filtered off and washed with water (3×20 mL). Flash chromatography (0-100% EtOAc+1% MeOH in iso-hexanes, 40 g silica) gave 2-((4-bromo-2-nitrophenyl)amino)-N-(tetrahydrofuran-3-yl)acetamide (382 mg, 59%) as a orange solid; m/z 344/346 (M+H)+(ES+).

2-((2-amino-4-bromophenyl)amino)-N-(tetrahydrofuran-3-yl)acetamide

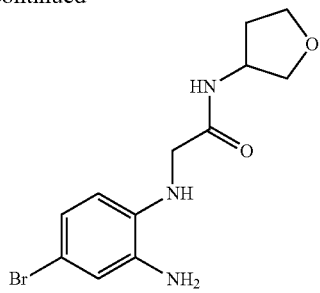

Concentrated aqueous ammonia (1.5 mL, 38.5 mmol) followed by sodium dithionite (8.33 g, 40.7 mmol) were added to 2-((4-bromo-2-nitrophenyl)amino)-N-(tetrahydrofuran-3-yl)acetamide (1.4 g, 4.07 mmol) in THF/water 1:1 (250 mL). The mixture was stirred for 15 mn then extracted into EtOAc (200 mL). The organic layer was washed with brine (100 mL), dried (MgSO4) and evaporated in vacuo. Flash chromatography (0-4% MeOH in DCM) gave 2-((2-amino-4-bromophenyl)amino)-N-(tetrahydrofuran-3-yl)acetamide (534 mg, 41%) as a red oil; m/z 314/316 (M+H)+ (ES+).

2-((2-amino-4-(3,5-dimethylisoxazol-4-yl)phenyl)amino)-N-(tetrahydrofuran-3-yl)acetamide

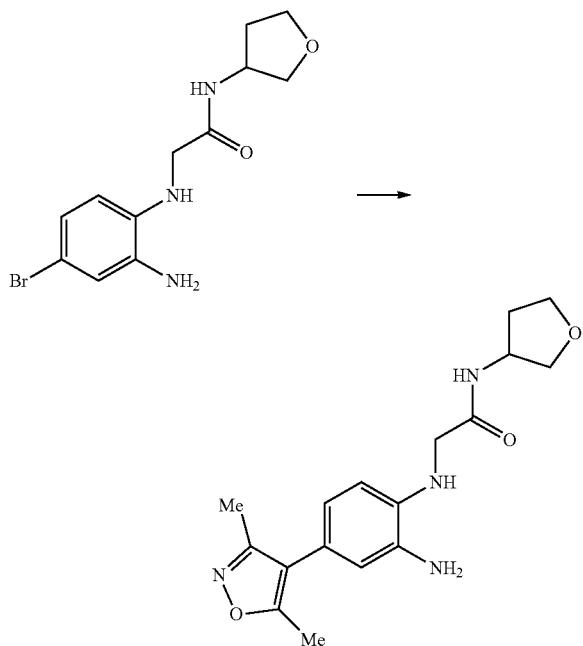

Tetrakis(triphenylphosphine)palladium(0) (183 mg, 0.158 mmol), 2-((2-amino-4-bromophenyl)amino)-N-(tetrahydrofuran-3-yl)acetamide (534 mg, 1.581 mmol), sodium carbonate (503 mg, 4.74 mmol), (3,5-dimethylisoxazol-4-yl)boronic acid (401 mg, 2.85 mmol) in 1,4-dioxane/water (4:1, 5 mL) was degassed with nitrogen then stirred at 80° C. for 18 hours. The mixture was cooled down to room temperature, washed with EtOAc (40 mL). The organic layer was washed with brine (300 mL), dried (MgSO4) and evaporated in vacuo. The crude product was purified by chromatography on silica gel (12 g column, 0-10% MeOH in DCM then 10% MeOH+1% NH3 in DCM) afforded 2-((2-amino-4-(3,5-dimethylisoxazol-4-yl)phenyl)amino)-N-(tetrahydrofuran-3-yl)acetamide (312 mg, 58%); m/z 331 (M+H)+ (ES+).

2-(5-(3,5-dimethylisoxazol-4-yl)-2-(1-(3-fluoro-4-methoxyphenyl)propan-2-yl)-1H-benzo[d]imidazol-1-yl)-N-(tetrahydrofuran-3-yl)acetamide

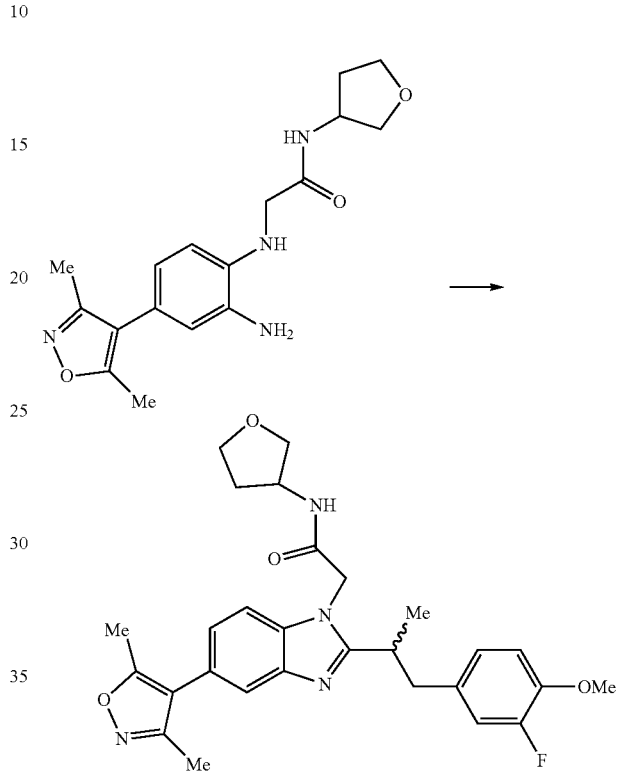

HATU (432 mg, 1.135 mmol) was added portionwise to 2-((2-amino-4-(3,5-dimethylisoxazol-4-yl)phenyl)amino)-N-(tetrahydrofuran-3-yl)acetamide (300 mg, 0.908 mmol), TEA (253 µl, 1.816 mmol) and 3-(3-fluoro-4-methoxyphenyl)-2-methylpropanoic acid (193 mg, 0.908 mmol) in DCM (5 mL) and the resulting dark red mixture was stirred at room temperature for 2 hours. The mixture was treated with sodium hydrogenocarbonate (20 mL) and the precipitate dissolved in EtOAc (20 mL) and washed with water (3×20 mL). The organic layer was dried (MgSO4) and evaporated in vacuo to give the amide intermediate, which was dissolved in 1,4-dioxane (5 mL) and 1M HCl (5 mL) added. The mixture was stirred at room temperature for 2 hours then at 60° C. over the week-end. The mixture was extracted into EtOAc (10 mL) and the organic extracts washed with brine (10 mL), dried (MgSO4) and evaporated in vacuo. The crude product was purified by chromatography on silica gel (4 g column, 0-10% MeOH in DCM) to afford 2-(5-(3,5-dimethylisoxazol-4-yl)-2-(1-(3-fluoro-4-methoxyphenyl)propan-2-yl)-1H-benzo[d]imidazol-1-yl)-N-(tetrahydrofuran-3-yl)acetamide (36 mg, 7%) as a light yellow glass; Rt 1.54 min (Method 1), m/z 507 (M+H)+(ES+); 1H NMR (d6-DMSO) δ: 9.09 (d, 1H), 7.85 (d, 1H), 7.74 (d, 1H), 7.52 (d, 1H), 7.15 (dd, 1H), 7.10-6.93 (m, 2H), 5.23 (q, 2H), 4.27 (d, 1H), 3.86 (q, 2H), 3.71 (dddd, 4H), 3.60-3.46 (m, 3H), 3.23-3.10 (m, 1H), 2.99 (dd, 1H), 2.43 (s, 3H), 2.24 (s, 3H), 2.13 (dqd, 1H), 1.81 (s, 1H), 1.37 (d, 3H).

Example 22: 4-(2-(1-(3-fluoro-4-(trifluoromethoxy) phenyl)propan-2-yl)-1-(2-(tetrahydro-2H-pyran-4-yl) ethyl)-1H-benzo[d]imidazol-5-yl)-3,5-dimethylisoxazole

Methyl 3-(3-fluoro-4-(trifluoromethoxy)phenyl)-2-methylpropanoate

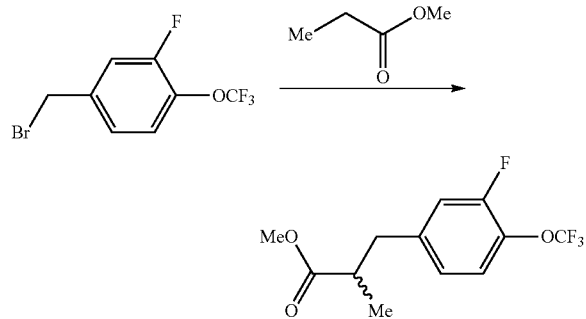

Diisopropylamine (1.078 ml, 7.69 mmol) was dissolved in dry THF (20 ml, 244 mmol) under nitrogen and cooled to −78° C., 2.5M butyllithium in hexanes (3.08 ml, 7.69 mmol) was added and the reaction mixture warmed to 0° C. over 30 min. The reaction mixture was cooled to −78° C. and a solution of methyl propionate (0.353 ml, 3.66 mmol) in dry THF (5 ml, 61.0 mmol) was added dropwise over 15 mn and the reaction mixture stirred at −78° C. for 15 mn. 1,3-Dimethyltetrahydropyrimidin-2(1H)-one (0.443 ml, 3.66 mmol) was added at −78° C. and the reaction stirred for 10 mn. A solution of 4-(bromomethyl)-2-fluoro-1-(trifluoromethoxy)benzene (0.610 ml, 3.66 mmol) in dry THF (5 ml, 61.0 mmol) was added dropwise over 20 mn maintaining the reaction temperature at −78° C. and the reaction mixture allowed slowly to warm up to RT overnight. The reaction was slowly quenched with 1M aqueous HCl (20 ml) whilst maintaining the temperature below 10° C. and then extracted with EtOAc (3×30 ml). The combined extracts were washed with water (30 ml) and brine (20 ml), dried (MgSO$_4$), filtered and evaporated in vacuo. The residual oil was purified by flash chromatography, first on a 80 g column (0-30% EtOAc in isohexane, loaded in toluene) then on a 80 g column (0-20% EtOAc in isohexane, loaded in toluene) to give methyl 3-(3-fluoro-4-(trifluoromethoxy)phenyl)-2-methylpropanoate (0.52 g, 48%) as a colourless oil; Rt 2.54 min (Method 1), m/z 281 (M+H)+(ES+).

3-(3-Fluoro-4-(trifluoromethoxy)phenyl)-2-methylpropanoic acid

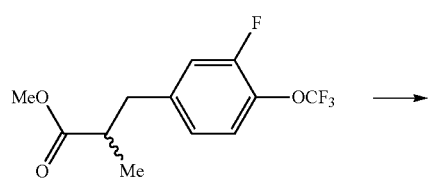

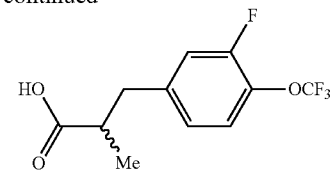

A solution of lithium hydroxide monohydrate (0.150 g, 3.57 mmol) in water (5 ml, 278 mmol) was added to a solution of methyl 3-(3-fluoro-4-(trifluoromethoxy)phenyl)-2-methylpropanoate (0.5 g, 1.784 mmol) in THF (10 ml, 122 mmol) and the reaction stirred at RT for 3 h. Cooled to 0° C., acidified with 1M HCl (5.35 ml, 5.35 mmol), extracted with EtOAc (3×20 ml), the combined extracts washed with brine (10 ml), dried (MgSO4), filtered and evaporated in vacuo to give 3-(3-fluoro-4-(trifluoromethoxy)phenyl)-2-methylpropanoic acid (0.44 g, 88%); Rt 2.20 min (Method 1), m/z 265 (M+H)+(ES+).

N-(5-(3,5-Dimethylisoxazol-4-yl)-2-((2-(tetrahydro-2H-pyran-4-yl)ethyl)amino)phenyl)-3-(3-fluoro-4-(trifluoromethoxy)phenyl)-2-methylpropanamide

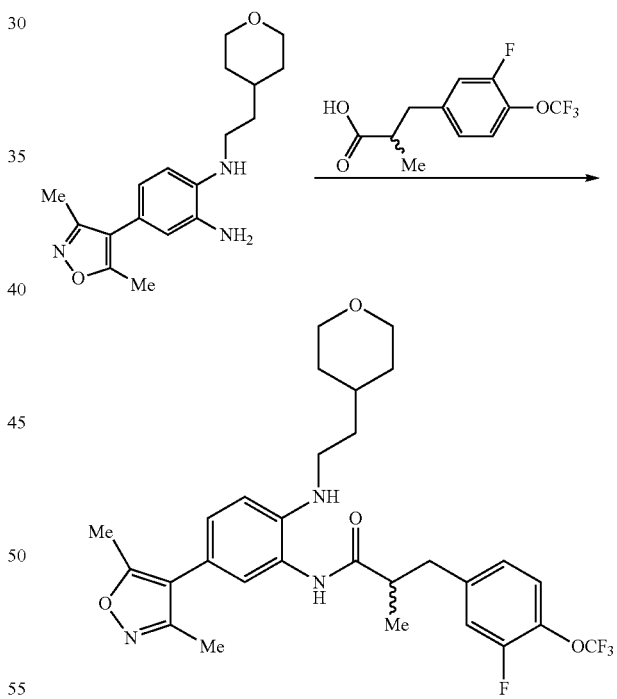

DIPEA (0.166 ml, 0.951 mmol) was added to a solution of 4-(3,5-dimethylisoxazol-4-yl)-N1-(2-(tetrahydro-2H-pyran-4-yl)ethyl)benzene-1,2-diamine (0.12 g, 0.380 mmol), 3-(3-fluoro-4-(trifluoromethoxy)phenyl)-2-methylpropanoic acid (0.111 g, 0.419 mmol) and HATU (0.188 g, 0.495 mmol) in DMF (1 ml, 12.91 mmol) at 0° C., allowed to attain room temperature and stirred at RT for 20 h. The reaction was diluted with EtOAc (20 ml), washed with aqNaHCO3 (10 ml), water (10 ml) and brine (10 ml), dried (MgSO4), filtered and evaporated in vacuo to give crude N-(5-(3,5-dimethylisoxazol-4-yl)-2-((2-(tetrahydro-2H-pyran-4-yl)ethyl)amino) phenyl)-3-(3-fluoro-4-(trifluoromethoxy)phenyl)-2-methylpropanamide (0.22 g, 0.360 mmol, 95% yield) as a light brown gum; Rt 2.60 min (Method 1), m/z 564 (M+H)+(ES+).

4-(2-(1-(3-Fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole Example 23: 4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide 4-(2-(1-(4-Chlorophenyl)propan-2-yl)-5-(3,5-dimethylisoxazol-4-yl)-1H-benzo[d]imidazol-1-yl)tetrahydro-2H-thiopyran 1,1-dioxide

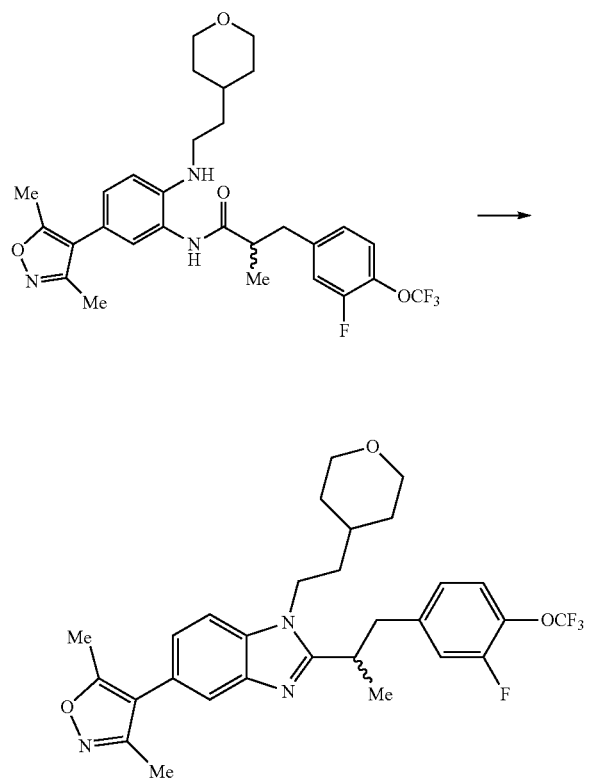

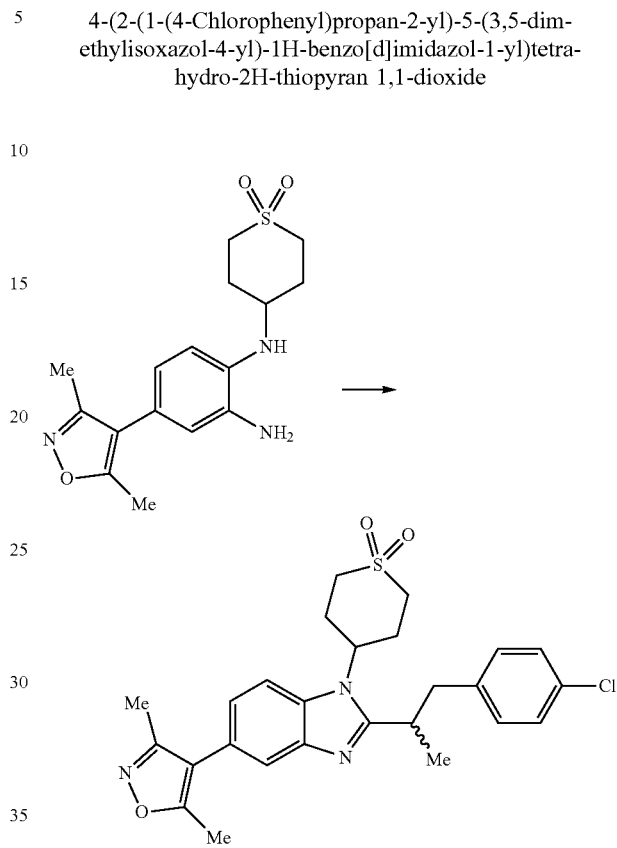

N-(5-(3,5-dimethylisoxazol-4-yl)-2-((2-(tetrahydro-2H-pyran-4-yl)ethyl)amino)phenyl)-3-(3-fluoro-4-(trifluoromethoxy)phenyl)-2-methylpropanamide (210 mg, 0.373 mmol) was dissolved in AcOH (2 mL, 34.9 mmol) and stirred at 90° C. for 8 h. The solution was evaporated in vacuo, azeotroped with toluene (3×30 ml) and the residual gum twice purified by flash chromatography, first on a 40 g column (0-50% (DCM, MeOH, NH₃/80:20:1) in DCM, loaded in DCM) then on another 40 g column (50-100% EtOAc in Hexanes, loaded in toluene) to give 4-(2-(1-(3-fluoro-4-(trifluoromethoxy)phenyl)propan-2-yl)-1-(2-(tetrahydro-2H-pyran-4-yl) ethyl)-1H-benzo[d]imidazol-5-yl)-3,5-dimethylisoxazole (91 mg, 44%) as a colourless gum; Rt 2.09 min (Method 1), m/z 546 (M+H)+(ES+); 1H NMR (DMSO-d6) 7.61 (1H, dd), 7.53 (1H, dd), 7.44-7.37 (2H, m), 7.17 (1H, dd), 7.12 (1H, m), 4.14 (2H, t), 3.83 (2H, m), 3.48 (1H, m), 3.25 (3H, m), 3.05 (1H, dd), 2.41 (3H, s), 2.24 (3H, s), 1.64-1.45 (4H, m), 1.32 (3H, d), 1.34-1.14 (4H, m).

N-ethyl-N-isopropylpropan-2-amine (0.234 ml, 1.342 mmol) was added dropwise to a stirring solution of 4-((2-amino-4-(3,5-dimethylisoxazol-4-yl)phenyl)amino)tetrahydro-2H-thiopyran 1,1-dioxide (0.15 g, 0.447 mmol), 3-(4-chlorophenyl)-2-methylpropanoic acid (0.107 g, 0.537 mmol) and 2-(3H-[1,2,3]triazolo[4,5-b]pyridin-3-yl)-1,1,3,3-tetramethylisouronium hexafluoro phosphate(V) (0.374 g, 0.984 mmol) in DMF (10 mL) and the resulting brown solution was stirred at room temperature for 16 hours. The mixture was diluted with water and extracted with diethyl ether (2×150 mL). The organic layer was dried (MgSO₄), filtered and evaporated under reduced pressure to give the amide intermediate as a brown oil. The oil was dissolved in acetic acid (2 mL) and heated to 90° C. for 32 hours. The mixture was evaporated to dryness and the crude product was purified by preparative HPLC (Waters, Acidic (0.1% Formic acid), Waters X-Select Prep-C18, 5 μm, 19×50 mm column, 20-50% MeCN in Water) to afford 4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide (72 mg, 32%) as a light tan solid; Rt 1.84 min (Method 1), m/z 499 (M+H)+(ES+); 1H NMR (DMSO-d6) δ 7.64 (s, 1H), 7.56 (d, J=8.4 Hz, 1H), 7.37-7.30 (m, 2H), 7.30-7.19 (m, 3H), 4.91 (m, 1H), 3.68-3.54 (m, 2H), 3.54-3.44 (m, 1H), 3.24-3.11 (m, 3H), 3.00 (dd, J=13.5, 7.5 Hz, 1H), 2.95-2.68 (m, 2H), 2.42 (s, 3H), 2.25 (m, 4H), 1.67 (m, 1H), 1.30 (d, J=6.6 Hz, 3H).

Examples 24 and 25: (R)-4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole and (S)-4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole

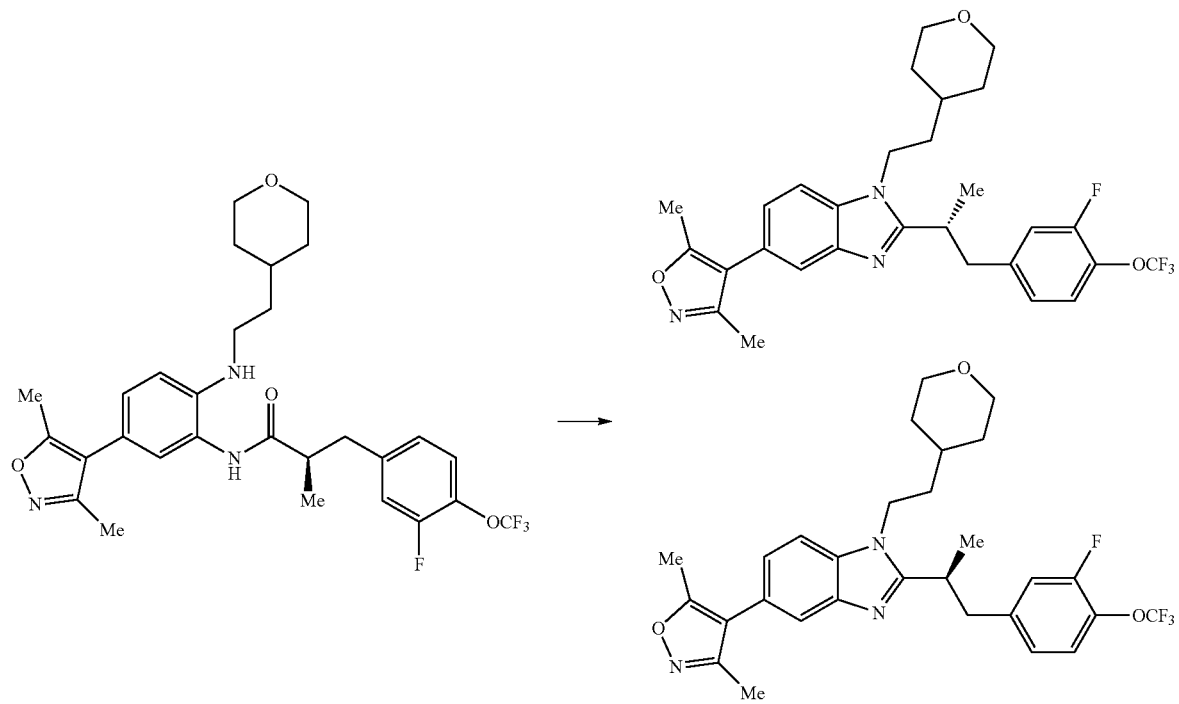 [SMILES: Cc1noc(C)c1-c1ccc(NCCC2CCOCC2)c(NC(=O)[C@H](C)Cc2ccc(OC(F)(F)F)c(F)c2)c1 ; Cc1noc(C)c1-c1ccc2c(c1)nc([C@@H](C)Cc1ccc(OC(F)(F)F)c(F)c1)n2CCC1CCOCC1 ; Cc1noc(C)c1-c1ccc2c(c1)nc([C@H](C)Cc1ccc(OC(F)(F)F)c(F)c1)n2CCC1CCOCC1]

A solution of (R)—N-(5-(3,5-dimethylisoxazol-4-yl)-2-((2-(tetrahydro-2H-pyran-4-yl)ethyl) amino)phenyl)-3-(3-fluoro-4-(trifluoromethoxy)phenyl)-2-methylpropanamide (191 mg, 0.339 mmol) in acetic acid (2 ml) was heated at 80° C. for 24 h, then left to stand at rt for 48 h. The solvent was removed in vacuo and the residue was dissolved in the minimum of DCM. The solution was purified by chromatography (12 g silica, 10-50% ethyl acetate in isohexanes, gradient elution). Product fractions were combined and concentrated in vacuo. The residue was taken up in ether and the solvent removed in vacuo to afford (R)-4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole (109 mg, 58%) as a sticky smear which scratched to a sticky white solid; Rt 2.09 min (Method 1), m/z 546 (M+H)+(ES+); 1H NMR (DMSO-d6) δ 7.61 (1H, dd), 7.53 (1H, dd), 7.44-7.37 (2H, m), 7.17 (1H, dd), 7.12 (1H, m), 4.14 (2H, t), 3.83 (2H, m), 3.48 (1H, m), 3.25 (3H, m), 3.05 (1H, dd), 2.41 (3H, s), 2.24 (3H, s), 1.64-1.45 (4H, m), 1.32 (3H, d), 1.34-1.14 (4H, m).

Examples 26 and 27: 3-(2-((R)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide and 3-(2-((S)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide 3-(2-((R)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide & 3-(2-((S)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide

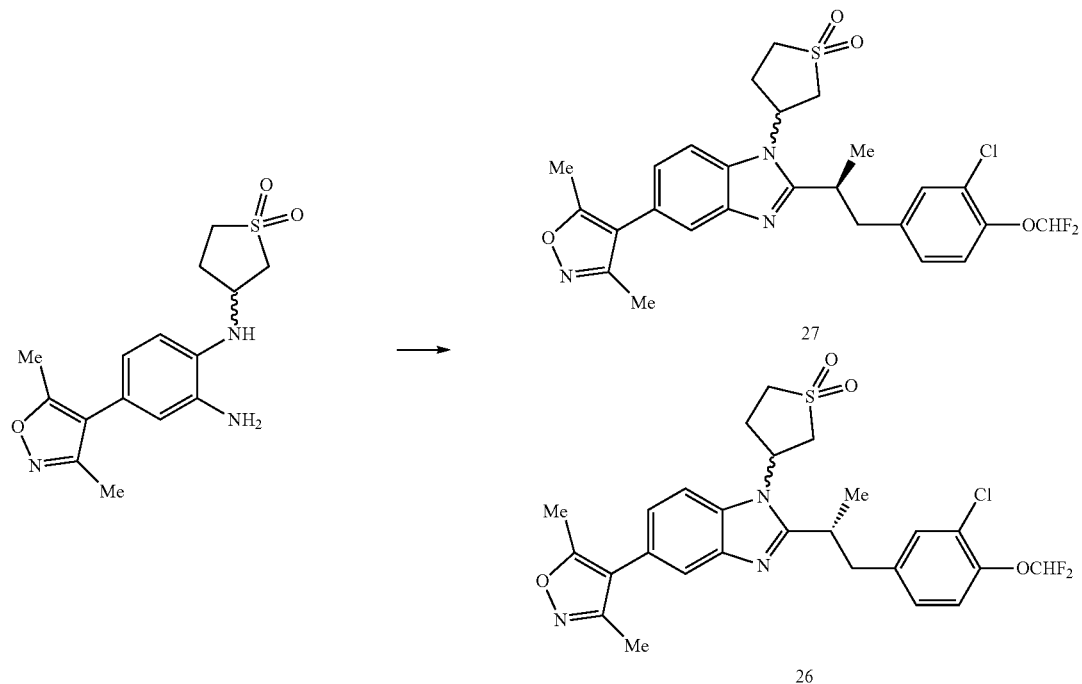 [SMILES: Cc1noc(C)c1-c1ccc(NC2CCS(=O)(=O)C2)c(N)c1 ; Cc1noc(C)c1-c1ccc2c(c1)nc([C@H](C)Cc1ccc(OC(F)F)c(Cl)c1)n2C1CCS(=O)(=O)C1 ; Cc1noc(C)c1-c1ccc2c(c1)nc([C@@H](C)Cc1ccc(OC(F)F)c(Cl)c1)n2C1CCS(=O)(=O)C1]

To a stirred solution of 3-(3-chloro-4-(difluoromethoxy)phenyl)-2-methylpropanoic acid (86 mg, 0.327 mmol) [prepared according to general route C], DIPEA (0.057 ml, 0.327 mmol) and HATU (124 mg, 0.327 mmol) in DMF (2 ml) was added 3-((2-amino-4-(3,5-dimethylisoxazol-4-yl)phenyl)amino) tetrahydro thiophene 1,1-dioxide (100 mg, 0.311 mmol) [prepared according to general route B from 3-aminotetrahydrothiophene 1,1-dioxide hydrochloride in step b] and the resulting solution was left to stir at room temperature. After 6 hr 45 min, 3-(3-chloro-4-(difluoromethoxy)phenyl)-2-methylpropanoic acid (16 mg), DIPEA (10 µl) and HATU (24 mg) were added and the resulting reaction mixture was left to stir at room temperature for 18 hours, diluted with ethyl acetate (5 ml) and washed with saturated NaHCO3 solution (5 ml). The aqueous layer was extracted with ethyl acetate (2×5 ml) and the combined organics were washed with water (5 ml), brine (2×5 ml), dried (MgSO4) and concentrated in vacuo to give the intermediate 3-(3-chloro-4-(difluoromethoxy)phenyl)-N-(5-(3,5-dimethylisoxazol-4-yl)-2-((1,1-dioxidotetrahydrothiophen-3-yl)amino)phenyl)-2-methylpropanamide, which was used without further purification.

A solution of 3-(3-chloro-4-(difluoromethoxy)phenyl)-N-(5-(3,5-dimethylisoxazol-4-yl)-2-((1,1-dioxidotetrahydrothiophen-3-yl)amino)phenyl)-2-methylpropanamide (177 mg, 0.312 mmol) in glacial acetic acid (3 mL, 52.4 mmol) was stirred at 90° C. for 3 days then at 110° C. for 7 days. The reaction mixture was allowed to cool to room temperature. The reaction mixture was then concentrated in vacuo to give a residue which was partitioned between DCM (5 ml) and saturated NaHCO3 solution (5 ml) and passed through a phase separator. The organic phase was then concentrated in vacuo to give a dark yellow gum. The crude product was purified by preparative HPLC (Gilson, Acidic (0.1% Formic acid), Acidic, Waters X-Select Prep-C18, 5 µm, 19×50 mm column, 30-40% MeCN in Water) and concentrated in vacuo then by chromatography on silica gel (12 g column, 0-80% EtOAc/isohexane) to give 27 3-(2-((S)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide 27 (30 mg, 17%) as a pale yellow solid-Rt=2.26 min (method 2); m/z 550 (M+H)+(ES+); 7.74 (1H, d), 7.67 (1H, d), 7.58 (1H, s), 7.43-7.02 (1H, 3H, m), 3.86-3.74 (1H, m), 3.66 (1H, q), 3.60-3.50 (2H, m), 3.36-3.25 (1H, m), 3.21 (1H, dd), 2.98 (1H, dd), 2.75-2.60 (1H, m), 2.42 (3H, s), 2.31 (1H, dt), 2.25 (3H, s), 1.26 (3H, d) then 3-(2-((R)-1-(3-chloro-4-(difluoromethoxy) phenyl)propan-2-yl)-5-(3,5-dimethylisoxazol-4-yl)-1H-benzo[d]imidazol-1-yl)tetrahydro thiophene 1,1-dioxide 26 (22 mg, 12%) as a pale pink solid-Rt=2.25 min (method 2); m/z 550 (M+H)+(ES+); 7.75 (1H, d), 7.67 (1H, d), 7.56 (1H, s), 7.44-7.04 (4H, m), 5.74-5.59 (1H, m), 3.71-3.52 (3H, m), 3.52-3.43 (1H, m), 3.18 (1H, dd), 2.95 (1H, dd), 2.81-2.66 (1H, m), 2.66-2.55 (1H, m), 2.42 (3H, s), 2.25 (3H, s), 1.25 (3H, d).

Example 28: 4-(2-((R)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole (R)-3-(4-chloro-3-fluorophenyl)-N-(5-(3,5-dimethylisoxazol-4-yl)-2-(((R)-1-(methylsulfonyl)pyrrolidin-3-yl)amino)phenyl)-2-methylpropanamide 4-(2-((R)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole the residue and the solvent removed in vacuo to afford 4-(2-((R)-1-(4-chloro-3-fluorophenyl)propan-2-yl)-1-((R)-1-(methyl sulfonyl)pyrrolidin-3-yl)-1H-benzo[d]imidazol-5-yl)-3,5-dimethylisoxazole (133 mg, 26%) as an off white solid; Rt 2.00 min (Method 1), m/z 531 (M+H)+(ES+); Chiral HPLC (Diacel Chiralpak IA, 5 □m, 4.6×250 mm, isocratic gradient of 5% EtOH, 19% DCM and 76% i-Hexane+0.2% TFA) RT=16.87 min, 96% de @ 254 nm; 1H NMR (DMSO-d6) δ 7.69 (1H, d), 7.66-7.62 (1H, m), 7.48 (1H, t), 7.37 (1H, d), 7.22 (1H, d), 7.12 (1H, d), 5.52-5.40 (1H, m), 3.81-3.74 (1H, m), 3.74-3.64 (3H, m), 3.64-3.57 (1H, m), 3.41-3.34 (1H, m), 3.25-3.16 (1H, m), 3.07 (3H, s), 3.03-2.95 (1H, m), 2.46-2.36 (4H, m), 2.28-2.14 (3H, m), 1.28 (3H, d).

Example 29: 4-(2-((S)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole 4-(2-((S)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole

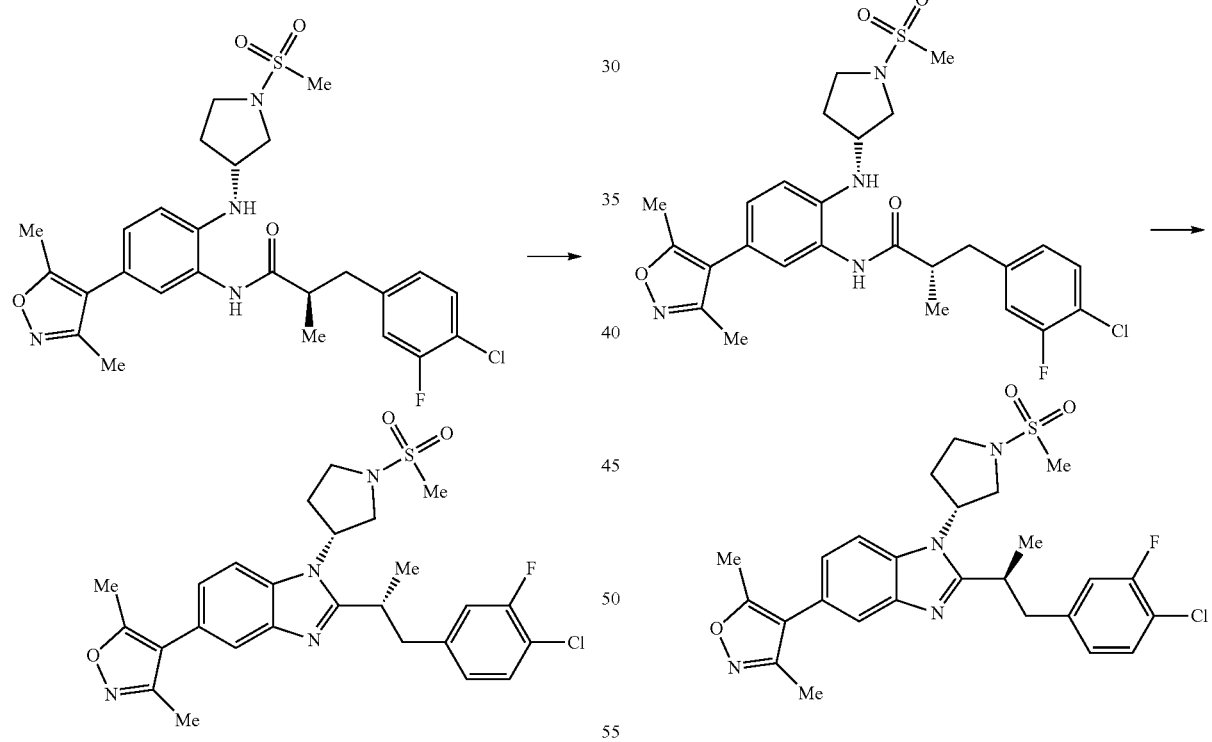

(R)-3-(4-chloro-3-fluorophenyl)-N-(5-(3,5-dimethylisoxazol-4-yl)-2-(((R)-1-(methylsulfonyl)pyrrolidin-3-yl)amino)phenyl)-2-methylpropanamide (508 mg, 0.925 mmol) was dissolved in acetic acid (3 ml) and heated to 80° C. for 6 days. The solvent was removed in vacuo and the crude residue purified by reverse phase chromatography (40 g C18 flash column, 15-75% MeCN (0.1% formic acid) in water (0.1% formic acid), gradient elution). Product fractions were combined and concentrated in vacuo. The residue was taken up in DCM and passed through a phase sep cartridge. The solvent was removed in vacuo, ether added to (S)-3-(4-chloro-3-fluorophenyl)-N-(5-(3,5-dimethylisoxazol-4-yl)-2-(((R)-1-(methylsulfonyl)pyrrolidin-3-yl)amino)phenyl)-2-methylpropanamide (604 mg, 1.100 mmol) was dissolved in acetic acid (3 ml) and heated to 80° C. for 6 days. The solvent was removed in vacuo and the crude residue purified by reverse phase chromatography (40 g C18 flash column, 15-75% MeCN (0.1% formic acid) in water (0.1% formic acid), gradient elution). Product fractions were combined and concentrated in vacuo. The residue was taken up in DCM and passed through a PhaseSep cartridge. The solvent was removed in vacuo, ether added to the residue and the solvent removed in vacuo to afford 4-(2-((S)-1-(4-chloro-3-fluorophenyl)propan-2-yl)-1-((R)-1-(methyl sulfonyl)pyrrolidin-3-yl)-1H-benzo[d]imidazol-5-yl)-3,5-dimethylisoxazole (107 mg, 0.191 mmol, 17.40% yield) as an off white solid; Rt 1.96 min (Method 1), m/z 531 (M+H)+(ES+); Chiral HPLC (Diacel Chiralpak IA, 5 □m, 4.6×250 mm, isocratic gradient of 5% EtOH, 19% DCM and 76% i-Hexane+0.2% TFA) RT=15.11 min, 95% de @ 254 nm; 1H NMR (DMSO-d6) δ 7.78 (1H, d), 7.64-7.60 (1H, m), 7.32 (1H, t), 7.29-7.24 (1H, m), 7.10-7.05 (1H, m), 6.91-6.87 (1H, m), 5.38-5.28 (1H, m), 3.86-3.74 (1H, m), 3.74-3.66 (1H, m), 3.54-3.36 (2H, m), 3.26-3.11 (3H, m), 3.10-2.96 (4H, m), 2.62-2.42 (4H, m), 2.30 (3H, s), 1.51 (3H, d).

Example 30: (R)-4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide (R)-4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide

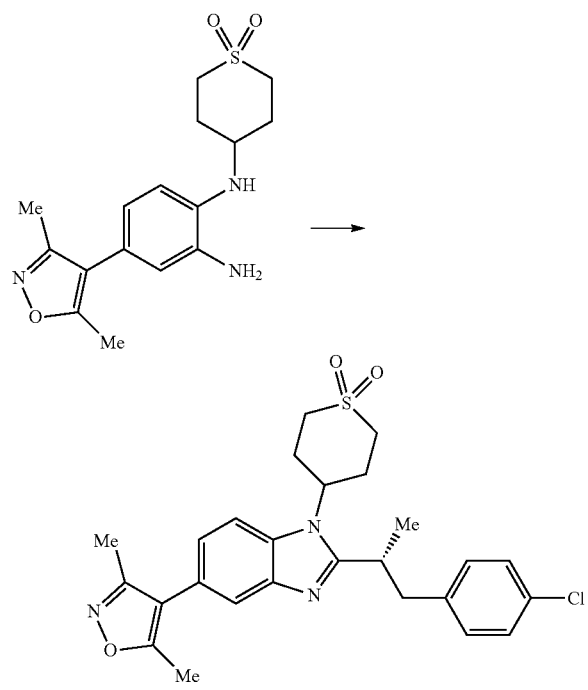

A solution of (R)-3-(4-chlorophenyl)-N-(5-(3,5-dimethylisoxazol-4-yl)-2-((1,1-dioxidotetra hydro-2H-thiopyran-4-yl)amino)phenyl)-2-methylpropanamide (152 mg, 0.295 mmol) in acetic acid (1 ml) was heated to 110° C. and the reaction mixture stirred for 96 h. After cooling to rt the solvent was removed in vacuo. To the residue was added DMSO (2.5 ml). The crude material was purified by preparative HPLC (Varian, acidic column, 20-50% MeCN in water). Product fractions were combined and the solvent removed in vacuo then azeotroped the residue with acetonitrile. The residue was taken up in DCM and passed through a PhaseSep cartridge. The solvent was removed in vacuo and to the residue was added ether (3 ml). After sonication, the resulting precipitate was collected by filtration, washing with ether (5 ml) to afford (R)-4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide (41 mg, 28%) as a white solid; Rt 1.84 min (Method 1), m/z 499 (M+H)+(ES+); Chiral HPLC (Diacel Chiralpak IA, 5 um, 4.6×250 mm, isocratic gradient of 5% EtOH, 19% DCM and 76% i-Hexane+0.2% TFA. RT=19.65 min, >99% ee @ 254 nm; 1H NMR (DMSO-d6) δ 7.64 (s, 1H), 7.56 (d, J=8.4 Hz, 1H), 7.37-7.30 (m, 2H), 7.30-7.19 (m, 3H), 4.91 (m, 1H), 3.68-3.54 (m, 2H), 3.54-3.44 (m, 1H), 3.24-3.11 (m, 3H), 3.00 (dd, J=13.5, 7.5 Hz, 1H), 2.95-2.68 (m, 2H), 2.42 (s, 3H), 2.25 (m, 4H), 1.67 (m, 1H), 1.30 (d, J=6.6 Hz, 3H).

Example 31: (S)-4-(2-(1-(4-chlorophenyl)propan-2-yl)-5-(3,5-dimethylisoxazol-4-yl)-1H-enzo[d]imidazol-1-yl)tetrahydro-2H-thiopyran 1,1-dioxide (S)-4-(2-(1-(4-chlorophenyl)propan-2-yl)-5-(3,5-dimethylisoxazol-4-yl)-1H-enzo[d]imidazol-1-yl)tetrahydro-2H-thiopyran 1,1-dioxide

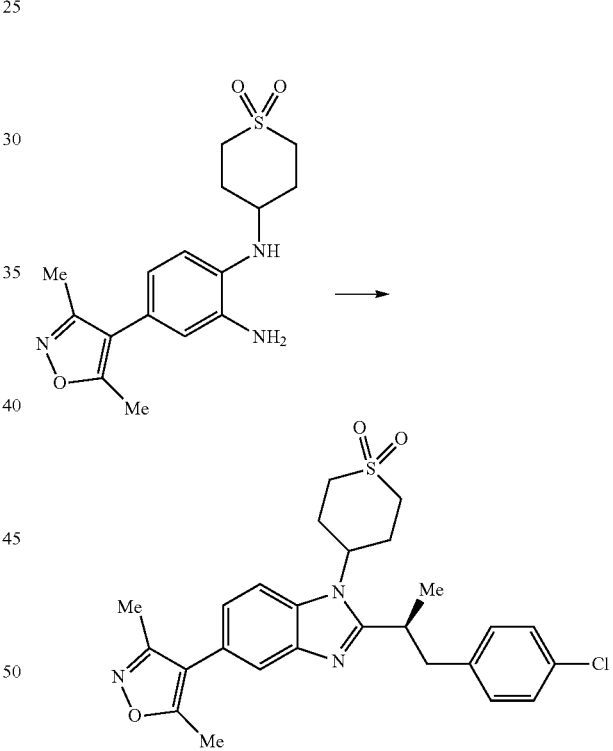

A solution of (S)-3-(4-chlorophenyl)-N-(5-(3,5-dimethylisoxazol-4-yl)-2-((1,1-dioxidotetrahydro-2H-thiopyran-4-yl)amino)phenyl)-2-methylpropanamide (252 mg, 0.488 mmol) in acetic acid (1.5 ml) was heated to 110° C. and the reaction mixture stirred for 72 h. After cooling to rt, the solvent was removed in vacuo. To the residue was added DMSO (2.5 ml). The crude material was purified by prep hplc (Varian, lab 4, acidic column, 20-50% MeCN in water). Product fractions were combined and the solvent removed in vacuo then azeotroped with acetonitrile. The residue was taken up in DCM and passed through a PhaseSep cartridge.

The solvent was removed in vacuo and to the residue was added ether (3 mL). After trituration and sonication the resultant precipitate was collected by filtration, washing with ether (5 ml) to afford (S)-4-(2-(1-(4-chlorophenyl) propan-2-yl)-5-(3,5-dimethylisoxazol-4-yl)-1H-benzo[d] imidazol-1-yl)tetrahydro-2H-thiopyran 1,1-dioxide (105 mg, 43%) as a white solid; Rt 1.84 min (Method 1), m/z 499 (M+H)+(ES+); Chiral HPLC (Diacel Chiralpak IA, 5 um, 4.6×250 mm, isocratic gradient of 5% EtOH, 19% DCM and 76% i-Hexane+0.2% TFA. RT=18.00 min, >98% ee @ 254 nm; 1H NMR (DMSO-d6) δ 7.64 (s, 1H), 7.56 (d, J=8.4 Hz, 1H), 7.37-7.30 (m, 2H), 7.30-7.19 (m, 3H), 4.91 (m, 1H), 3.68-3.54 (m, 2H), 3.54-3.44 (m, 1H), 3.24-3.11 (m, 3H), 3.00 (dd, J=13.5, 7.5 Hz, 1H), 2.95-2.68 (m, 2H), 2.42 (s, 3H), 2.25 (m, 4H), 1.67 (m, 1H), 1.30 (d, J=6.6 Hz, 3H).

Example 32: 4-(2-((R)-1-(4-chloro-3-fluorophenyl) propan-2-yl)-1-((S)-1-(methylsulfonyl)pyrrolidin-3-yl)-1H-benzo[d]imidazol-5-yl)-3,5-dimethylisoxazole Tert-butyl (S)-3-((4-(3,5-dimethylisoxazol-4-yl)-2-nitrophenyl)amino)pyrrolidine-1-carboxylate

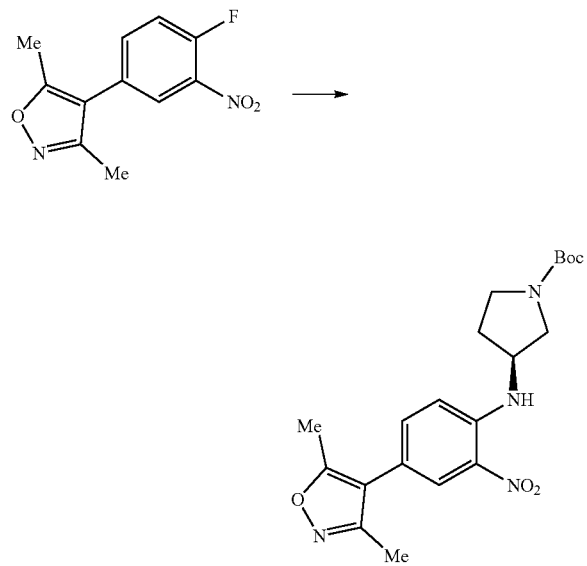

A mixture of 4-(4-fluoro-3-nitrophenyl)-3,5-dimethylisoxazole (6.34 g, 26.8 mmol) and (S)-tert-butyl 3-aminopyrrolidine-1-carboxylate (5 g, 26.8 mmol) was stirred in dry THF (100 ml) and TEA (11.23 ml, 81 mmol) was added. The reaction was stirred at 40° C. for 72 h then heated to 50° C. and stirred for 18 h. After cooling to rt, the reaction mixture was poured into ice water (300 ml). The mixture was extracted with ethyl acetate (2×500 ml). Combined organics were dried (MgSO4) and concentrated in vacuo to afford (S)-tert-butyl 3-((4-(3,5-dimethylisoxazol-4-yl)-2-nitrophenyl)amino)pyrrolidine-1-carboxylate (11.57 g, 99%) as a thick orange oil; Rt 1.xx min (Method 1), m/z 302 (M+H-Boc)+(ES+).

Tert-butyl (S)-3-((2-amino-4-(3,5-dimethylisoxazol-4-yl)phenyl)amino)pyrrolidine-1-carboxylate

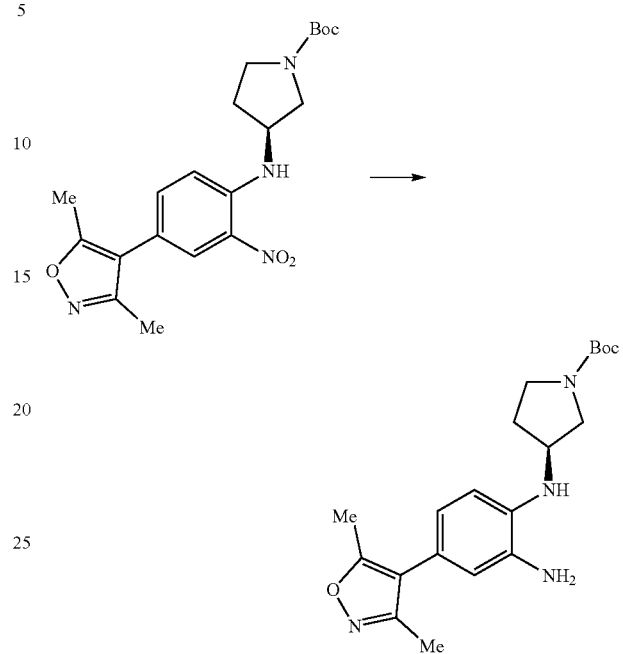

(S)-tert-butyl 3-((4-(3,5-dimethylisoxazol-4-yl)-2-nitrophenyl)amino)pyrrolidine-1-carboxylate (10.8 g, 26.8 mmol) was dissolved in water (500 ml) and THF (500 ml). ammonia (20.90 ml, 537 mmol) and sodium dithionite (46.7 g, 268 mmol) were added and the reaction stirred at RT for 18 h. EtOAc (500 ml) was added, the mixture transferred to a sep funnel and washed sequentially with 1M NaOH (400 ml) and brine (200 ml). The organic phase was dried (MgSO4), filtered and concentrated in vacuo to give an off white solid. The material was triturated with ether and collected by filtration. The filtrate was concentrated in vacuo to afford a light fluffy off white solid. After LCMS and NMR analysis the triturated material and the material obtained from the filtrate were combined to afford (S)-tert-butyl 3-((2-amino-4-(3,5-dimethylisoxazol-4-yl)phenyl)amino)pyrrolidine-1-carboxylate (7.64 g, 20.31 mmol, 76% yield) as an off white fluffy solid; Rt 1.xx min (Method 1), m/z 272 (M+H-Boc)+ (ES+);

Tert-butyl (S)-3-((2-((R)-3-(4-chloro-3-fluorophenyl)-2-methylpropanamido)-4-(3,5-dimethylisoxazol-4-yl)phenyl)amino)pyrrolidine-1-carboxylate

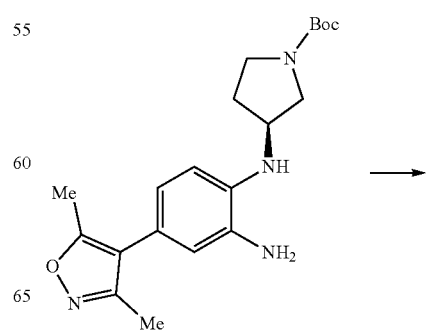

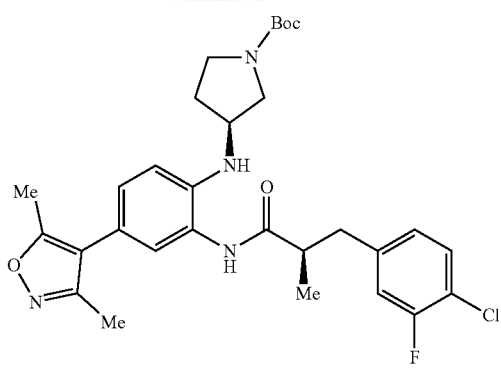

N-ethyl-N-isopropylpropan-2-amine (1.172 ml, 6.67 mmol) was added to a solution of (R)-tert-butyl-3-((2-amino-4-(3,5-dimethylisoxazol-4-yl)phenyl)amino)pyrrolidine-1-carboxylate (1 g, 2.68 mmol), (R)-3-(4-chloro-3-fluorophenyl)-2-methylpropanoic acid (0.64 g, 2.95 mmol) and 2-(3H-[1,2,3]triazolo[4,5-b]pyridin-3-yl)-1,1,3,3-tetramethylisouronium hexafluoro phosphate(V) (1.327 g, 3.49 mmol) in DMF (10 ml) at 0° C. and allowed to stir at room temperature for 16 hours. Additional (R)-3-(4-chloro-3-fluorophenyl)-2-methylpropanoic acid (0.16 g, 0.373 mmol) and 2-(3H-[1,2,3]triazolo[4,5-b]pyridin-3-yl)-1,1,3,3-tetramethyl isouronium hexafluorophosphate(V) (0.331 g, 0.8723 mmol) were added and the reaction stirred for 5 hours. The reaction mixture was diluted with EtOAc (80 mL), washed with sat'd aqueous sodium bicarbonate solution (20 ml) washed with water (20 mL) and brine (10 mL), dried (MgSO4), filtered and evaporated in vacuo. The crude reaction mixture was purified by chromatography on silica gel (40 g column, 0-100% EtOAc in isohexane) to give (R)-tert-butyl 3-((2-((R)-3-(4-chloro-3-fluorophenyl)-2-methylpropanamido)-4-(3,5-dimethylisoxazol-4-yl) phenyl) amino)pyrrolidine-1-carboxylate (1.47 g, 96%) as an oil; Rt 1.92 min (Method 2), m/z 571 (M+H)+(ES+).

(R)-3-(4-chloro-3-fluorophenyl)-N-(5-(3,5-dimethylisoxazol-4-yl)-2-(((S)-pyrrolidin-3-yl)amino)phenyl)-2-methylpropanamide

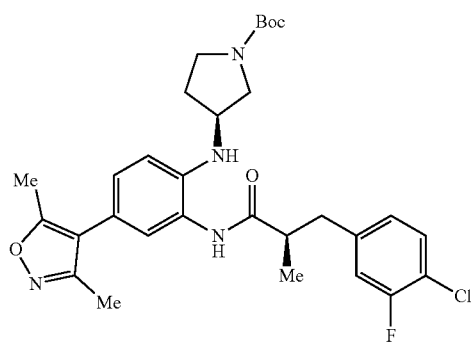

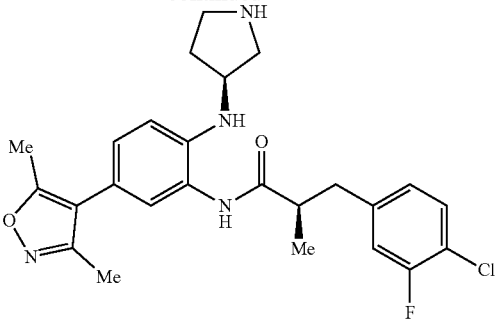

(R)-tert-butyl-3-((2-((R)-3-(4-chloro-3-fluorophenyl)-2-methylpropanamido)-4-(3,5-dimethyl isoxazol-4-yl)phenyl) amino)pyrrolidine-1-carboxylate (1.47 g, 2.57 mmol) was dissolved in DCM (5 ml), cooled to 0° C., and TFA (5 ml, 64.9 mmol) was added dropwise. The reaction was allowed to warm to room temperature and stirred for 6 hours. TFA was removed in vacuo and azeotroped with acetonitrile to afford (R)-3-(4-chloro-3-fluorophenyl)-N-(5-(3,5-dimethylisoxazol-4-yl)-2-(((S)-pyrrolidin-3-yl)amino)phenyl)-2-methylpropanamide as a gum; Rt 1.92 min (Method 2), m/z 471 (M+H)+(ES+).

(R)-3-(4-chloro-3-fluorophenyl)-N-(5-(3,5-dimethylisoxazol-4-yl)-2-(((R)-1-(methylsulfonyl) pyrrolidin-3-yl)amino)phenyl)-2-methylpropanamide

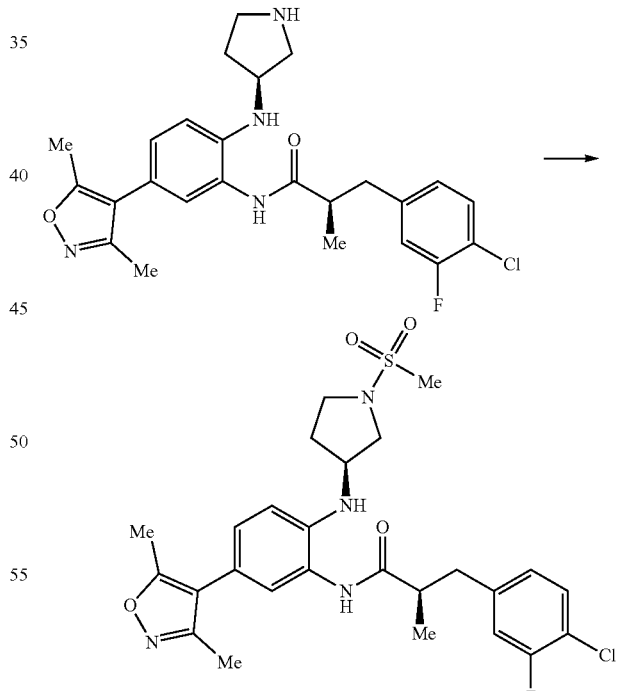

Methanesulphonyl chloride (0.192 ml, 2.48 mmol) was added to a solution of 1 triethylamine (1.153 ml, 8.27 mmol), (R)-3-(4-chloro-3-fluorophenyl)-N-(5-(3,5-dimethylisoxazol-4-yl)-2-((R)-pyrrolidin-3-ylamino)phenyl)-2-methylpropanamide (1.2 g, 2.068 mmol) in DCM (10 ml) at 0° C. The solution was allowed to warm to rt and stirred for 5 hours. DCM (100 ml) and water (100 ml) were added. The DCM was separated, dried (MgSO4), filtered and evaporated in vacuo. The crude product was purified by chromatography on the Companion (120 g column, 0-20% MeOH/DCM) to afford (R)-3-(4-chloro-3-fluorophenyl)-N-(5-(3,5-dimethylisoxazol-4-yl)-2-(((S)-1-(methylsulfonyl)pyrrolidin-3-yl)amino)phenyl)-2-methylpropanamide (227 mg, 15%) as a pale yellow solid; Rt 2.29 min (Method 2), m/z 549 (M+H)+(ES+).

4-(2-((R)-1-(4-chloro-3-fluorophenyl)propan-2-yl)-1-((S)-1-(methylsulfonyl)pyrrolidin-3-yl)-1H-benzo[d]imidazol-5-yl)-3,5-dimethylisoxazole

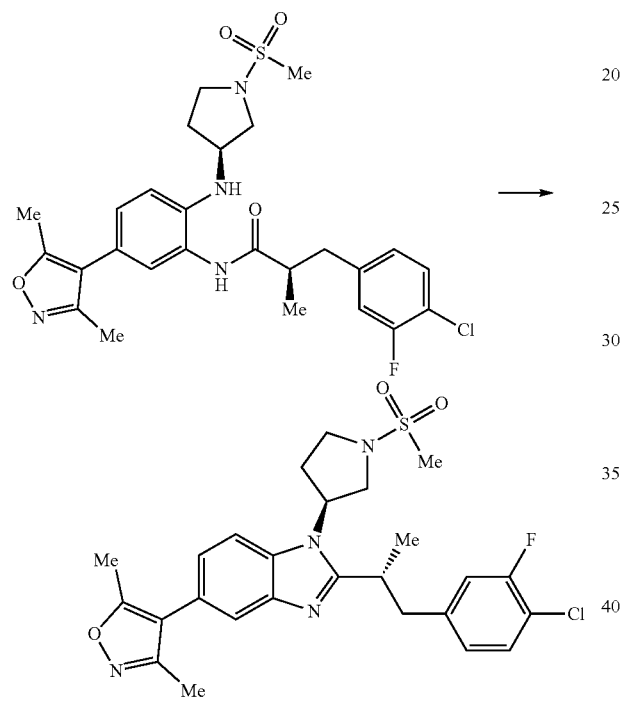

(R)-3-(4-chloro-3-fluorophenyl)-N-(5-(3,5-dimethylisoxazol-4-yl)-2-(((R)-1-(methylsulfonyl) pyrrolidin-3-yl)amino)phenyl)-2-methylpropanamide (222 mg, 0.404 mmol) was added to AcOH (2 ml) and heated to 75° C. for 16 hours. The temperature was increased to 80° C. for 65 hrs. The acetic acid was removed in vacuo and the material azetroped with toluene. The crude product was purified by preparative HPLC (Waters, Acidic (0.1% Formic acid), Acidic, Waters X-Select Prep-C18, 5 μm, 19×50 mm column, 15-35% MeCN in Water) to afford 4-(2-((R)-1-(4-chloro-3-fluorophenyl)propan-2-yl)-1-((S)-1-(methylsulfonyl)pyrrolidin-3-yl)-1H-benzo[d]imidazol-5-yl)-3,5-dimethylisoxazole (15.3 mg, 7%) as a pale white solid; Rt 1.92 min (Method 1), m/z 532 (M+H)+(ES+); 1H NMR (DMSO-d6) δ 7.69 (d, J=8.4 Hz, 1H), 7.64 (d, J=1.6 Hz, 1H), 7.47 (t, J=8.1 Hz, 1H), 7.36 (dd, J=10.6, 1.9 Hz, 1H), 7.22 (dd, J=8.4, 1.7 Hz, 1H), 7.09 (dd, J=8.2, 1.9 Hz, 1H), 5.42 (m, 1H), 3.69 (m, 2H), 3.51 (m, 2H), 3.37 (m, 1H), 3.16 (m, 1H), 3.05 (s, 3H), 3.00 (m, 1H) 2.44 (m, 1H), 2.41 (s, 3H), 2.24 (s, 3H), 1.26 (d, J=6.7 Hz, 3H), one proton not visible.

Example 33: 4-(2-((S)-1-(4-chloro-3-fluorophenyl)propan-2-yl)-1-((S)-1-(methylsulfonyl)pyrrolidin-3-yl)-1H-benzo[d]imidazol-5-yl)-3,5-dimethylisoxazole Tert-butyl (S)-3-((2-((S)-3-(4-chloro-3-fluorophenyl)-2-methylpropanamido)-4-(3,5-dimethylisoxazol-4-yl)phenyl)amino)pyrrolidine-1-carboxylate

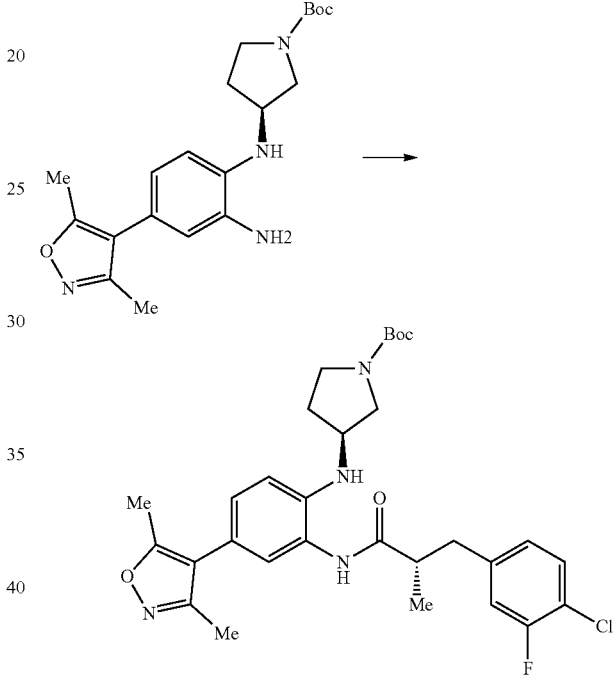

N-ethyl-N-isopropylpropan-2-amine (1.172 ml, 6.61 mmol) was added to a solution of (R)-tert-butyl 3-((2-amino-4-(3,5-dimethylisoxazol-4-yl)phenyl)amino)pyrrolidine-1-carboxylate (1 g, 2.68 mmol), (S)-3-(4-chloro-3-fluorophenyl)-2-methylpropanoic acid (0.64 g, 2.95 mmol) and 2-(3H-[1,2,3]triazolo[4,5-b]pyridin-3-yl)-1,1,3,3-tetramethylisouronium hexafluorophosphate(V) (1.327 g, 3.49 mmol) in DMF (10 ml) at 0° C. and allowed to stir at room temperature for 16 hours. The reaction mixture was diluted with EtOAc (80 mL), washed with sat'd aqueous sodium bicarbonate solution (20 ml) washed with water (20 mL) and brine (10 mL), dried (MgSO4), filtered and evaporated in vacuo. The crude reaction mixture was purified by chromatography on silica gel (80 g column, 0-100% EtOAc in isohexane) to give (R)-tert-butyl 3-((2-((S)-3-(4-chloro-3-fluorophenyl)-2-methylpropan amido)-4-(3,5-dimethylisoxazol-4-yl)phenyl)amino)pyrrolidine-1-carboxylate (0.946 g, 96%); Rt 2.69 min (Method 2), m/z 571 (M+H)+(ES+).

107

(S)-3-(4-chloro-3-fluorophenyl)-N-(5-(3,5-dimethyl-isoxazol-4-yl)-2-(((S)-pyrrolidin-3-yl)amino)phenyl)-2-methylpropanamide

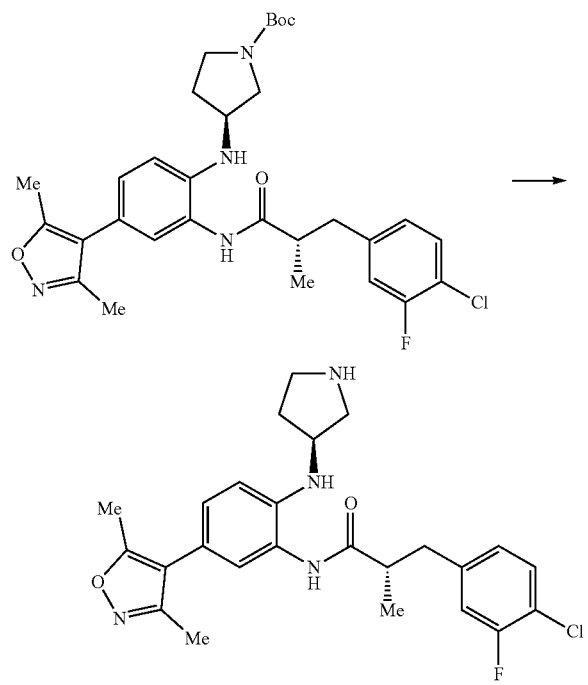

(S)-tert-butyl 3-((2-((S)-3-(4-chloro-3-fluorophenyl)-2-methylpropanamido)-4-(3,5-dimethyl isoxazol-4-yl)phenyl)amino)pyrrolidine-1-carboxylate (0.9464 g, 1.657 mmol) was dissolved in DCM (5 ml), cooled to 0° C., and TFA (5 ml, 64.9 mmol) was added dropwise. The reaction was allowed to warm to room temperature and stirred for 2 hours. TFA remove in vacuo and azetroped with toluen to leave a gum 1480-75-1. The reaction mixture showed product LCMS (Agilent, Basic, Waters X-Bridge C18, 2.5 um, 4.6×30 mm, Basic (0.1% Ammonium Bicarbonate) 4 min method, 5-95% MeCN/water): 1480-75-1, m/z 471.1, 473.2 (M+H)+(ES+); at 1.62 min, 90% purity @254 nm.

(S)-3-(4-chloro-3-fluorophenyl)-N-(5-(3,5-dimethyl-isoxazol-4-yl)-2-(((S)-1-(methylsulfonyl)pyrrolidin-3-yl)amino)phenyl)-2-methylpropanamide

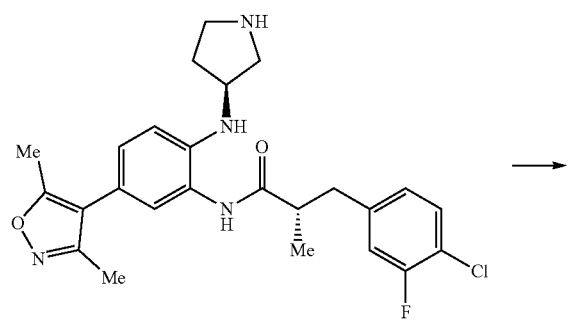

108

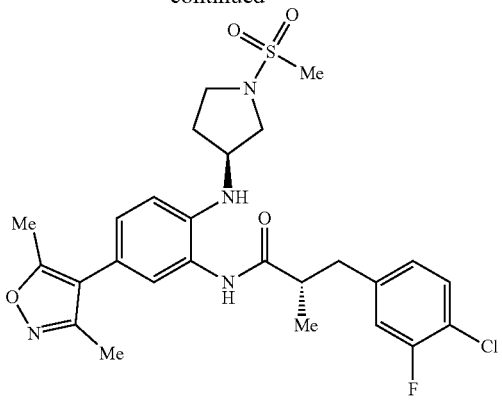

Methanesulphonyl chloride (0.098 ml, 1.264 mmol) was added to a solution of triethylamine (0.587 ml, 4.21 mmol), (R)-3-(4-chloro-3-fluorophenyl)-N-(5-(3,5-dimethylisoxazol-4-yl)-2-((R)-pyrrolidin-3-ylamino)phenyl)-2-methylpropanamide (0.616 g, 1.053 mmol) in DCM (5 ml) at 0° C. The solution was allowed to warm to RT and stirred for 5 hours. DCM (50 ml) and water (20 ml) were added. The DCM was separated, dried (MgSO4), filtered and evaporated in vacuo. The crude product was purified by chromatography on the Companion (80 g column, 50-100% EtOAc/isohexane) to afford (S)-3-(4-chloro-3-fluorophenyl)-N-(5-(3,5-dimethylisoxazol-4-yl)-2-(((S)-1-(methylsulfonyl)pyrrolidin-3-yl)amino)phenyl)-2-methylpropanamide (448 mg, 0.734 mmol, 56.1% yield) as a pale yellow solid. The product was analysed by LCMS (Waters, X-Select, Waters X-Select C18, 2.5 μm, 4.6×30 mm, Acidic (0.1% Formic acid) 4 min method, 5-95% MeCN/water):1480-77-1, m/z (M+H)+(ES+); at 2.32 min, 99% purity @ 254 nm. 1H NMR in DMSO-d6 1480-77-1 was consistent with product structure at 90%

4-(2-((S)-1-(4-chloro-3-fluorophenyl) propan-2-yl)-1-((S)-1-(methylsulfonyl)pyrrolidin-3-yl)-1H-benzo[d]imidazol-5-yl)-3,5-dimethylisoxazole

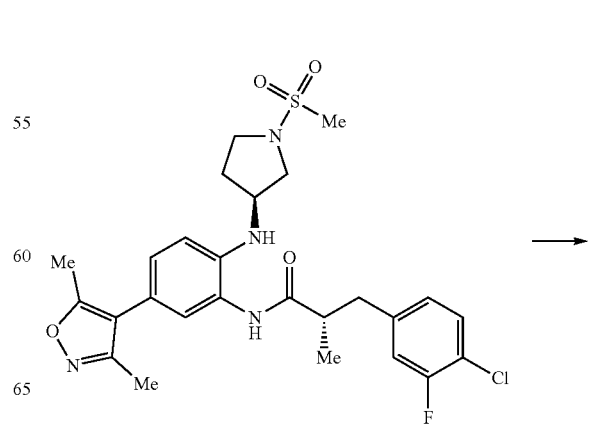

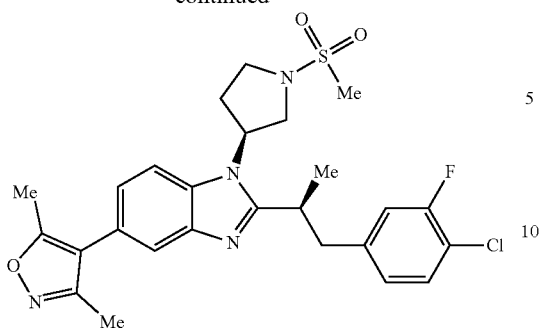

(S)-3-(4-chloro-3-fluorophenyl)-N-(5-(3,5-dimethylisoxazol-4-yl)-2-(((R)-1-(methylsulfonyl) pyrrolidin-3-yl) amino)phenyl)-2-methylpropanamide (448 mg, 0.816 mmol) was added to acetic acid (2 ml) and heated at 80° C. for 80 hours. The solvent was removed in vacuo and the residue azetroped three times with toluene. The crude product was purified by preparative HPLC (Varian, Acidic (0.1% Formic acid), Waters X-Select Prep-C18, 5 μm, 19×50 mm column, 20-50% MeCN in Water) to afford 4-(2-((S)-1-(4-chloro-3-fluorophenyl) propan-2-yl)-1-((S)-1-(methylsulfonyl)pyrrolidin-3-yl)-1H-benzo[d]imidazol-5-yl)-3,5-dimethylisoxazole (20 mg, 4% yield) as a light white solid; Rt 1.98 min (Method 1), m/z 532 (M+H)+(ES+); 1H NMR (DMSO-d6) δ 7.68 (d, J=8.4 Hz, 1H), 7.64 (d, J=1.6 Hz, 1H), 7.47 (t, J=8.1 Hz, 1H), 7.37 (dd, J=10.7, 1.9 Hz, 1H), 7.21 (dd, J=8.4, 1.7 Hz, 1H), 7.11 (dd, J=8.2, 1.9 Hz, 1H), 5.45 (m, 3.81-3.55 (m, 4H), 3.45-3.33 (m, 1H), 3.20 (dd, J=13.7, 6.8 Hz, 1H), 3.07 (s, 3H), 2.98 (dd, J=13.7, 7.9 Hz, 1H), 2.45-2.35 (m, 1H), 2.41 (s, 3H), 2.24-2.15 (m, 1H), 2.24 (s, 3H), 1.27 (d, J=6.7 Hz, 3H).

Example 34: (R)-4-(2-(1-(4-chloro-3-fluorophenyl) propan-2-yl)-5-(3,5-dimethylisoxazol-4-yl)-1H-benzo[d]imidazol-1-yl)tetrahydro-2H-thiopyran 1,1-dioxide (R)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide

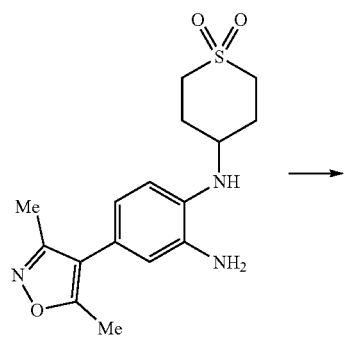

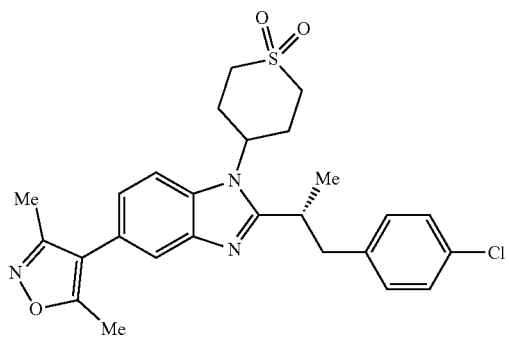

N-ethyl-N-isopropylpropan-2-amine (0.128 ml, 0.716 mmol) was added dropwise to a stirring solution of (R)-3-(4-chloro-3-fluorophenyl)-2-methylpropanoic acid (0.078 g, 0.358 mmol), 2-(3H-[1,2,3]triazolo[4,5-b]pyridin-3-yl)-1,1,3,3-tetramethylisouronium hexafluorophosphate(V) (0.163 g, 0.429 mmol) in DMF (2 ml, 25.8 mmol) for 10 minutes before adding 4-((2-amino-4-(3,5-dimethylisoxazol-4-yl) phenyl)amino)tetrahydro-2H-thiopyran 1,1-dioxide (0.12 g, 0.358 mmol). The resulting brown solution was stirred at room temperature for 20 hours. The mixture was diluted with water and extracted with ethyl acetate (150 mL) (×2). The organic layer was dried (MgSO4), filtered and evaporated under reduced pressure to give intermediate as a brown oil. The crude intermediate was purified by chromatography on silica gel (40 g column, 0-100% EtOAc/isohexane) to afford intermediate. The intermediate was dissolved in acetic acid (2 mL) and heated to 100 C for 48 hours. The mixture was evaporated under reduced pressure to an oil. The crude product was purified by preparative HPLC (Varian, Acidic (0.1% Formic acid), Acidic, Waters X-Select Prep-C18, 5 μm, 19×50 mm column, 20-50% MeCN in Water) to afford the desired product at 57% ee (chiral analysis: 5% EtOH in 19% DCM and 76% ISOHEXANE (0.2% TFA) ISOCRATIC GRADIENT). The crude product was purified by Chiral HPLC (Lab 1 Bay 2, Diacel Chiralpak IA, 5 um, 4.6×250 mm, 30 min method, 10% EtOH & 4:1 isohexane/DCM+0.2% TFA, Isocratic) to afford (R)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide (44 mg) as a white solid; Rt 2.03 min (Method 1), m/z 517 (M+H)+(ES+); Chiral HPLC (Lab 1 Bay 2, Diacel Chiralpak IA, 5 um, 4.6×250 mm, isocratic gradient of 5% EtOH, 19% DCM and 76% i-Hexane+0.2% TFA, RT=19.93 min, 100% ee @ 254 nm; 1H NMR (DMSO-d6) δ 7.71-7.62 (2H, m), 7.51 (1H, t), 7.44-7.31 (2H, m), 7.14 (1H, dd), 5.01 (1H, t), 3.72 (1H, m), 3.68-3.49 (2H, m), 3.29-3.17 (3H, m), 3.05 (1H, dd), 2.87 (2H, m), 2.42 (3H, s), 2.25 (4H, m), 1.31 (3H, d).

Example 35: (S)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide (S)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide

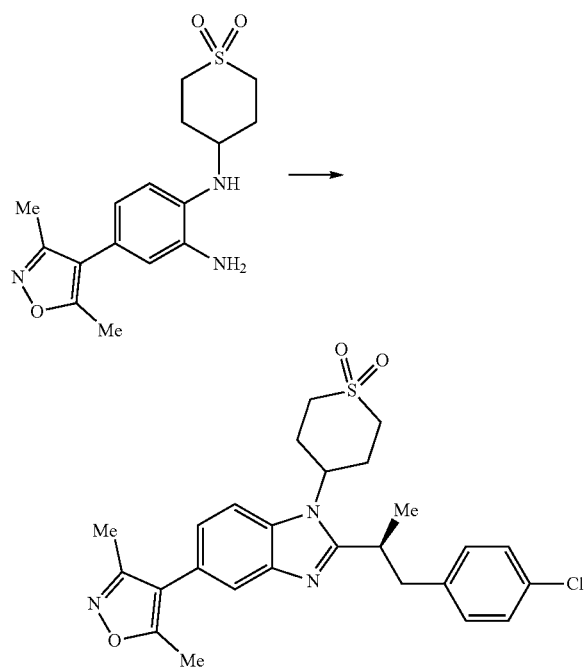

N-ethyl-N-isopropylpropan-2-amine (0.128 ml, 0.716 mmol) was added dropwise to a stirring solution of (S)-3-(4-chloro-3-fluorophenyl)-2-methylpropanoic acid (0.078 g, 0.358 mmol), 2-(3H-[1,2,3]triazolo[4,5-b]pyridin-3-yl)-1,1,3,3-tetramethylisouronium hexafluorophosphate(V) (0.163 g, 0.429 mmol) in DMF (2 ml, 25.8 mmol) for 10 minutes before adding 4-((2-amino-4-(3,5-dimethylisoxazol-4-yl)phenyl)amino)tetrahydro-2H-thiopyran 1,1-dioxide (0.12 g, 0.358 mmol). The resulting brown solution was stirred at room temperature for 20 hours. The mixture was diluted with water and extracted with ethyl acetate (150 mL) (×2). The organic layer was dried (MgSO4), filtered and evaporated under reduced pressure to give intermediate as a brown oil. The crude intermediate was purified by chromatography on silica gel (40 g column, 0-100% EtOAc/isohexane) to afford intermediate. The intermediate was dissolved in acetic acid (2 mL) and heated to 100 C for 48 hours. The mixture was evaporated under reduced pressure to an oil. The crude product was purified by preparative HPLC (Varian, Acidic (0.1% Formic acid), Acidic, Waters X-Select Prep-C18, 5 µm, 19×50 mm column, 20-50% MeCN in Water) to afford a white solid at 45% ee (chiral analysis: Chiralpac IA: 5% EtOH in 19% DCM and 76% ISOHEXANE (0.2% TFA)-ISOCRATIC GRADIENT). The crude product was purified by Chiral HPLC (Lab 1 Bay 2, Diacel Chiralpak IA, 5 um, 4.6×250 mm, 30 min method, 10% EtOH & 4:1 isohexane/DCM+0.2% TFA Isocratic) to afford (S)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide (53 mg) as a white solid; Rt 2.03 min (Method 1), m/z 517 (M+H)+(ES+); Chiral HPLC (Lab 1 Bay 2, Diacel Chiralpak IA, 5 um, 4.6×250 mm, isocratic gradient of 5% EtOH, 19% DCM and 76% i-Hexane+0.2% TFA: RT=12.59 min, 100% de @ 254 nm; 1H NMR (DMSO-d6) δ 7.75 (1H, d), 7.67 (1H, d), 7.50 (1H, t), 7.42 (1H, dd), 7.27 (1H, dd), 7.14 (1H, dd), 5.77-5.53 (1H, m), 3.69-3.59 (2H, m), 3.53 (1H, td), 3.34 (2H, dq), 3.19 (1H, dd), 2.95 (1H, dd), 2.80-2.68 (1H, m), 2.68-2.57 (1H, m), 2.42 (3H, s), 2.25 (3H, s), 1.25 (3H, d)

Example 36: ((R)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide (R)-3-((4-(3,5-dimethylisoxazol-4-yl)-2-nitrophenyl)amino)tetrahydrothiophene 1,1-dioxide

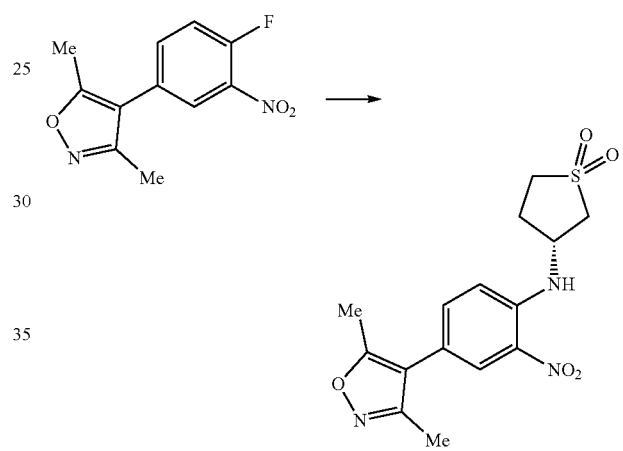

To a mixture of 4-(4-fluoro-3-nitrophenyl)-3,5-dimethylisoxazole (1.4 g, 5.93 mmol) and (R)-3-aminotetrahydrothiophene 1,1-dioxide, HCl (1.017 g, 5.93 mmol) in DMF (10 mL) was added TEA (1.817 ml, 13.04 mmol). The mixture was stirred at 70° C. overnight. The mixture was quenched in ice water (100 mL), washed with water to give (R)-3-((4-(3,5-dimethylisoxazol-4-yl)-2-nitrophenyl)amino)tetrahydrothiophene 1,1-dioxide (1.95 g, 91%) as a bright orange solid; Rt 1.88 min (Method 1), m/z 352 (M+H)+(ES+).

(R)-3-((2-amino-4-(3,5-dimethylisoxazol-4-yl)phenyl)amino)tetrahydrothiophene 1,1-dioxide

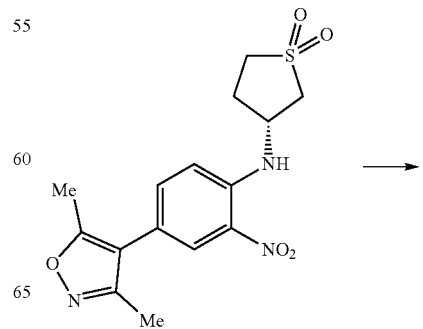

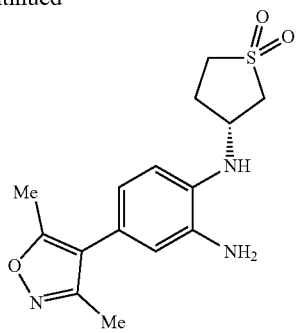

(R)-3-((4-(3,5-dimethylisoxazol-4-yl)-2-nitrophenyl)amino)tetrahydrothiophene 1,1-dioxide (1.95 g, 5.55 mmol) was added to a solution of Sodium dithionite (9.66 g, 55.5 mmol) and ammonium hydroxide (15.44 ml, 111 mmol) in THF (10 ml, 122 mmol) and WATER (10 ml, 555 mmol) and the reaction mixture stirred at RT for 2 hours. The reaction mixture was concentrated in vacuo to leave aqueous layer and the solid present was filtered under vacuum, washed with water (500 mL) and triturated with DCM/ether (1:1) and dried under vacuo to give (R)-3-((2-amino-4-(3,5-dimethylisoxazol-4-yl)phenyl)amino)tetrahydrothio phene 1,1-dioxide (1.22 g, 3.42 mmol, 61.6% yield) as a foamy pink solid; Rt 1.27 min (Method 1), m/z 322 (M+H)+(ES+).

((R)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide

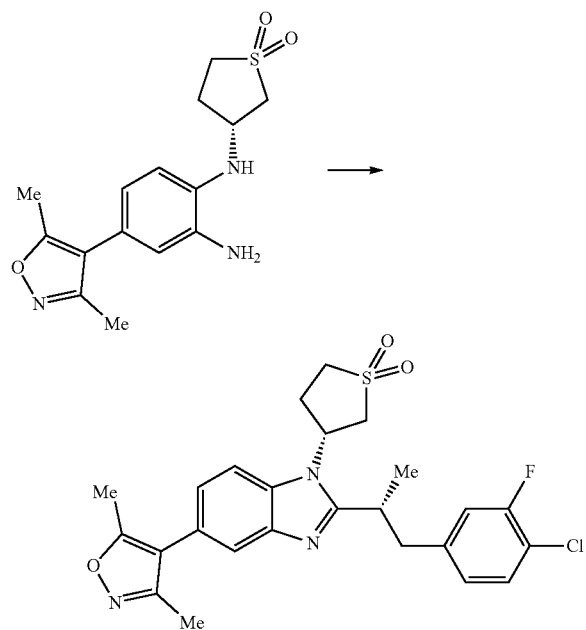

N-ethyl-N-isopropylpropan-2-amine (0.222 ml, 1.245 mmol) was added dropwise to a stirring solution of (R)-3-(4-chloro-3-fluorophenyl)-2-methylpropanoic acid (0.162 g, 0.747 mmol), 2-(3H-[1,2,3]triazolo[4,5-b]pyridin-3-yl)-1,1,3,3-tetramethylisouronium hexafluorophosphate(V) (0.284 g, 0.747 mmol) in DMF (2 ml, 25.8 mmol) for 10 minutes before adding (R)-3-((2-amino-4-(3,5-dimethylisoxazol-4-yl)phenyl)amino)tetrahydrothiophene 1,1-dioxide (0.2 g, 0.622 mmol). The resulting brown solution was stirred at room temperature for 20 hours. The mixture was diluted with water and extracted with ethyl acetate (150 mL) (×2). The organic layer was dried (MgSO4), filtered and evaporated under reduced pressure to give intermediate as a brown oil. The crude intermediate was purified by chromatography on silica gel (40 g column, 0-100% EtOAc/isohexane) to afford intermediate. The intermediate was dissolved in acetic acid (2 mL) and heated to 80 C for 72 hours. LC-MS shows only 30% product so heated at 80 C for a further 72 hours. The mixture was evaporated under reduced pressure to an oil. The crude product was purified by chromatography on silica gel (40 g column, 0-100% EtOAc/isohexane) then by preparative HPLC (Gilson, Acidic (0.1% Formic acid), Acidic, Waters X-Select Prep-C18, 5 µm, 19×50 mm column, 50% isocratic MeCN in Water) to afford (R)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide (66 mg, 21%) as a white solid; Rt 2.16 min (Method 1), m/z 502 (M+H)+(ES+); Chiral HPLC (Lab 1 Bay 2, Diacel Chiralpak IA, 5 um, 4.6×250 mm, isocratic gradient of 5% EtOH, 19% DCM and 76% i-Hexane+0.2% TFA: 1404-14-1, RT=12.59 min, 100% de @ 254 nm; 1H NMR (DMSO-d6) δ 7.75 (1H, d), 7.67 (1H, d), 7.50 (1H, t), 7.42 (1H, dd), 7.27 (1H, dd), 7.14 (1H, dd), 5.77-5.53 (1H, m), 3.69-3.59 (2H, m), 3.53 (1H, td), 3.34 (2H, dq), 3.19 (1H, dd), 2.95 (1H, dd), 2.80-2.68 (1H, m), 2.68-2.57 (1H, m), 2.42 (3H, s), 2.25 (3H, s), 1.25 (3H, d).

Example 37 ((R)-3-(2-((S)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide ((R)-3-(2-((S)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide

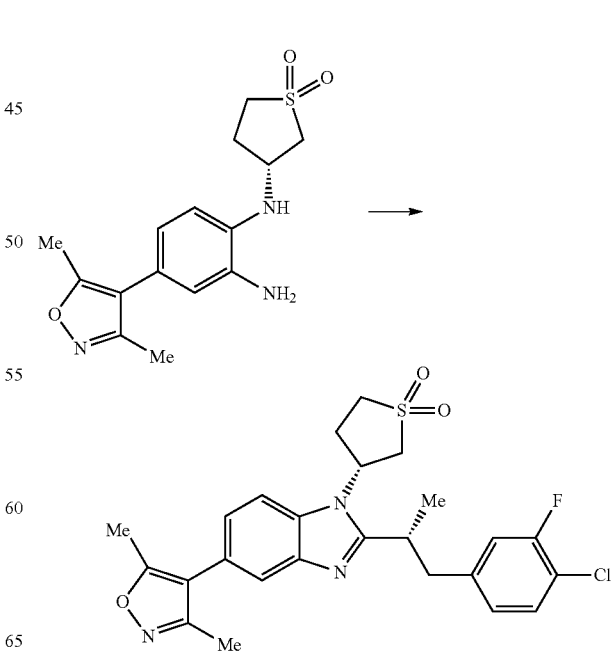

N-ethyl-N-isopropylpropan-2-amine (0.222 ml, 1.245 mmol) was added dropwise to a stirring solution of (S)-3-(4-chloro-3-fluorophenyl)-2-methylpropanoic acid (0.162 g, 0.747 mmol), 2-(3H-[1,2,3]triazolo[4,5-b]pyridin-3-yl)-1,1,3,3-tetramethylisouronium hexafluorophosphate(V) (0.284 g, 0.747 mmol) in DMF (2 ml, 25.8 mmol) for 10 minutes before adding (R)-3-((2-amino-4-(3,5-dimethylisoxazol-4-yl)phenyl)amino)tetrahydrothiophene 1,1-dioxide (0.2 g, 0.622 mmol). The resulting brown solution was stirred at room temperature for 20 hours. The mixture was diluted with water and extracted with ethyl acetate (2×150 mL). The organic layer was dried (MgSO4), filtered and evaporated under reduced pressure to give intermediate as a brown oil. The crude intermediate was purified by chromatography on silica gel (40 g column, 0-100% EtOAc/isohexane) to afford intermediate. The intermediate was dissolved in acetic acid (2 mL) and heated to 80° C. for 72 hours. LC-MS shows only 30% product so heated at 80° C. for a further 72 hours. The mixture was evaporated under reduced pressure to an oil, which was purified by chromatography on silica gel (40 g column, 0-100% EtOAc/isohexane) then by preparative HPLC (Varian, Acidic (0.1% Formic acid), Acidic, Waters X-Select Prep-C18, 5 μm, 19×50 mm column, 50% isocratic MeCN in Water) to afford (R)-3-(2-((S)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide (57 mg, 18%) as a white solid; Rt 2.18 min (Method 1), m/z 502 (M+H)+(ES+); Chiral HPLC (Diacel Chiralpak IA, 5 um, 4.6×250 mm, isocratic gradient of 5% EtOH, 19% DCM and 76% i-Hexane+0.2% TFA: RT=11.59 min, 100% de @ 254 nm; 1H NMR (DMSO-d6) δ 7.74 (1H, d), 7.67 (1H, d), 7.51 (1H, d), 7.42 (1H, dd), 7.26 (1H, dd), 7.17 (1H, dd), 5.68 (1H, dq), 3.81 (1H, dd), 3.69-3.60 (1H, m), 3.60-3.49 (2H, m), 3.34 (1H, tt), 3.23 (1H, dd), 2.98 (1H, dd), 2.79-2.59 (1H, m), 2.41 (4H, s), 2.24 (3H, s), 1.24 (3H, d).

Example 38: (R)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide (R)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide

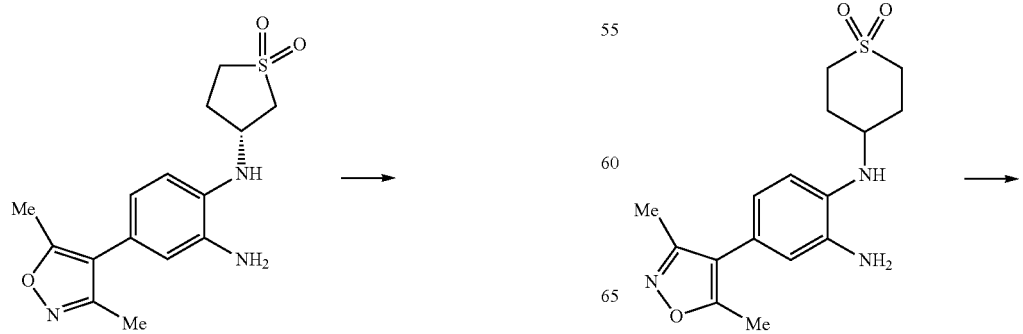

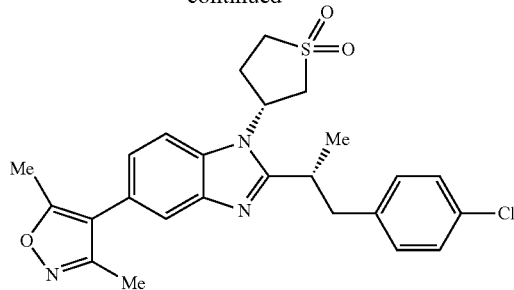

N-ethyl-N-isopropylpropan-2-amine (0.250 ml, 1.400 mmol) was added dropwise to a stirring solution of (R)-3-(4-chlorophenyl)-2-methylpropanoic acid (0.139 g, 0.700 mmol), 2-(3H-[1,2,3]triazolo[4,5-b]pyridin-3-yl)-1,1,3,3-tetramethylisouronium hexafluorophosphate(V) (0.248 g, 0.653 mmol) in DMF (3 ml, 38.7 mmol) for 10 minutes before adding (R)-3-((2-amino-4-(3,5-dimethylisoxazol-4-yl)phenyl)amino)tetrahydrothiophene 1,1-dioxide (0.15 g, 0.467 mmol). The resulting brown solution was stirred at room temperature for 20 hours. The mixture was diluted with water and extracted with ethyl acetate (2×150 mL). The organic layer was dried (MgSO4), filtered and evaporated under reduced pressure to give intermediate as a brown oil. The crude intermediate was purified by chromatography on silica gel (40 g column, 0-100% EtOAc/isohexane) to afford intermediate. The intermediate was dissolved in acetic acid (2 mL) and heated to 80° C. for 112 hours. The mixture was evaporated to dryness and the crude product was purified by preparative HPLC (Varian, Acidic (0.1% Formic acid), Acidic, Waters X-Select Prep-C18, 5 μm, 19×50 mm column, 20-50% MeCN in Water) to afford (R)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide (27 mg, 0.055 mmol, 11.71% yield) as a off-white solid; Rt 2.02 min (Method 1), m/z 484 (M+H)+(ES+); Chiral HPLC (Lab 1 Bay 2, Diacel Chiralpak IA, 5 um, 4.6×250 mm, isocratic gradient of 5% EtOH, 19% DCM and 76% i-Hexane+0.2% TFA: RT=xxmin, 100% de @ 254 nm; 1H NMR (DMSO-d6) δ 7.73 (1H, dd), 7.67 (1H, d), 7.37-7.32 (2H, m), 7.32-7.19 (3H, m), 5.62 (1H, t), 3.64-3.52 (2H, m), 3.52-3.43 (2H, m), 3.30 (2H, m), 3.15 (1H, dd), 2.93 (1H, dd), 2.82-2.67 (1H, m), 2.67-2.52 (1H, m), 2.42 (3H, s), 2.25 (3H, s), 1.27 (3H, dd).

Example 39: (R)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide (R)—N-(5-(3,5-dimethylisoxazol-4-yl)-2-((1,1-dioxidotetrahydro-2H-thiopyran-4-yl)amino)phenyl)-3-(3-fluoro-4-(trifluoromethoxy)phenyl)-2-methylpropanamide

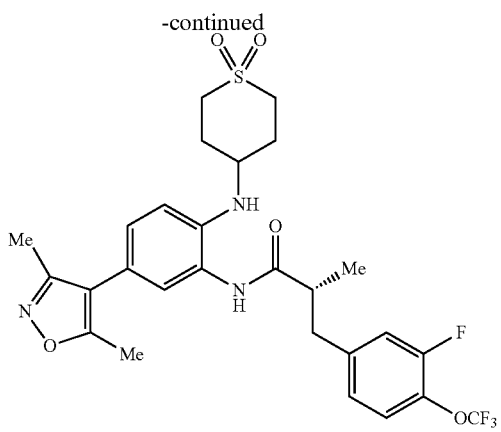
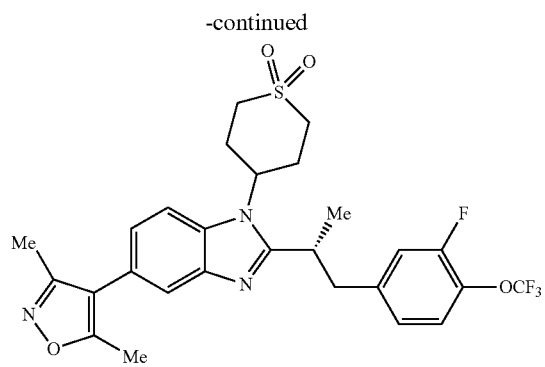

N-ethyl-N-isopropylpropan-2-amine (54.5 µl, 0.313 mmol) was added to a mixture of 4-((2-amino-4-(3,5-dimethylisoxazol-4-yl)phenyl)amino)tetrahydro-2H-thiopyran 1,1-dioxide (100 mg, 0.298 mmol), HATU (119 mg, 0.313 mmol) and (R)-3-(3-fluoro-4-(trifluoromethoxy)phenyl)-2-methylpropanoic acid (124 mg, 0.313 mmol) in DMF (1 ml). The reaction mixture was stirred at rt for 18 h. The reaction mixture was partitioned between DCM (20 ml) and water (10 ml). The organic phase was washed with a further portions of water (10 ml) and collected via a phase sep cartridge. The solvent was removed in vacuo and the loose residue purified by chromatography (4 g silica, 0-100% ethyl acetate in isohexanes, gradient elution) to afford (R)—N-(5-(3,5-dimethylisoxazol-4-yl)-2-((1,1-dioxidotetrahydro-2H-thiopyran-4-yl)amino)phenyl)-3-(3-fluoro-4-(trifluoromethoxy)phenyl)-2-methylpropanamide (162 mg, 0.272 mmol, 91% yield) as an orange smear; Rt 2.38 min (Method 1), m/z 584 (M+H)+(ES+).

(R)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide A solution of (R)—N-(5-(3,5-dimethylisoxazol-4-yl)-2-((1,1-dioxidotetrahydro-2H-thiopyran-4-yl)amino)phenyl)-3-(3-fluoro-4-(trifluoromethoxy)phenyl)-2-methylpropanamide (157 mg, 0.269 mmol) in acetic acid (1 ml) was heated at 80° C. for 6 days. The solvent was removed in vacuo and the residue was dissolved in the minimum of DCM. The solution was purified by chromatography (12 g silica, 10-100% ethyl acetate in isohexanes, gradient elution). Product fractions were combined and concentrated in vacuo. The residue was transferred to a scintillation vial with methanol and the solvent removed in vacuo to afford (R)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide (60 mg, 39%) as a pale yellow solid; Rt 2.10 min (Method 1), m/z 566 (M+H)+ (ES+); 1H NMR (DMSO-d6) δ 7.64 (d, J=1.6 Hz, 1H), 7.56 (d, J=8.5 Hz, 1H), 7.51-7.43 (m, 2H), 7.25 (d, J=1.7 Hz, 1H), 7.20 (d, J=8.6 Hz, 1H), 4.93 (m, 1H), 3.67-3.46 (m, 3H), 3.26-3.13 (m, 2H), 3.05 (dd, J=13.6, 8.1 Hz, 1H), 2.90-2.78 (m, 3H), 2.41 (s, 3H), 2.24 (s, 3H), 2.18 (m, 1H), 1.81 (m, 1H), 1.27 (d, J=6.7 Hz, 3H).

Example 40: (S)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide (S)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide

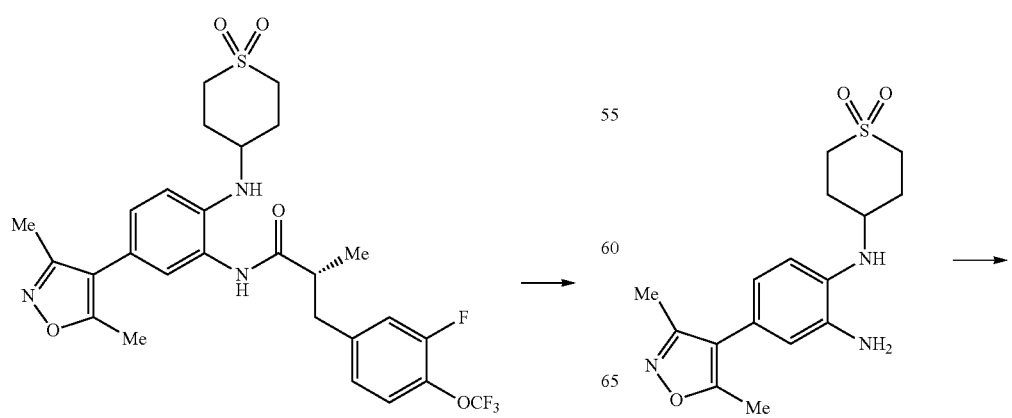

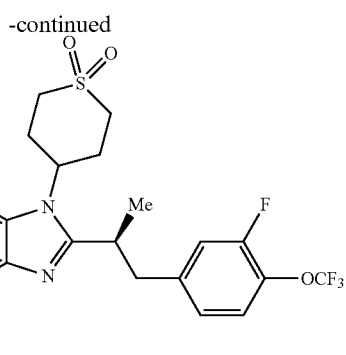

Example 41: (S)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide (S)-4-(2-(methylthio)ethyl)-2-phenyl-4,5-dihydrooxazole

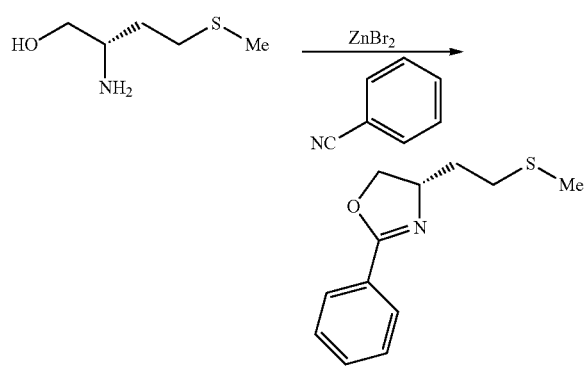

(S)-2-amino-4-(methylthio)butan-1-ol (10 g, 73.9 mmol) and zinc (II) bromide (0.50 g, 2.22 mmol) were mixed together in benzonitrile (18.0 mL, 185 mmol) and heated to 120° C. for 45 hrs. The mixture was purified by chromatography (330 g silica, 0-30% EtOAc/isohexanes) to afford (S)-4-(2-(methylthio)ethyl)-2-phenyl-4,5-dihydrooxazole (12.3 g, 52.8 mmol, 71.4% yield) as a colourless oil; Rt 1.39 min (Method 1), m/z 222 (M+H)+(ES+).

(S)—N-(tetrahydrothiophen-3-yl)benzamide

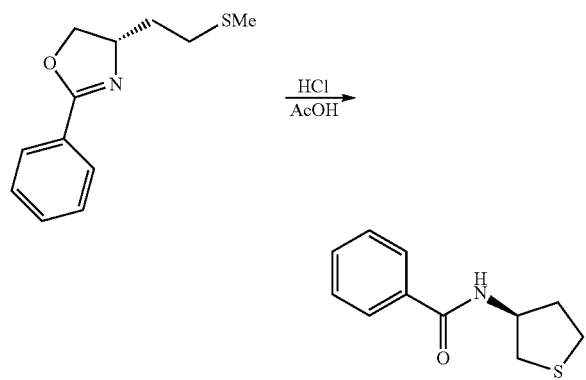

(S)-4-(2-(methylthio)ethyl)-2-phenyl-4,5-dihydrooxazole (12.3 g, 55.6 mmol) was dissolved in a 1.36M stock solution of HCl in acetic acid (163 mL, 222 mmol). The solution was heated to 130° C. for 16 hrs. The reaction mixture was cooled and evaporated to dryness to give a light brown solid which was triturated with ether to afford (S)—N-(tetrahydrothiophen-3-yl)benzamide (10.60 g, 46.0 mmol, 83% yield) as a colourless fluffy solid; Rt 1.56 min (Method 1), m/z 208 (M+H)+(ES+).

(S)—N-(1,1-dioxidotetrahydrothiophen-3-yl)benzamide

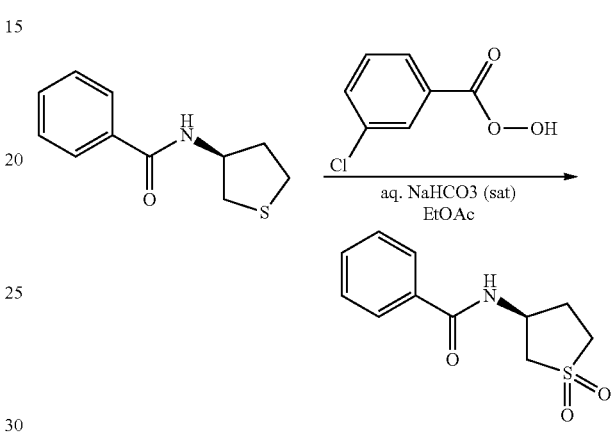

(S)—N-(tetrahydrothiophen-3-yl)benzamide (10.60 g, 51.1 mmol) was dissolved in EtOAc (200 mL). The solution was treated with saturated NaHCO3 (8.59 g, 102 mmol) solution in water (20 mL) followed by addition of m-CPBA (25.2 g, 112 mmol) portionwise. The reaction mixture was stirred at RT for 4 hrs. After filtration to remove the solid, the filtrate was washed with sodium metabisulphite solution (200 mL). The organic phase was washed sequentially with NaHCO3 solution (200 mL) and water (100 mL), dried (MgSO4), filtered and evaporated under reduced pressure to give crude product. The solid collected by filtration was combined with the crude product and slurried in diethyl ether (200 mL) for 10 mins. Filtration afforded (S)—N-(1,1-dioxidotetrahydrothiophen-3-yl)benzamide (11.04 g, 45.7 mmol, 89% yield) as a fluffy white solid. Rt 1.16 min (Method 1), m/z 240 (M+H)+(ES+).

(S)-3-aminotetrahydrothiophene 1,1-dioxide hydrochloride

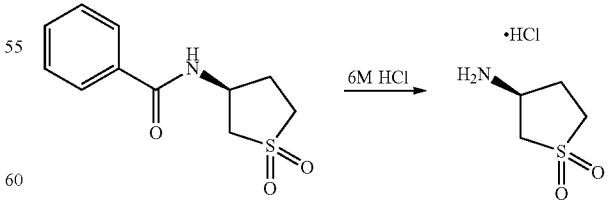

(S)—N-(1,1-dioxidotetrahydrothiophen-3-yl)benzamide (11.04 g, 46.1 mmol) was dissolved in 6M HCl (136 mL, 185 mmol). The solution was heated at 130° C. for 13 hrs. The reaction mixture was cooled to RT and placed in a ice-bath. The solid which precipitated was filtered and washed with 1M HCl (30 mL). The aqueous layer was evaporated under reduced pressure to give a solid. The solid was slurried in dioxane (50 mL), collected by filtration and washed with dioxane (10 mL) to afford (S)-3-aminotetrahydrothiophene 1,1-dioxide. HCl (7.51 g, 41.6 mmol, 90% yield) as a fluffy cream solid. 1H NMR (400 MHz, DMSO-d6) δ 8.79 (s, 3H), 3.98 (q, J=7.8 Hz, 1H), 3.55-3.37 (m, 2H), 3.27-3.12 (m, 2H), 2.57-2.43 (m, 1H), 2.21 (ddt, J=13.5, 9.3, 8.1 Hz, 1H).

(S)-3-((4-(3,5-dimethylisoxazol-4-yl)-2-nitrophenyl)amino)tetrahydrothiophene 1,1-dioxide

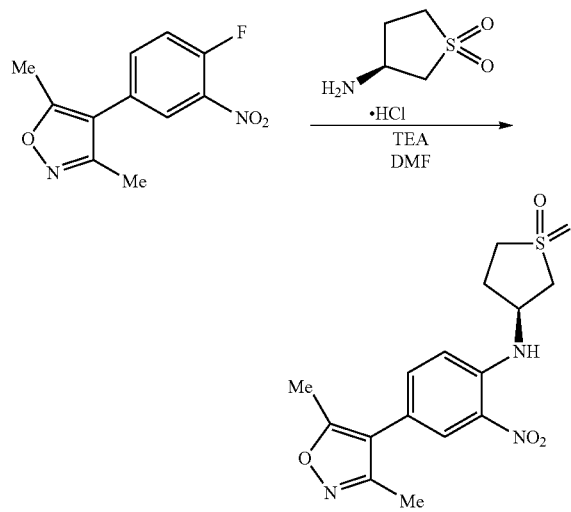

TEA (5.90 ml, 42.3 mmol) was added to a mixture of 4-(4-fluoro-3-nitrophenyl)-3,5-dimethylisoxazole (4 g, 16.93 mmol) and (S)-3-aminotetrahydrothiophene 1,1-dioxide. HCl (3.49 g, 20.32 mmol) in DMF (40 mL). The mixture was stirred at 70° C. for 18 hrs then quenched in ice water (100 mL). The product was collected by filtration and washed with water to afford (S)-3-((4-(3,5-dimethylisoxazol-4-yl)-2-nitrophenyl)amino)tetrahydrothiophene 1,1-dioxide (5.80 g, 15.68 mmol, 93% yield) as a bright orange solid. Rt 1.88 min (Method 1), m/z 352 (M+H)+(ES+).

(S)-3-((2-amino-4-(3,5-dimethylisoxazol-4-yl)phenyl)amino)tetrahydrothiophene 1,1-dioxide

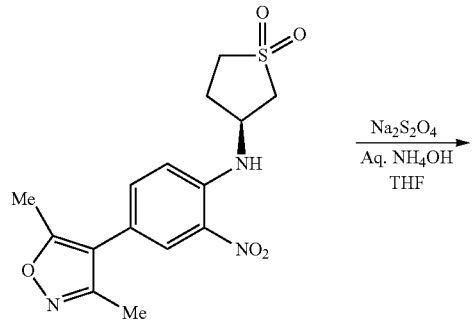

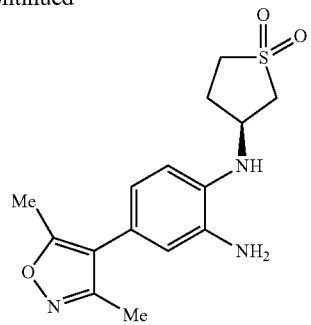

(S)-3-((4-(3,5-dimethylisoxazol-4-yl)-2-nitrophenyl)amino)tetrahydrothiophene 1,1-dioxide (5.80 g, 16.51 mmol) was added to a solution of sodium dithionite (28.7 g, 165 mmol) and 28% aqueous ammonium hydroxide solution (45.9 ml, 330 mmol) in THF (100 mL) and water (50 mL). The reaction mixture was stirred at RT for 2 hrs then concentrated in vacuo to remove the organic solvent. The remaining aqueous suspension was filtered to collect the solid. The solid was washed with water (500 mL) and triturated with DCM/ether (1:1, 100 mL) to afford (S)-3-((2-amino-4-(3,5-dimethylisoxazol-4-yl)phenyl)amino) tetrahydro thiophene 1,1-dioxide (3.90 g, 11.16 mmol, 67.6% yield) as a foamy pink solid; Rt 1.25 min (Method 1), m/z 322 (M+H)+(ES+).

(S)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide

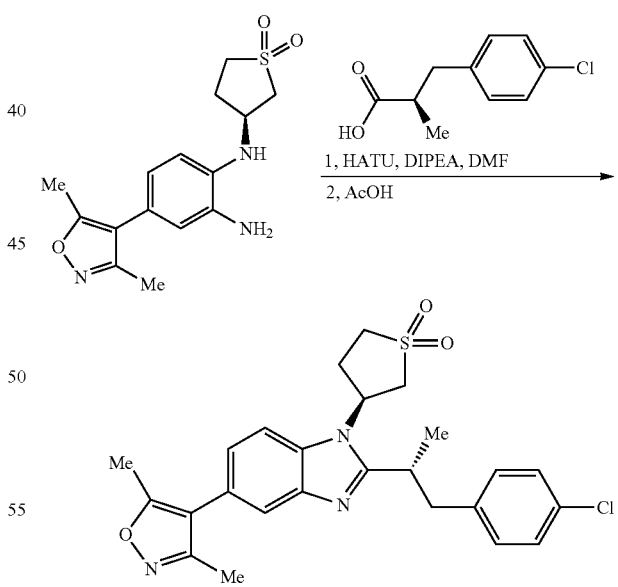

N-ethyl-N-isopropylpropan-2-amine (222 μL, 1.25 mmol) was added dropwise to a stirring solution of (R)-3-(4-chlorophenyl)-2-methylpropanoic acid (148 mg, 0.75 mmol) and 2-(3H-[1,2,3]triazolo[4,5-b]pyridin-3-yl)-1,1,3,3-tetramethylisouronium hexafluorophosphate(V) (284 mg, 0.747 mmol) in DMF (2 mL). After stirring for 10 mins (S)-3-((2-amino-4-(3,5-dimethylisoxazol-4-yl)phenyl)amino) tetrahydro thiophene 1,1-dioxide (200 mg, 0.622 mmol) was added and the reaction mixture was stirred at RT for 20 hrs. The reaction mixture was diluted with water (40 mL) and extracted with EtOAc (2×150 mL), dried (MgSO4), filtered and concentrated in vacuo. The crude intermediate was purified by chromatography (40 g silica, 0-100% EtOAc/isohexane, gradient elution). The product from the purification was dissolved in acetic acid (2 mL) and heated to 80° C. for 120 hrs. The reaction mixture was concentrated in vacuo and treated to chromatography on (40 g silica, 0-100% EtOAc/isohexane) then purified by preparative HPLC (Varian, Basic (0.1% Ammonium Bicarbonate), Basic, Waters X-Bridge Prep-C18, 5 μm, 19×50 mm column, 20-50% MeCN in Water) to afford (S)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide (28 mg, 9%) as a white solid; Rt 1.96 min (Method 1), m/z 484 (M+H)+(ES+); Chiral HPLC (Diacel Chiralpak IA, 5 um, 4.6×250 mm, gradient of 2-50% EtOH in isohexanes, +0.2% TFA) Rt=33.41 min, 100% de @ 254 nm; 1H NMR (400 MHz, DMSO-d6) δ 7.77-7.69 (m, 1H), 7.66 (dd, J=1.6, 0.6 Hz, 1H), 7.34 (d, J=8.4 Hz, 2H), 7.31-7.21 (m, 3H), 5.61 (p, J=9.9, 9.4 Hz, 1H), 3.68-3.27 (m, 5H), 3.14 (dd, J=13.6, 6.5 Hz, 1H), 2.93 (dd, J=13.7, 8.2 Hz, 1H), 2.71 (qd, J=12.9, 6.3 Hz, 1H), 2.58 (dt, J=13.5, 7.0 Hz, 1H), 2.41 (s, 3H), 2.24 (s, 3H), 1.26 (d, J=6.7 Hz, 3H).

Example 42 (S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide (S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide

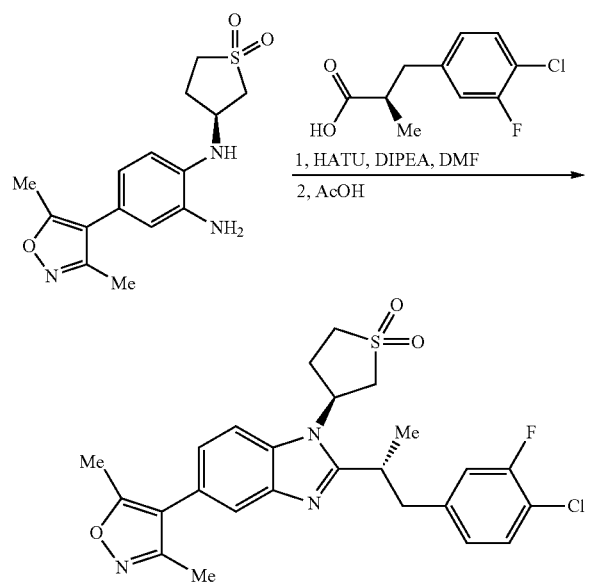

N-ethyl-N-isopropylpropan-2-amine (222 μL, 1.25 mmol) was added dropwise to a stirring solution of (R)-3-(4-chloro-3-fluorophenyl)-2-methylpropanoic acid (162 mg, 0.747 mmol) and 2-(3H-[1,2,3]triazolo[4,5-b]pyridin-3-yl)-1,1,3,3-tetramethyl isouronium hexafluorophosphate(V) (284 mg, 0.747 mmol) in DMF (2 mL). After stirring for 10 mins (S)-3-((2-amino-4-(3,5-dimethylisoxazol-4-yl)phenyl) amino) tetrahydro thiophene 1,1-dioxide (200 mg, 0.622 mmol) was added and the reaction mixture was stirred at RT for 20 hrs. The reaction mixture was diluted with water (40 mL) and extracted with EtOAc (2×150 mL), dried (MgSO4), filtered and concentrated in vacuo. The crude intermediate was purified by chromatography (40 g silica, 0-100% EtOAc/isohexane, gradient elution). The product from the purification was dissolved in acetic acid (2 mL) and heated to 80° C. for 120 hrs. The reaction mixture was concentrated in vacuo and treated to chromatography on (40 g silica, 0-100% EtOAc/isohexane) then purified by preparative HPLC (Varian, Basic (0.1% Ammonium Bicarbonate), Basic, Waters X-Bridge Prep-C18, 5 μm, 19×50 mm column, 20-50% MeCN in Water) to afford (S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide (23 mg, 0.045 mmol, 7.29% yield) as a white solid; Rt 2.07 min (Method 1), m/z 502/504 (M+H)+(ES+); Chiral HPLC (Diacel Chiralpak IA, 5 um, 4.6×250 mm, gradient of 2-50% EtOH in isohexanes, +0.2% TFA) Rt=39.62 min, 100% de @ 254 nm; 1H NMR (400 MHz, DMSO-d6) δ 7.74 (d, J=8.4 Hz, 1H), 7.69-7.63 (m, 1H), 7.49 (t, J=8.1 Hz, 1H), 7.41 (dd, J=10.6, 1.9 Hz, 1H), 7.26 (dd, J=8.3, 1.7 Hz, 1H), 7.14 (dd, J=8.2, 1.9 Hz, 1H), 5.65 (ddd, J=18.6, 10.9, 7.7 Hz, 1H), 3.69-3.41 (m, 3H), 3.43-3.27 (m, 2H), 3.18 (dd, J=13.7, 6.0 Hz, 1H), 2.95 (dd, J=13.7, 8.7 Hz, 1H), 2.81-2.67 (m, 1H), 2.60 (dt, J=13.8, 7.2 Hz, 1H), 2.41 (s, 3H), 2.24 (s, 3H), 1.24 (d, J=6.7 Hz, 3H).

Example 43: (S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide

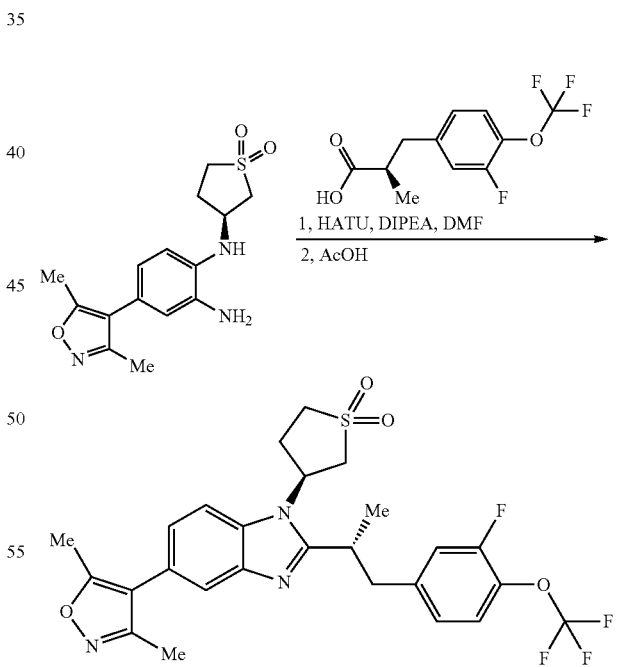

N-ethyl-N-isopropylpropan-2-amine (222 μL, 1.25 mmol) was added dropwise to a stirring solution of (R)-3-(3-fluoro-4-(trifluoromethoxy)phenyl)-2-methylpropanoic acid (0.199 g, 0.747 mmol) and 2-(3H-[1,2,3]triazolo[4,5-b]pyridin-3-yl)-1,1,3,3-tetramethylisouronium hexafluorophosphate(V) (284 mg, 0.747 mmol) in DMF (2 mL). After stirring for 10 mins (S)-3-((2-amino-4-(3,5-dimethylisoxazol-4-yl)phenyl) amino) tetrahydro thiophene 1,1-dioxide (200 mg, 0.622 mmol) was added and the reaction mixture was stirred at RT for 20 hrs. The reaction mixture was diluted with water (40 mL) and extracted with EtOAc (2×150 mL), dried (MgSO4), filtered and concentrated in vacuo. The crude intermediate was purified by chromatography (40 g silica, 0-100% EtOAc/isohexane, gradient elution). The product from the purification was dissolved in acetic acid (2 mL) and heated to 80° C. for 120 hrs. The reaction mixture was concentrated in vacuo and treated to chromatography on (40 g silica, 0-100% EtOAc/isohexanes) then purified by preparative HPLC (Varian, Basic (0.1% Ammonium Bicarbonate), Basic, Waters X-Bridge Prep-C18, 5 μm, 19×50 mm column, 30-55% MeCN in Water) to afford (S)-3-(5-(3,5-dimethylisoxazol-4-yl)-2-((R)-1-(3-fluoro-4-(trifluoromethoxy)phenyl)propan-2-yl)-1H-benzo[d]imidazol-1-yl)tetrahydrothiophene 1,1-dioxide (49 mg, 0.087 mmol, 13.99% yield) as a white solid. Rt 2.25 min (Method 1), m/z 552 (M+H)+(ES+); Chiral HPLC (Diacel Chiralpak IA, 5 um, 4.6×250 mm, gradient of 2-50% EtOH in isohexanes, +0.2% TFA) Rt=34.30 min, 100% de @ 254 nm; 1H NMR (400 MHz, DMSO-d6) δ 7.77-7.69 (m, 1H), 7.66 (dd, J=1.6, 0.6 Hz, 1H), 7.34 (d, J=8.4 Hz, 2H), 7.31-7.21 (m, 3H), 5.61 (p, J=9.9, 9.4 Hz, 1H), 3.68-3.27 (m, 5H), 3.14 (dd, J=13.6, 6.5 Hz, 1H), 2.93 (dd, J=13.7, 8.2 Hz, 1H), 2.71 (qd, J=12.9, 6.3 Hz, 1H), 2.58 (dt, J=13.5, 7.0 Hz, 1H), 2.41 (s, 3H), 2.24 (s, 3H), 1.26 (d, J=6.7 Hz, 3H); 1H NMR (400 MHz, DMSO-d6) δ 7.78-7.70 (m, 1H), 7.69-7.64 (m, 1H), 7.52-7.43 (m, 2H), 7.26 (dd, J=8.4, 1.7 Hz, 1H), 7.18 (dt, J=8.7, 1.2 Hz, 1H), 5.64 (ddd, J=18.7, 10.9, 7.6 Hz, 1H), 3.71-3.51 (m, 3H), 3.46 (ddd, J=14.4, 7.8, 1.9 Hz, 1H), 3.41-3.25 (m, 1H), 3.20 (dd, J=13.7, 6.0 Hz, 1H), 2.99 (dd, J=13.7, 8.5 Hz, 1H), 2.73 (dd, J=11.9, 6.4 Hz, 1H), 2.65-2.55 (m, 1H), 2.41 (s, 3H), 2.24 (s, 3H), 1.26 (d, J=6.7 Hz, 3H).

Example 44: (R)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole (R)-3-(4-chloro-3-fluorophenyl)-N-(5-(3,5-dimethylisoxazol-4-yl)-2-((tetrahydro-2H-pyran-4-yl)amino)phenyl)-2-methylpropanamide

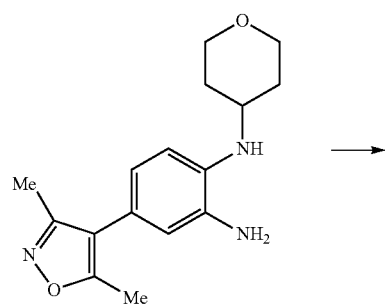

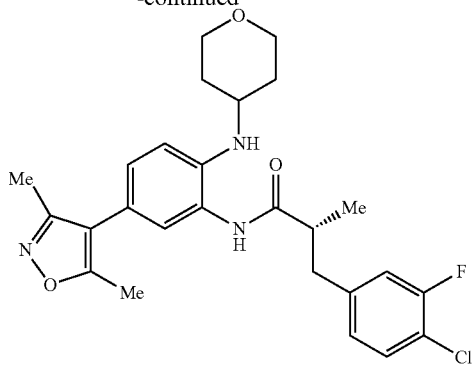

DIPEA (110 μl, 0.629 mmol) was added to a solution of 4-(3,5-dimethylisoxazol-4-yl)-N1-(tetrahydro-2H-pyran-4-yl)benzene-1,2-diamine (72.4 mg, 0.252 mmol), (R)-3-(4-chloro-3-fluorophenyl)-2-methylpropanoic acid (60 mg, 0.277 mmol) and HATU (124 mg, 0.327 mmol) in DMF (838 μl, 10.83 mmol) at rt and stirred at RT for 15 h. The mixture was diluted with EtOAc (20 mL), washed with aq NaHCO3 (20 mL), water (20 mL) and brine (10 mL), dried (MgSO4), filtered and evaporated in vacuo. The crude was purified by chromatography on silica gel (4 g column, 0-100% EtOAc in isohexane to afford (R)-3-(4-chloro-3-fluorophenyl)-N-(5-(3,5-dimethylisoxazol-4-yl)-2-((tetrahydro-2H-pyran-4-yl)amino)phenyl)-2-methylpropanamide (115 mg, 83%) as a red sticky gum; Rt 2.33 min (Method 1), m/z 486 (M+H)+(ES+).

(R)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole

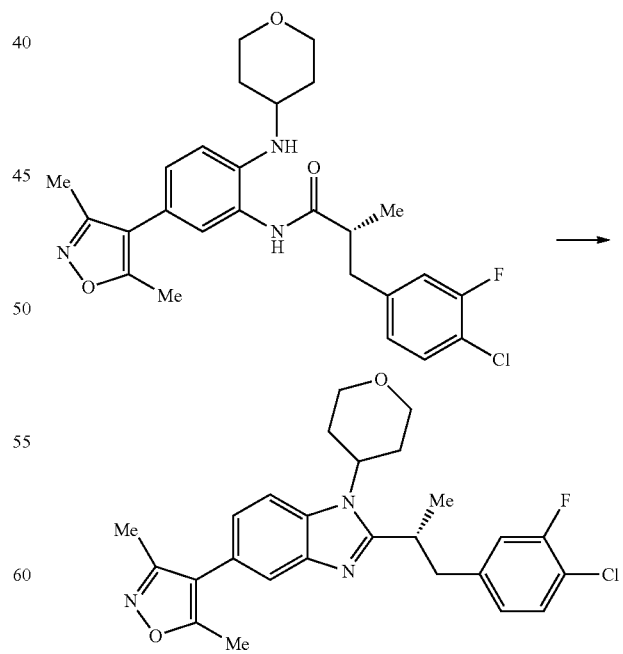

(R)-3-(4-chloro-3-fluorophenyl)-N-(5-(3,5-dimethylisoxazol-4-yl)-2-((tetrahydro-2H-pyran-4-yl)amino)phenyl)-2-methylpropanamide (115 mg, 0.237 mmol) was dissolved in glacial acetic acid (948 μl, 16.56 mmol) and stirred at 80° C. for 5 days, cooled down to rt and concentrated in vacuo. The residue was purified by flash chromatography (4 g, 0-3% (10% MeOHin DCM)/DCM) to give (R)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole (44 mg, 39%) was isolated as a pink solid; Rt 1.92 min (Method 1), m/z 468 (M+H)+(ES+); Chiral HPLC: (Diacel Chiralpak IA, 5 um, 4.6×250 mm, gradient of 50-50% EtOH in isohexanes+0.2% TFA)chiral HPLC agilent 1100; IA column 0.46 cm*25 cm/EtOH/i-Hexane+0.2% DEA; RT 22.95 mn, ee=82% @ 254 nm; 1H NMR (400 MHz, DMSO-d6) δ 7.68 (d, J=8.4 Hz, 1H), 7.60 (d, J=1.6 Hz, 1H), 7.45 (t, J=8.1 Hz, 1H), 7.37 (dd, J=10.7, 2.0 Hz, 1H), 7.14 (dd, J=8.4, 1.7 Hz, 1H), 7.09 (dd, J=8.2, 1.9 Hz, 1H), 4.74-4.56 (m, 1H), 4.05-3.94 (m, 2H), 3.77-3.68 (m, 1H), 3.64-3.48 (m, 2H), 3.19 (dd, J=13.6, 7.6 Hz, 1H), 3.03 (dd, J=13.6, 7.2 Hz, 1H), 2.40 (m+s, 5H), 2.23 (s, 3H), 1.79-1.71 (m, 1H), 1.38-1.31 (m, 1H), 1.29 (d, J=6.7 Hz, 3H).

Example 45: (S)-4-(2-(1-(4-chloro-3-fluorophenyl) propan-2-yl)-1-(tetrahydro-2H-pyran-4-yl)-1H-benzo[d]imidazol-5-yl)-3,5-dimethylisoxazole (S)-3-(4-chloro-3-fluorophenyl)-N-(5-(3,5-dimethyl-isoxazol-4-yl)-2-((tetrahydro-2H-pyran-4-yl)amino) phenyl)-2-methylpropanamide

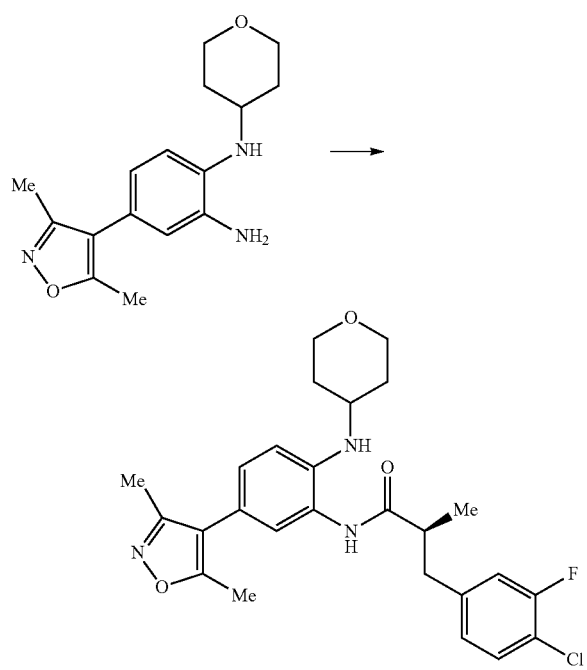

DIPEA (110 μl, 0.629 mmol) was added to a solution of 4-(3,5-dimethylisoxazol-4-yl)-N1-(tetrahydro-2H-pyran-4-yl)benzene-1,2-diamine (72.4 mg, 0.252 mmol), (S)-3-(4-chloro-3-fluorophenyl)-2-methylpropanoic acid (60 mg, 0.277 mmol) and HATU (124 mg, 0.327 mmol) in DMF (838 μl, 10.83 mmol) at rt and stirred at RT for 15 h. The mixture was diluted with EtOAc (20 mL), washed with aq NaHCO3 (20 mL), water (20 mL) and brine (10 mL), dried (MgSO4), filtered and evaporated in vacuo. The crude was purified by chromatography on silica gel (4 g column, 0-100% EtOAc in isohexane) to give (S)-3-(4-chloro-3-fluorophenyl)-N-(5-(3,5-dimethylisoxazol-4-yl)-2-((tetrahydro-2H-pyran-4-yl)amino)phenyl)-2-methylpropanamide (125 mg, 0.242 mmol, 96% yield) was isolated as a red sticky gum; Rt 2.33 min (Method 1), m/z 486 (M+H)+ (ES+).

(S)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole

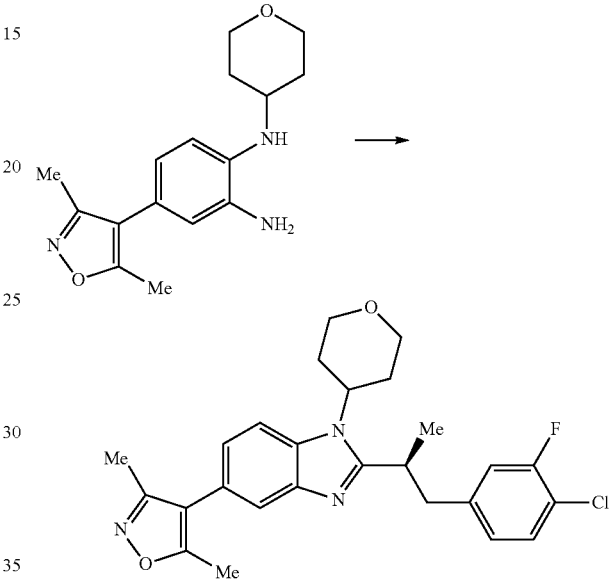

(S)-3-(4-chloro-3-fluorophenyl)-N-(5-(3,5-dimethylisoxazol-4-yl)-2-((tetrahydro-2H-pyran-4-yl)amino)phenyl)-2-methylpropanamide (0.125 g, 0.257 mmol) was dissolved in acetic acid (1.031 ml, 18.00 mmol) and stirred at 80° C. for 15 h, cooled down to rt and concentrated in vacuo. The residue was purified by flash chromatography (4 g, 0-3% (10% MeOHin DCM)/DCM) to give (S)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole (45 mg, 36%) was isolated as a pink solid; Rt 1.94 min (Method 1), m/z 468 (M+H)+(ES+); Chiral HPLC: (Diacel Chiralpak IA, 5 um, 4.6×250 mm, Chiral HPLC agilent 1100; IA column 0.46 cm*25 cm/EtOH/i-Hexane+0.2% DEA): RT=23.04 mn, 99% ee (S); 1H NMR (400 MHz, DMSO-d6) δ 7.68 (d, J=8.4 Hz, 1H), 7.60 (d, J=1.7 Hz, 1H), 7.45 (t, J=8.1 Hz, 1H), 7.37 (dd, J=10.7, 2.0 Hz, 1H), 7.14 (dd, J=8.4, 1.7 Hz, 1H), 7.09 (dd, J=8.2, 1.9 Hz, 1H), 4.72-4.58 (m, 1H), 4.07-3.91 (m, 2H), 3.72 (q, J=7.0 Hz, 1H), 3.64-3.46 (m, 2H), 3.24-3.14 (m, 1H), 3.03 (dd, J=13.7, 7.2 Hz, 1H), 2.40 (s+m, 5H), 2.23 (s, 3H), 1.76 (d, J=12.4 Hz, 1H), 1.34 (d, J=12.4 Hz, 1H), 1.29 (d, J=6.7 Hz, 3H).

Example 46: Biological Testing

Surface Plasmon Resonance (BIAcore) Analysis of Binding to EP300 and BRD4 BD1

BIAcore data for compound binding to EP300 and BRD4 was acquired using a T200 BIAcore instrument at 4° C. His-tagged EP300 Bromodomain (1046-1163) and BRD4 Bromodomain 1 (49-170) proteins were captured onto an NTA chip via a combined capture and amine coupling method. NTA groups were first chelated with 30 mM nickel chloride and then activated with 0.2 M N-ethyl-N'-(diethylaminopropyl)-carbodiimide (EDC) and 0.05 µM N-hydroxysuccimide (NHS).

Bromodomain proteins diluted to 9.6M in PBS 0.05% Tween-20 were injected at 101/min and covalently bound. Ethanolamine injections were performed to cap unreacted moieties on the surface and remove uncoupled protein. A typical immobilisation resulted in ~2-4 kRU of protein immobilised on the surface.

Test compounds were serially diluted to generate 1, 10, 100, 1000 and 10000 nM solutions in running buffer (PBS with 0.005% Tween-20, 0.1% DMSO). Using a flow rate of 90 µL/min throughout, runs consisted of injections of compound with escalating concentration, interspersed with buffer blank runs consisting of 5 repeat injections of running buffer.

Sensorgrams were analyzed with BIAevaluation (GE Healthcare) using a 1:1 interaction model to generate $k_a$ and $k_d$ values to describe the kinetics of binding. $K_D$ values were derived from the quotient of $k_d$ and $k_a$. All compounds were tested twice against the EP300 and BRD4 bromodomain surfaces to obtain geometric means of the kinetic and affinity parameters. All compounds tested gave $K_D$ values in the range of 0.5-10,000 nM.

Cell Viability Assay

The 22Rv1 cell line was obtained from ATCC (UK) and cultured according to the supplier's recommendations. Cell growth inhibitory activity of representative compounds was determined using the CellTiter-Glo® Luminescent Cell Viability Assay kit (Promega, USA).

22Rv1 cells were maintained in RPMI 1640 media containing 10% Foetal Bovine Serum, 2 mM Glutamine, 1 mM sodium pyruvate and 100 units of Penicillin-100 g of Streptomycin. Cells were incubated at 37° C. in a humidified atmosphere with 95% $O_2$ and 5% $CO_2$. 2000 cells were seeded per well in Poly-D-Lysine (PDL) coated 96-well black clear bottom plates (VWR, UK) in 50 µL of growth medium. After 48 hours, medium was removed and replaced with growth medium containing diluted test compounds. Compound dilutions were performed by serially diluting in half log intervals DMSO stocks at a maximum concentration of 10 mM, for a total of 7 dilutions. A 1 µl aliquot of each dilution point was added to 99 µl of growth medium and 50 µL added to each well containing cells, providing 100 µM compound at the maximum concentration point (1% DMSO). 1% DMSO treated cells served as a high control.

Cells were incubated for a further 72 hours at 37° C. and cell viability determined using the CellTiter-Glo® Luminescent Cell Viability Assay according to the manufacturer's instructions. Briefly, a volume of CellTiter-Glo® reagent equal to the volume of growth media was added to each well. Plates were shaken for approximately 2 minutes and incubated at room temperature (22° C.) for 10 minutes. The luminescence signal was measured using an Envision plate reader with an integration time of 1 second per well.

All data was normalised to the mean of 6 high-controls. The half maximum inhibitor concentration (IC50) was calculated from a 4-parameter logistic curve fit of the data using the Dotmatics software (UK). All compounds tested gave IC50 values in the range of 100 nM-100 µM, typically from 100 nM-30 µM.

Cell based assays are likely to show some variability due to the complexity of the system and it is understood that the results of these assays may vary as assay conditions are varied. Some level of cell growth inhibition is indicative of the compound having some inhibitory activity in specified cells, whereas lack of the inhibition below the highest concentration tested does not necessarily indicate the compound has no inhibitory activity on the cells.

Example 47: Tablet Composition

Tablets, each weighing 0.15 g and containing 25 mg of a compound of the invention are manufactured as follows:
Composition for 10,000 Tablets
Compound of the invention (250 g)
Lactose (800 g)
Corn starch (415 g)
Talc powder (30 g)
Magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 48: Injectable Formulation

| | |
|---|---|
| Compound of the invention | 200 mg |
| Hydrochloric Acid Solution 0.1M or Sodium Hydroxide Solution 0.1M q.s. | to pH 4.0 to 7.0 |
| Steriile water q.s. to | 10 mL |

The compound of the invention is dissolved in most of the water (35°-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 49: Intramuscular Injection

| | |
|---|---|
| Compound of the invention | 200 mg |
| Benzyl Alcohol | 0.10 g |
| Glycofurol 75 | 1.45 g |
| Water for injection q.s to | 3.00 mL |

The compound of the invention is dissolved in the glycofurol. The benzyl alcohol is then added and dissolved, and water added to 3 ml. The mixture is then filtered through a sterile micropore filter and sealed in sterile 3 ml glass vials (type 1).

Example 50: Syrup Formulation

| | |
|---|---|
| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A compound which is a benzimidazolyl isoxazole of formula (I):

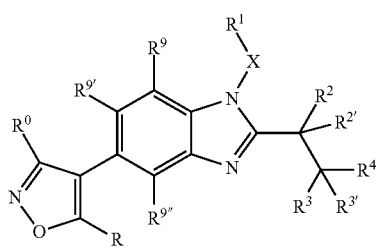

wherein:
- $R^0$ and R, which are the same or different, are each H or $C_{1-6}$ alkyl;
- $R^9$, $R^{9'}$ and $R^{9''}$, which are the same or different, are each H or F;
- X is $-(alk)_n-$, $-alk-C(=O)-NR-$, $-alk-NR-C(=O)-$ or $-alk-C(=O)-$;
- $R^1$ is selected from $-S(=O)_2R'$, a 4- to 6-membered, C-linked heterocyclic group which is unsubstituted or substituted and an N-linked spiro group of the following formula:

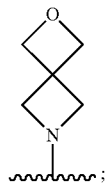 [SMILES: *N1CC2(COC2)C1]

- $R^2$ and $R^{2'}$, which are the same or different, are each H or $C_{1-6}$ alkyl; or $R^2$ and $R^{2'}$ form, together with the C atom to which they are attached, a $C_{3-6}$ cycloalkyl group;
- $R^3$ and $R^{3'}$, which are the same or different, are each H, $C_{1-6}$ alkyl, OH or F;
- $R^4$ is phenyl or a 5- to 12-membered, N-containing heteroaryl group and is unsubstituted or substituted;
- alk is $C_{1-6}$ alkylene;
- R' is $C_{1-6}$ alkyl; and
- n is 0 or 1;

or a pharmaceutically acceptable salt thereof.

2. A compound according to claim 1, wherein the benzimidazolyl isoxazole has the following formula (Ia):

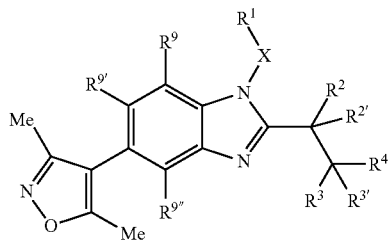

wherein each of $R^9$, $R^{9'}$, $R^{9''}$, X, $R^1$, $R^2$, $R^{2'}$, $R^3$, $R^{3'}$ and $R^4$ is as defined in claim 1 for formula (I).

3. A compound according to claim 1 wherein the benzimidazolyl isoxazole has the following formula (Ib):

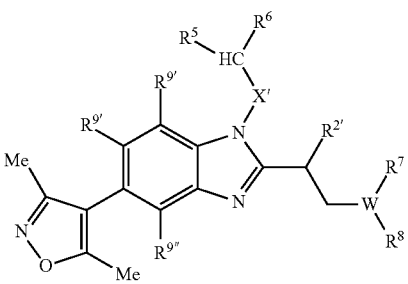

wherein:
- $R^9$, $R^{9'}$ and $R^{9''}$ are as defined above for formula (I);
- X' is $C_{1-3}$ alkylene or $-(CH_2)-C(=O)-NH-$;
- $R^{2'}$ is H, Me or Et;
- $R^5$ is H and $R^6$ is $-S(=O)_2Me$, or $R^5$ and $R^6$ form, together with the carbon atom to which they are attached, a heterocyclic group selected from pyrrolidinyl, thiopyranyl, pyranyl and piperidinyl, which group is unsubstituted or substituted;
- W is C or N; and
- $R^7$ and $R^8$ form, together with the C or N atom to which they are attached, a group selected from phenyl, pyridinyl, pyrimidinyl, quinolinyl, isoquinolinyl, pyrrolopyridinyl and quinoxalinyl, which group is unsubstituted or substituted.

4. A compound according to claim 1 wherein $R^2$ is H, $R^{2'}$ is $C_{1-6}$ alkyl, the $C-R^{2'}$ bond is $C \!-\!\!\!\!-\!\!\!\!- R^{2'}$ and the compound is the R enantiomer.

5. A compound according to claim 1 which is selected from:
- 4-(2-(1-(3-fluoro-4-methoxyphenyl)propan-2-yl)-1-(1-methylpyrrolidin-3-yl)-1H-benzo[d]imidazol-5-yl)-3,5-dimethylisoxazole;
- 4-(2-(1-(3-fluoro-4-(trifluoromethoxy)phenyl)propan-2-yl)-1-(1-methylpyrrolidin-3-yl)-1H-benzo[d]imidazol-5-yl)-3,5-dimethylisoxazole;
- 4-(2-(1-(4-chloro-3-fluorophenyl)propan-2-yl)-1-(3-(methylsulfonyl)propyl)-1H-benzo[d]imidazol-5-yl)-3,5-dimethylisoxazole;
- 4-(2-(1-(3-fluoro-4-(trifluoromethoxy)phenyl)propan-2-yl)-1-(3-(methylsulfonyl)propyl)-1H-benzo[d]imidazol-5-yl)-3,5-dimethylisoxazole;
- 4-(5-(3,5-dimethylisoxazol-4-yl)-2-(1-(3-fluoro-4-methoxyphenyl)propan-2-yl)-1H-benzo[d]imidazol-1-yl)tetrahydro-2H-thiopyran 1,1-dioxide;

4-(2-(1-(4-fluorophenyl)propan-2-yl)-1-(tetrahydro-2H-pyran-4-yl)-1H-benzo[d]imidazol-5-yl)-3,5-dimethylisoxazole;

3,5-dimethyl-4-(2-(1-(pyridin-2-yl)propan-2-yl)-1-(tetrahydro-2H-pyran-4-yl)-1H-benzo[d]imidazol-5-yl)isoxazole;

4-(2-(1-(3-fluoro-4-methoxyphenyl)propan-2-yl)-1-(1-methylpiperidin-4-yl)-1H-benzo[d]imidazol-5-yl)-3,5-dimethylisoxazole;

1-(4-((2-(1-(4-chlorophenyl)propan-2-yl)-5-(3,5-dimethylisoxazol-4-yl)-1H-benzo[d]imidazol-1-yl)methyl)piperidin-1-yl)ethan-1-one;

4-(2-(1-(3-fluoro-4-methoxyphenyl)propan-2-yl)-1-((tetrahydro-2H-pyran-4-yl)methyl)-1H-benzo[d]imidazol-5-yl)-3,5-dimethylisoxazole;

4-(2-(1-(4-chlorophenyl)propan-2-yl)-1-(2-(tetrahydro-2H-pyran-4-yl)ethyl)-1H-benzo[d]imidazol-5-yl)-3,5-dimethylisoxazole;

4-(2-(1-(3-chloro-4-(trifluoromethoxy)phenyl)propan-2-yl)-5-(3,5-dimethylisoxazol-4-yl)-1H-benzo[d]imidazol-1-yl)tetrahydro-2H-thiopyran 1,1-dioxide;

4-(2-(1-(3-chloro-4-(difluoromethoxy)phenyl)propan-2-yl)-5-(3,5-dimethylisoxazol-4-yl)-1H-benzo[d]imidazol-1-yl)tetrahydro-2H-thiopyran 1,1-dioxide;

4-(2-(3,4-dichlorophenethyl)-5-(3,5-dimethylisoxazol-4-yl)-1H-benzo[d]imidazol-1-yl)tetrahydro-2H-thiopyran 1,1-dioxide;

4-(2-(4-ethylphenethyl)-1-(3-(methylsulfonyl)propyl)-1H-benzo[d]imidazol-5-yl)-3,5-dimethylisoxazole;

4-(2-(2-(1H-pyrrolo[2,3-b]pyridin-3-yl)ethyl)-1-(tetrahydro-2H-pyran-4-yl)-1H-benzo[d]imidazol-5-yl)-3,5-dimethylisoxazole;

3,5-dimethyl-4-(2-(2-(quinoxalin-2-yl)ethyl)-1-(2-(tetrahydro-2H-pyran-4-yl)ethyl)-1H-benzo[d]imidazol-5-yl)isoxazole;

2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide;

2-(5-(3,5-dimethylisoxazol-4-yl)-2-(3-fluoro-4-methoxyphenethyl)-1H-benzo[d]imidazol-1-yl)-N-(tetrahydrofuran-3-yl)acetamide;

2-(5-(3,5-dimethylisoxazol-4-yl)-2-(1-(3-fluoro-4-methoxyphenyl)propan-2-yl)-1H-benzo[d]imidazol-1-yl)-N-(tetrahydrofuran-3-yl)acetamide;

4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole;

4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide;

(R)-4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole;

(S)-4-(2-(1-(3-fluoro-4-(trifluoromethoxy)phenyl)propan-2-yl)-1-(2-(tetrahydro-2H-pyran-4-yl)ethyl)-1H-benzo[d]imidazol-5-yl)-3,5-dimethylisoxazole;

3-(2-((R)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide;

3-(2-((S)-1-(3-chloro-4-(difluoromethoxy)phenyl)propan-2-yl)-5-(3,5-dimethylisoxazol-4-yl)-1H-benzo[d]imidazol-1-yl)tetrahydrothiophene 1,1-dioxide;

4-(2-((R)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole;

4-(2-((S)-1-(4-chloro-3-fluorophenyl)propan-2-yl)-1-((R)-1-(methylsulfonyl)pyrrolidin-3-yl)-1H-benzo[d]imidazol-5-yl)-3,5-dimethylisoxazole;

(R)-4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide;

(S)-4-(2-(1-(4-chlorophenyl)propan-2-yl)-5-(3,5-dimethylisoxazol-4-yl)-1H-benzo[d]imidazol-1-yl)tetrahydro-2H-thiopyran 1,1-dioxide;

4-(2-((R)-1-(4-chloro-3-fluorophenyl)propan-2-yl)-1-((S)-1-(methylsulfonyl)pyrrolidin-3-yl)-1H-benzo[d]imidazol-5-yl)-3,5-dimethylisoxazole;

4-(2-((S)-1-(4-chloro-3-fluorophenyl)propan-2-yl)-1-((S)-1-(methylsulfonyl)pyrrolidin-3-yl)-1H-benzo[d]imidazol-5-yl)-3,5-dimethylisoxazole;

(R)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide;

(S)-4-(2-(1-(4-chloro-3-fluorophenyl)propan-2-yl)-5-(3,5-dimethylisoxazol-4-yl)-1H-benzo[d]imidazol-1-yl)tetrahydro-2H-thiopyran 1,1-dioxide;

((R)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide;

((R)-3-(2-((S)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide;

(R)-3-(2-((R)-1-(4-chlorophenyl)propan-2-yl)-5-(3,5-dimethylisoxazol-4-yl)-1H-benzo[d]imidazol-1-yl)tetrahydrothiophene 1,1-dioxide;

(R)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide;

(S)-4-(5-(3,5-dimethylisoxazol-4-yl)-2-(1-(3-fluoro-4-(trifluoromethoxy)phenyl)propan-2-yl)-1H-benzo[d]imidazol-1-yl)tetrahydro-2H-thiopyran 1,1-dioxide;

(S)-3-(2-((R)-1-(4-chlorophenyl)propan-2-yl)-5-(3,5-dimethylisoxazol-4-yl)-H-benzo[d]imidazol-1-yl)tetrahydrothiophene 1,1-dioxide;

(S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide;

(S)-3-(2-((R)-1-(4-chloro-3-fluorophenyl)propan-2-yl)-5-(3,5-dimethylisoxazol-4-yl)-1H-benzo[d]imidazol-1-yl)tetrahydrothiophene 1,1-dioxide;

(R)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole;

(S)-4-(2-(1-(4-chloro-3-fluorophenyl)propan-2-yl)-1-(tetrahydro-2H-pyran-4-yl)-1H-benzo[d]imidazol-5-yl)-3,5-dimethylisoxazole;

and the pharmaceutically acceptable salts thereof.

6. A process for producing a compound as defined in claim 1, which process comprises treating a compound of formula (II):

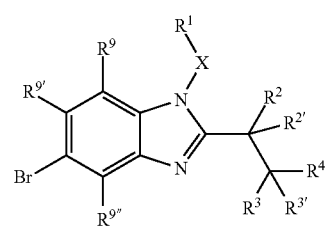

wherein each of $R^1$, $R^2$, $R^{2'}$, $R^3$, $R^{3'}$, $R^4$, $R^9$, $R^{9'}$ and $R^{9''}$ is as defined above for formula (I), with a boronic acid of formula (III):

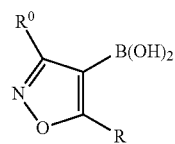
(III)

in which each of $R^0$ and R is as defined in claim 1 for formula (I), in the presence of $Pd(PPh_3)_4$ and $Na_2CO_3$ in aqueous ethanol.

7. A process according to claim 6, which further comprises converting the resulting benzimidazolyl isoxazole of formula (I) into a pharmaceutically acceptable salt thereof.

8. A pharmaceutical composition which comprises a pharmaceutically acceptable carrier or diluent and, as an active ingredient, a compound as defined in claim 1.

9. A compound as defined in claim 1 for use in the treatment of the human or animal body by therapy.

10. A compound as defined in claim 1 for use as a modulator of p300 and/or CBP activity.

11. A compound as defined in claim 1 for use in treating cancer.

12. A compound for use according to claim 11, wherein the cancer is a cancer that expresses AR.

13. Use of a compound as defined in claim 1 in the manufacture of a medicament for use as a modulator of p300 and/or CBP activity.

14. A method of treating cancer, which method comprises administering to a patient in need thereof a compound as defined in claim 1.

15. A method according to claim 14 wherein said compound is administered concurrently or sequentially with radiotherapy; or is administered concurrently, sequentially or as a combined preparation with another chemotherapeutic agent or agents.

16. A product comprising
  (i) a compound as defined in claim 1; and
  (ii) a chemotherapeutic agent;
for separate, simultaneous or sequential administration in the prophylactic or therapeutic treatment of cancer.

* * * * *